(12) United States Patent
Buyuktimkin et al.

(10) Patent No.: US 9,107,823 B2
(45) Date of Patent: Aug. 18, 2015

(54) FOAMABLE FORMULATION

(75) Inventors: Servet Buyuktimkin, San Diego, CA (US); Nadir Buyuktimkin, San Diego, CA (US); Edward Kisak, San Diego, CA (US); Jagat Singh, Scarborough (CA); John M. Newsam, La Jollla, CA (US); Dominic King-Smith, San Diego, CA (US); Bradley S. Galer, West Chester, PA (US)

(73) Assignee: NUVO RESEARCH INC., Mississauga (CA)

( * ) Notice: Subject to any disclaimer, the term of this patent is extended or adjusted under 35 U.S.C. 154(b) by 257 days.

(21) Appl. No.: 13/605,734

(22) Filed: Sep. 6, 2012

(65) Prior Publication Data

US 2013/0243701 A1  Sep. 19, 2013

Related U.S. Application Data

(63) Continuation of application No. PCT/US2011/028004, filed on Mar. 10, 2011.

(60) Provisional application No. 61/312,629, filed on Mar. 10, 2010.

(51) Int. Cl.
| | |
|---|---|
| *A61K 9/12* | (2006.01) |
| *A61K 31/10* | (2006.01) |
| *A61K 31/56* | (2006.01) |
| *A61K 9/00* | (2006.01) |
| *A61K 31/192* | (2006.01) |
| *A61K 31/196* | (2006.01) |
| *A61K 47/10* | (2006.01) |
| *A61K 47/20* | (2006.01) |

(52) U.S. Cl.
CPC .............. *A61K 9/122* (2013.01); *A61K 9/0014* (2013.01); *A61K 31/192* (2013.01); *A61K 31/196* (2013.01); *A61K 31/56* (2013.01); *A61K 47/20* (2013.01); *A61K 31/10* (2013.01); *A61K 47/10* (2013.01)

(58) Field of Classification Search
CPC ... A01N 25/02; A61K 31/192; A61K 31/196; A61K 47/10; A61K 47/20; A61K 9/0014; A61K 9/122; C11D 1/72; C11D 3/2068
See application file for complete search history.

(56) References Cited

U.S. PATENT DOCUMENTS

| | | | |
|---|---|---|---|
| 4,478,853 A | | 10/1984 | Chaussee |
| 4,575,515 A | | 3/1986 | Sandborn |
| 4,652,557 A | | 3/1987 | Sandborn |
| 5,322,683 A | | 6/1994 | Mackles et al. |
| 5,443,369 A | | 8/1995 | Martin et al. |
| 5,540,853 A | * | 7/1996 | Trinh et al. .................... 510/101 |
| 6,053,364 A | | 4/2000 | van der Heijden |
| 6,428,628 B1 | * | 8/2002 | Umemoto ...................... 134/38 |
| 6,547,162 B1 | | 4/2003 | De Regt et al. |
| 6,818,204 B2 | | 11/2004 | Lapidus |
| 7,147,133 B2 | | 12/2006 | Brouwer |
| 7,651,990 B2 | | 1/2010 | Asmus |
| 7,673,854 B2 | | 3/2010 | Brouwer |
| 7,726,518 B2 | | 6/2010 | Brouwer |
| 7,735,692 B2 | | 6/2010 | Nelson |
| 7,757,899 B2 | | 7/2010 | van der Heijden |
| 2005/0152957 A1 | | 7/2005 | Cleary et al. |
| 2005/0232869 A1 | | 10/2005 | Tamarkin et al. |
| 2005/0239675 A1 | * | 10/2005 | Makansi ........................ 510/223 |
| 2006/0078599 A1 | * | 4/2006 | Ebmeier et al. ............... 424/443 |
| 2006/0140984 A1 | * | 6/2006 | Tamarkin et al. ............. 424/400 |
| 2006/0275218 A1 | | 12/2006 | Tamarkin et al. |
| 2007/0243132 A1 | | 10/2007 | Russell-Jones |
| 2007/0292461 A1 | | 12/2007 | Tamarkin et al. |
| 2008/0069779 A1 | * | 3/2008 | Tamarkin et al. ............... 424/45 |
| 2008/0152596 A1 | * | 6/2008 | Friedman et al. ............... 424/43 |
| 2008/0153885 A1 | * | 6/2008 | Meadows et al. ............ 514/352 |
| 2008/0169311 A1 | | 7/2008 | van der Heijden |
| 2008/0206155 A1 | * | 8/2008 | Tamarkin et al. ............... 424/44 |
| 2008/0292560 A1 | | 11/2008 | Tamarkin et al. |
| 2008/0299220 A1 | | 12/2008 | Tamarkin et al. |

(Continued)

FOREIGN PATENT DOCUMENTS

| | | |
|---|---|---|
| CN | 101797239 A1 | 8/2010 |
| EP | 0522624 A1 | 1/1993 |

(Continued)

OTHER PUBLICATIONS

Aguzzi et al., "Penetration and Distribution of Thiocolchicoside through Human Skin: Comparison Between a Commercial Foam (Miotens®) and a Drug Solution," AAPS PharmSciTech, vol. 9, No. 4, Dec. 2008.
Banning, Maggi, "Topical diclofenac: clinical effectiveness and current uses in osteoarthritis of the knee and soft tissue injuries," Expert Opin. Pharmacother. (2008) 9(16):2921-2929.
Bergstrom et al., "Medication Formulation Affects Quality of Life: A Randomized Single-Blind Study of Clobetasol Propionate Foam 0.05% Compared with a Combined Program of Clobetasol Cream 0.05% for the Treatment of Psoriasis, " Therapeutics for the Clinician, vol. 72, Nov. 2003.
Boh L.E. et al.: 'Pharmacotherapy: A pathophysiological approach', 1999, Appleton & Lange article 'Osteoarthritis', pp. 1441-1459.
CTFA Cosmetic Ingredient Handbook, 1992, The Cosmetic, Toiletry, and Fragrance Association.

(Continued)

*Primary Examiner* — Brian-Yong Kwon
*Assistant Examiner* — Mark V Stevens
(74) *Attorney, Agent, or Firm* — Kilpatrick Townsend & Stockton LLP

(57) ABSTRACT

The present invention provides DMSO-containing foamable formulations, methods for preparation, and methods of treatment. The formulations can provide good permeability and bioavailability at the target site. Preferably, the formulations are useful for treating osteoarthritis. In one embodiment, the invention provides a foamable formulation for topical use, said formulation comprising DMSO, polyalkylene glycol alkyl ether, an active agent, a monohydric lower alcohol, a diol, and water. Preferably, the active agent is a non-steroidal anti-inflammatory drug, such as diclofenac sodium or ibuprofen.

30 Claims, 87 Drawing Sheets

(56) References Cited

U.S. PATENT DOCUMENTS

| | | | |
|---|---|---|---|
| 2008/0300311 | A1 | 12/2008 | Kisak et al. |
| 2008/0314931 | A1 | 12/2008 | van der Heijden |
| 2009/0039110 | A1 | 2/2009 | Brouwer |
| 2009/0212074 | A1 | 8/2009 | Brouwer |
| 2009/0236371 | A1 | 9/2009 | van der Heijden |
| 2010/0040561 | A9 | 2/2010 | Tamarkin et al. |
| 2010/0055055 | A1* | 3/2010 | Albeck et al. ............... 424/59 |
| 2010/0266510 | A1 | 10/2010 | Tamarkin et al. |
| 2010/0320232 | A1 | 12/2010 | van der Heijden |
| 2012/0087872 | A1 | 4/2012 | Tamarkin et al. |

FOREIGN PATENT DOCUMENTS

| | | |
|---|---|---|
| EP | 0535327 B1 | 10/1996 |
| IN | 976/BOM/1999 | 12/1999 |
| WO | WO 97/13585 A1 | 4/1997 |
| WO | WO 99/54054 A1 | 10/1999 |
| WO | WO 02/042005 A1 | 5/2002 |
| WO | WO 2004/069418 A1 | 8/2004 |
| WO | WO 2005/028121 A1 | 3/2005 |
| WO | WO 2006/001445 A1 | 1/2006 |
| WO | WO 2006/112701 A1 | 10/2006 |
| WO | WO 2006/112704 A1 | 10/2006 |
| WO | WO 2007/086731 A1 | 8/2007 |
| WO | WO 2008/007943 A1 | 1/2008 |
| WO | WO 2008/032227 A2 | 3/2008 |
| WO | WO 2008032227 A2 * | 3/2008 |
| WO | WO 2008/038140 A2 | 4/2008 |
| WO | WO 2008/038147 A2 | 4/2008 |
| WO | WO 2008/045822 A1 | 4/2008 |
| WO | WO 2008/133491 A1 | 11/2008 |
| WO | WO 2009/090558 A2 | 7/2009 |
| WO | WO 2009/136781 A1 | 11/2009 |
| WO | WO 2010/125470 A2 | 11/2010 |
| WO | WO 2011063531 A1 * | 6/2011 |

OTHER PUBLICATIONS

Durian, D. J., Weitz, D. A.: 'Kirk-Othmer Encyclo. Chem. Tech.', vol. 11, 1994 article 'Foams', pp. 783-805.

Franz, T. J.: 'Percutaneous absorption: on the relevance of in vitro data' J. Invest. Derm. vol. 64, 1975, pp. 190-195.

Kantarci et al., "In Vitro Permeation of Diclofenac Sodium from Novel Microemulsion Formulations Through Rabbit Skin," Drug Development Research 65:17-25 (2005).

Lakovska, I. et al., "Investigations on the Dynamics of Drug Release from Ointment Bases," Pharm. Ind. 1977, 39(2), 174-176.

Moen, Marit D., "Topical Diclofenac Solution," Drugs 2009; 69 (18): 2621-2632.

NASA Science, "The_Strange_Physics_of_Foam," NASA Science, Science News, Jun. 9, 2003, http://science1.nasa.gov/science-news/science-at-nasa/2003/09jun_foam/, 4 pages.

Ostrenga, J. et al., "Significance of vehicle composition I: relationship between topical vehicle composition, skin penetrability, and clinical efficacy," Journal of Pharmaceutical Sciences, 60: 1175-1179 (1971).

Pilpel, N., "Foams in pharmacy," Endeavour, New Series, Pergamon Press, Great Britain, vol. 9, No. 2, 1985.

Rosenstein: 'Topical agents in the treatment of rheumatic disorders' Rheum. Dis. Clin North Am. vol. 25, 1999, pp. 899-918.

Shen, WW et al., "Effect of Nonionic Surfactants on Percutaneous Absorption of Salicylic Acid and Sodium Salicylate in the Presence of Dimethyl Sulfoxide," Journal of Pharmaceutical Sciences 1976, 65(12), 1780-1783.

Simon, Lee S., "Do topical NSAIDs work?" Nature Clinical Practice Rheumatology, Sep. 2008 vol. 4 No. 9, pp. 458-459.

Tamarkin, Dov et al., "Emollient foam in topical drug delivery," Expert Opin. Drug Deliv. (2006) 3(6), pp. 799-807.

Towheed, Tanveer E., "Pennsaid® Therapy for Osteoarthritis of the Knee: A Systematic Review and Metaanalysis of Randomized Controlled Trials," The Journal of Rheumatology 2006; 33:3, pp. 567-573.

Wishart, DS et al., "DrugBank: A comprehensive resource for in silico drug discovery and exploration," Nucleic Acids Res., Jan. 1, 2006; 34 (database issue): D668-672. PMID: 16381955.

Zhao, Yanjun, M.B. Brown, S.A. Jones, "Pharmaceutical foams: are they the answer to the dilemma of topical nanoparticles?" Nanomedicine: Nanotechnology, Biology and Medicine, vol. 6, Issue 2, pp. 227-236, Apr. 2010.

International Search Report issued in connection with corresponding International Application No. PCT/US2011/028004, mailed Mar. 9, 2012, 2 pages.

Zhao, Yanjun et al., "Dynamic foams in topical drug delivery," Journal of Pharmacy and Pharmacology, 2010, 62: 678-684.

Arzhavitina, A. et al., "Foams for pharmaceutical and cosmetic application," International Journal of Pharmacuetics, 2010, 394: 1-17.

Purdon, Carryn H. et al., "Foam Drug Delivery in Dermatology—Beyond the Scalp," Am J Drug Deliv, 2003, 1(1): 71-75.

* cited by examiner

Formulations' appearance at 0 hr (after 30 sec of manual shaking)

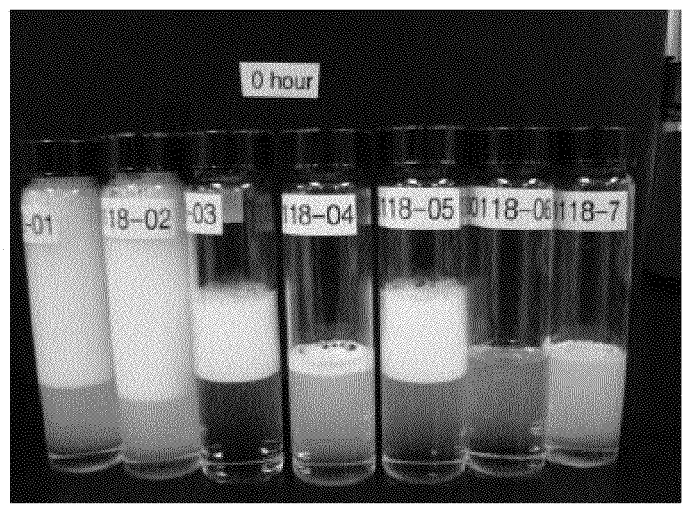

Foam 1: contains 98 % DMSO base and other 3 ingredients.
Foam 2: contains 98 % DMSO base and other 2 ingredients, but no SBDS.
Foam 3: contains 98 % DMSO base and other 2 ingredients, but no cholesterol.
Foam 4: contains 98 % DMSO base and other 2 ingredients, but no Brij.
Foam 5: contains 98 % DMSO base and Brij only.
Foam 6: contains 98 % DMSO base and surfactant.
Foam 7: contains 98% DMSO base and cholesterol.

*FIG. 1*

Formulations' appearance after 2 min (after 30 sec of manual shaking)

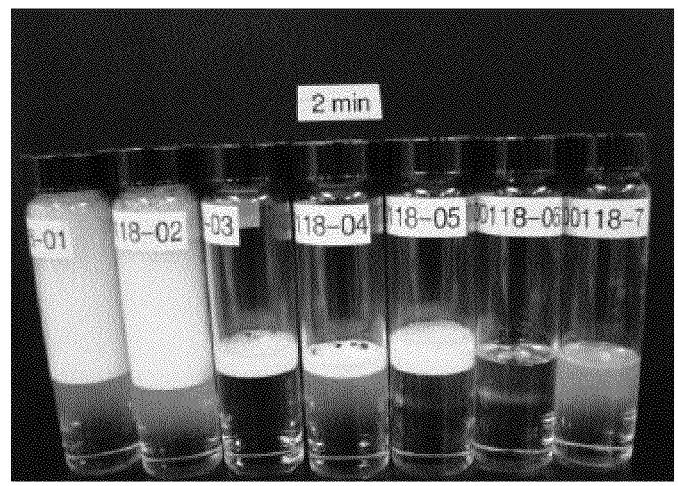

Foam 1: contains 98 % DMSO base and other 3 ingredients.
Foam 2: contains 98 % DMSO base and other 2 ingredients, but no SBDS.
Foam 3: contains 98 % DMSO base and other 2 ingredients, but no cholesterol.
Foam 4: contains 98 % DMSO base and other 2 ingredients, but no Brij.
Foam 5: contains 98 % DMSO base and Brij only.
Foam 6: contains 98 % DMSO base and surfactant.
Foam 7: contains 98% DMSO base and cholesterol.

*FIG. 2*

Formulations' appearance after 5 min (after 30 sec of manual shaking)

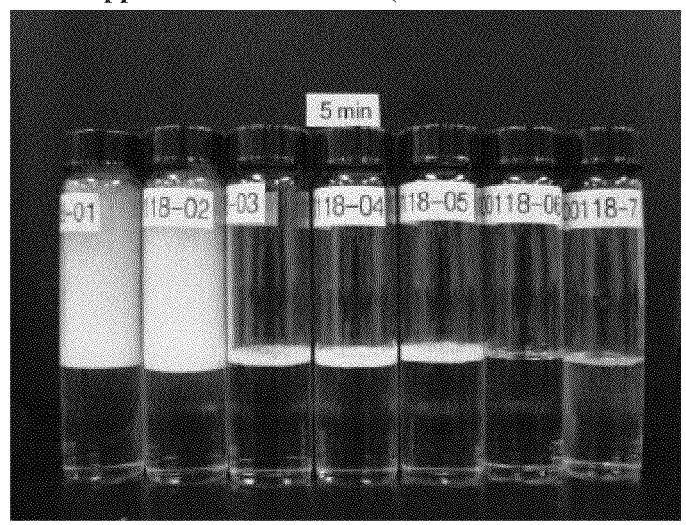

Foam 1: contains 98 % DMSO base and other 3 ingredients.
Foam 2: contains 98 % DMSO base and other 2 ingredients, but no SBDS.
Foam 3: contains 98 % DMSO base and other 2 ingredients, but no cholesterol.
Foam 4: contains 98 % DMSO base and other 2 ingredients, but no Brij.
Foam 5: contains 98 % DMSO base and Brij only.
Foam 6: contains 98 % DMSO base and surfactant.
Foam 7: contains 98% DMSO base and cholesterol.

*FIG. 3*

Formulations' appearance after 35 min (after 30 sec of manual shaking)

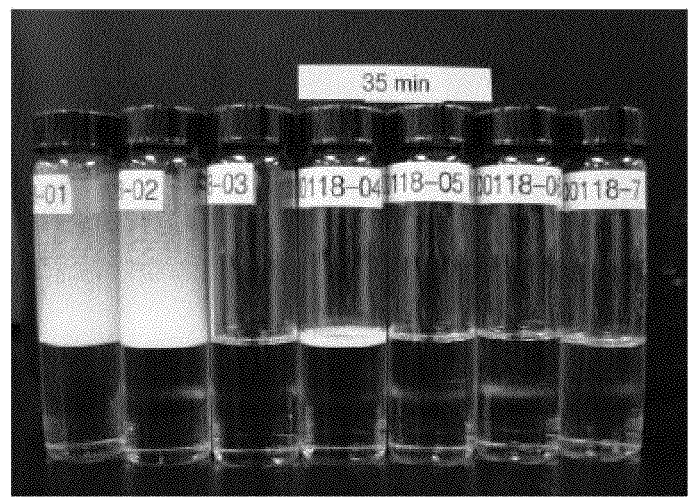

Foam 1: contains 98 % DMSO base and other 3 ingredients.
Foam 2: contains 98 % DMSO base and other 2 ingredients, but no SBDS.
Foam 3: contains 98 % DMSO base and other 2 ingredients, but no cholesterol.
Foam 4: contains 98 % DMSO base and other 2 ingredients, but no Brij.
Foam 5: contains 98 % DMSO base and Brij only.
Foam 6: contains 98 % DMSO base and surfactant.
Foam 7: contains 98% DMSO base and cholesterol.

*FIG. 4*

Formulations' appearance after 1 hour (after 30 sec of manual shaking)

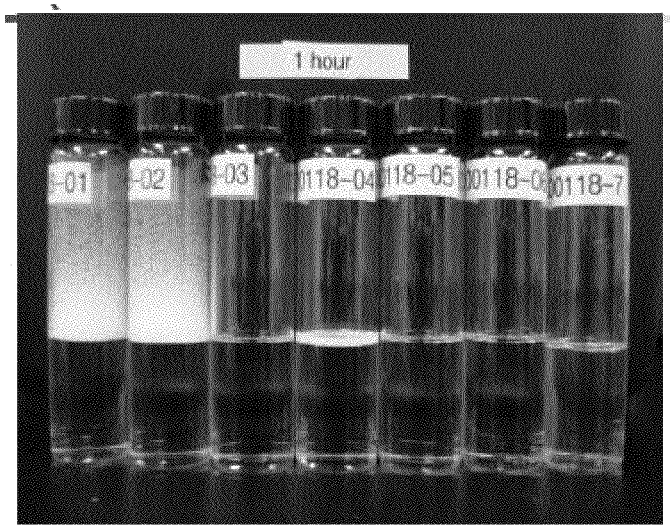

Foam 1: contains 98 % DMSO base and other 3 ingredients.
Foam 2: contains 98 % DMSO base and other 2 ingredients, but no SBDS.
Foam 3: contains 98 % DMSO base and other 2 ingredients, but no cholesterol.
Foam 4: contains 98 % DMSO base and other 2 ingredients, but no Brij.
Foam 5: contains 98 % DMSO base and Brij only.
Foam 6: contains 98 % DMSO base and surfactant.
Foam 7: contains 98% DMSO base and cholesterol.

*FIG. 5*

Formulations' appearance after 2 hours (after 30 sec of manual shaking)

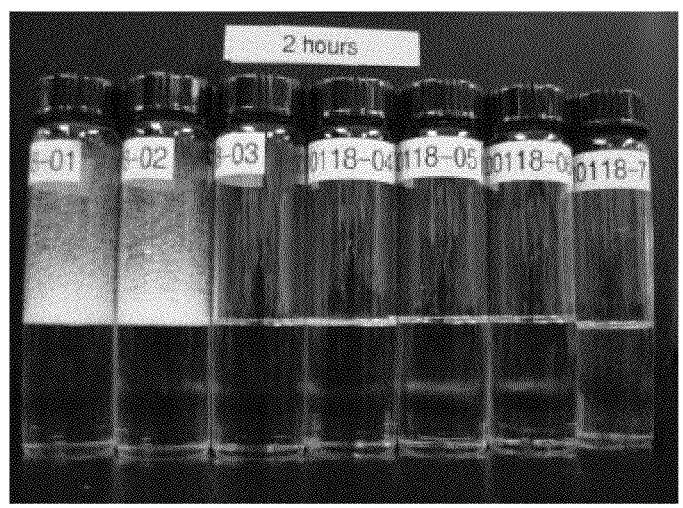

Foam 1: contains 98 % DMSO base and other 3 ingredients.
Foam 2: contains 98 % DMSO base and other 2 ingredients, but no SBDS.
Foam 3: contains 98 % DMSO base and other 2 ingredients, but no cholesterol.
Foam 4: contains 98 % DMSO base and other 2 ingredients, but no Brij.
Foam 5: contains 98 % DMSO base and Brij only.
Foam 6: contains 98 % DMSO base and surfactant.
Foam 7: contains 98% DMSO base and cholesterol.

*FIG. 6*

Formulations' appearance after 3 hours (after 30 sec of manual shaking)

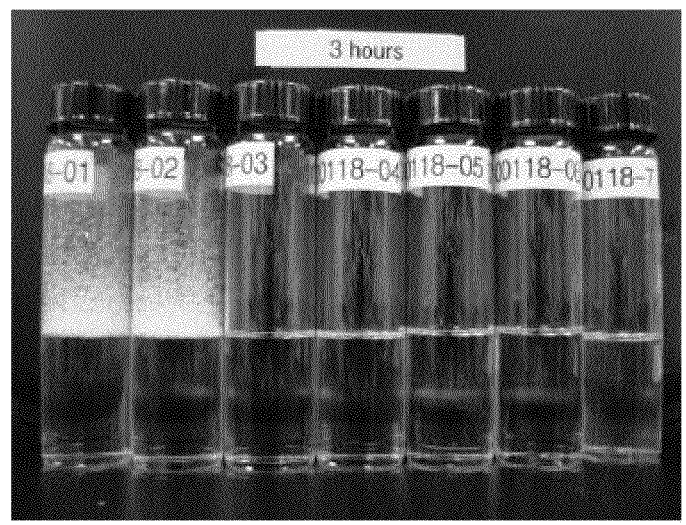

Foam 1: contains 98 % DMSO base and other 3 ingredients.
Foam 2: contains 98 % DMSO base and other 2 ingredients, but no SBDS.
Foam 3: contains 98 % DMSO base and other 2 ingredients, but no cholesterol.
Foam 4: contains 98 % DMSO base and other 2 ingredients, but no Brij.
Foam 5: contains 98 % DMSO base and Brij only.
Foam 6: contains 98 % DMSO base and surfactant.
Foam 7: contains 98% DMSO base and cholesterol.

*FIG. 7*

Formulations' appearance after 24 hours (after 30 sec of manual shaking)

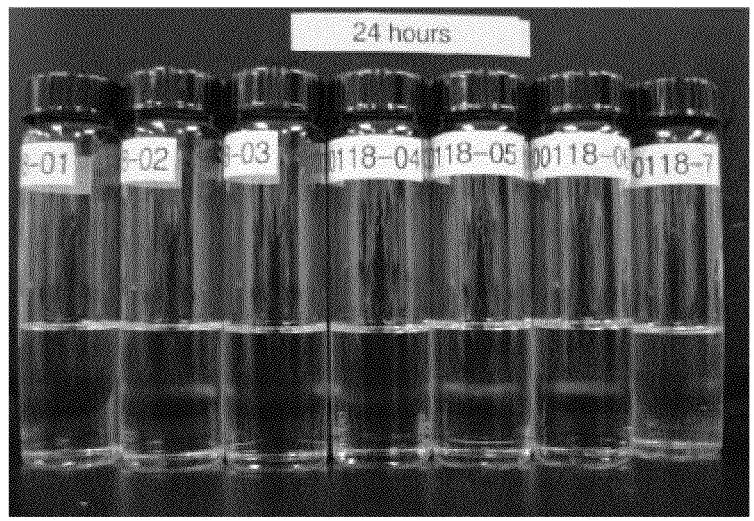

Foam 1: contains 98 % DMSO base and other 3 ingredients.
Foam 2: contains 98 % DMSO base and other 2 ingredients, but no SBDS.
Foam 3: contains 98 % DMSO base and other 2 ingredients, but no cholesterol.
Foam 4: contains 98 % DMSO base and other 2 ingredients, but no Brij.
Foam 5: contains 98 % DMSO base and Brij only.
Foam 6: contains 98 % DMSO base and surfactant.
Foam 7: contains 98% DMSO base and cholesterol.

*FIG. 8*

Spraying studies

Formulation 1 after spraying – at 0 hr

Spraying studies

Formulation 1 after spraying – after 2 min

| Ingredients | Formulations ||||||| 
|---|---|---|---|---|---|---|---|
| | P100118-01 | P100118-02 | P100118-03 | P100118-04 | P100118-05 | P100118-06 | P100118-07 |
| DMSO Base | 98 | 98 | 98 | 98 | 98 | 99.85 | 99.7 |
| Brij 30 | 1.7 | 1.85 | 1.85 | | 2 | | |
| Cholesterol | 0.15 | 0.15 | | 0.15 | | | 0.3 |
| Sodium dodecyl benzene sulfonate | 0.15 | | 0.15 | 0.15 | | 0.15 | |

| Ingredients | Formulations | | | | | | |
|---|---|---|---|---|---|---|---|
| | P100118-01 | P100118-02 | P100118-03 | P100118-04 | P100118-05 | P100118-06 | P100118-07 |
| DMSO Base | 98 | 98 | 98 | 98 | 98 | 99.85 | 99.7 |
| Brij 30 | 1.7 | 1.85 | 1.85 | | 2 | | |
| Cholesterol | 0.15 | 0.15 | | 0.15 | | | 0.3 |
| Sodium dodecyl benzene sulfonate | 0.15 | | 0.15 | 0.15 | | 0.15 | |

| | Formulations | | | | | | |
|---|---|---|---|---|---|---|---|
| Ingredients | P100118-01 | P100118-02 | P100118-03 | P100118-04 | P100118-05 | P100118-06 | P100118-07 |
| DMSO Base | 98 | 98 | 98 | 98 | 98 | 99.85 | 99.7 |
| Brij 30 | 1.7 | 1.85 | 1.85 | | 2 | | |
| Cholesterol | 0.15 | 0.15 | | 0.15 | | | 0.3 |
| Sodium dodecyl benzene sulfonate | 0.15 | | 0.15 | 0.15 | | 0.15 | |

| Ingredients | Formulations | | | | | | |
|---|---|---|---|---|---|---|---|
| | P100118-01 | P100118-02 | P100118-03 | P100118-04 | P100118-05 | P100118-06 | P100118-07 |
| DMSO Base | 98 | 98 | 98 | 98 | 98 | 99.85 | 99.7 |
| Brij 30 | 1.7 | 1.85 | 1.85 | | 2 | | |
| Cholesterol | 0.15 | 0.15 | | 0.15 | | | 0.3 |
| Sodium dodecyl benzene sulfonate | 0.15 | | 0.15 | 0.15 | | 0.15 | |

| Ingredients | Formulations |||||||
|---|---|---|---|---|---|---|---|
| | P100118-01 | P100118-02 | P100118-03 | P100118-04 | P100118-05 | P100118-06 | P100118-07 |
| DMSO Base | 98 | 98 | 98 | 98 | 98 | 99.85 | 99.7 |
| Brij 30 | 1.7 | 1.85 | 1.85 | | 2 | | |
| Cholesterol | 0.15 | 0.15 | | 0.15 | | | 0.3 |
| Sodium dodecyl benzene sulfonate | 0.15 | | 0.15 | 0.15 | | 0.15 | |

*FIG. 21*

*In Vitro* Diclofenac Delivery from P100223 Series Foamable Formulations

| Time | Cumulative Diclofenac Delivery | | | | |
|---|---|---|---|---|---|
| | Pennsaid® | P100223-01 | P100223-02 | P100223-02a | P100223-02b |
| 4 hours | 0.54±0.39 | 1.10±0.68 | 0.14±0.14 | 0.16±0.16 | 0.17±0.17 |
| 20 hours | 7.61±2.55 | 9.92±0.89 | 9.83±2.12 | 10.09±0.51 | 7.59±1.80 |
| 24 hours | 9.19±2.63 | 11.18±1.07 | 11.17±2.07 | 11.54±0.66 | 10.17±1.93 |
| ER | 1.00 | 1.20 | 1.20 | 1.21 | 1.11 |

| Ingredients | Formulations | | | |
|---|---|---|---|---|
| | P100223-1 | P100223-2 | P100223-2a | P100223-2b |
| DMSO Base | 98 | 98 | 98 | 99.85 |
| Brij 30 | 1.7 | 1.7 | 1.85 | - |
| Cholesterol | 0.15 | 0.15 | - | - |
| Sodium dodecyl benzene sulfonate | 0.15 | - | - | - |
| Sodium laureth sulfate | - | 0.15 | 0.15 | 0.15 |

Formulations:

| Ingredients | Pennsaid | P100223-01 | P100223-03 | P100223-04 | P100223-05 | P100223-06 | P100223-07 | P100223-08 | P100223-09 | P100223-10 | P100223-11 |
|---|---|---|---|---|---|---|---|---|---|---|---|
| Percentage in | wt/wt% | wt/wt% | wt/wt% | wt/wt% | wt/wt% | wt/wt% | wt/wt% | wt/wt% | wt/wt% | wt/wt% | wt/wt% |
| DMSO Base | | 98 | 98 | 98 | 98.15 | 98.15 | 98 | 98 | 98 | 98 | 98 |
| Brij 30 | | 1.7 | 1 | 1 | 1 | 1 | 1 | 1 | | | 2 |
| Cholesterol | | 0.15 | 0.15 | 0.15 | 0.15 | 0.15 | | | | | |
| Sodium dodecyl benzene | | 0.15 | 0.15 | 0.15 | | | | | | | |
| Brij 78 | | | 0.7 | | 0.7 | | 1 | | 2 | | |
| Brij 98 | | | | 0.7 | | 0.7 | | 1 | | 2 | 2 |

Note: Formulations F-07 and F-09 were cloudy. Cloudiness did not significantly improve after many filtrations.

Airspray M3 Mini Foamer general properties

| Properties | Air to liquid ratio 10 S10 | Comments |
|---|---|---|
| Application torque | 1.3 Nm | ± 0.2 Nm |
| Overcap removal force 200 mm/min | 15 N Min | Pulled straight from collar |
| Actuation force 200 mm/min (test stroke 90%) | 23.0 N Max | No liquid used. Force required may differ with different liquid viscosity's |
| Length of stroke | 11.0 mm | Full stroke |
| Full strokes to prime | 7 Max | Apply full strokes (based on 35mm diptube length with 50 ml bottle) |
| Dosage per full stroke | 0.4 ml (±0.1 ml) | Output may differ with different viscosity's being used. |
| Diptube length minimum. | 32 mm / 1.62 inch | To be specified by customer, depends on bottle being used. |
| Diptube length maximum | 145 mm / 5.7 inch | Diptube lengths between 145 mm / 5.7 inch and 185 mm / 7.2 inch upon special requests. |
| Mesh count per inch inner / outer mesh | 100 / 200<br>150 / 255 | To be finalized in accordance with customer |

Airspray international b.v. and Airspray inc reserve the right to alter specifications without further notice.
All information supplied by Airspray International and Airspray Inc is based on our current knowledge and is believed to be reliable.

M3-30A04

*FIG. 39*

Foam Collapse for Formulation P100310-01 after being dispensed with Rexam M3 Foamer and after being rubbed on application site
Time = 0 hour
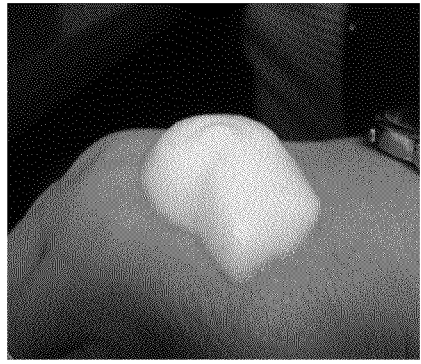
Time = 1 minute
Time = 2 minute
Time = 0 hour after being rubbed
Time = 2 minutes after being rubbed
*FIG. 42*

Foam Collapse for Formulation P100310-02 after being dispensed with Rexam M3 Foamer and after being rubbed on application site
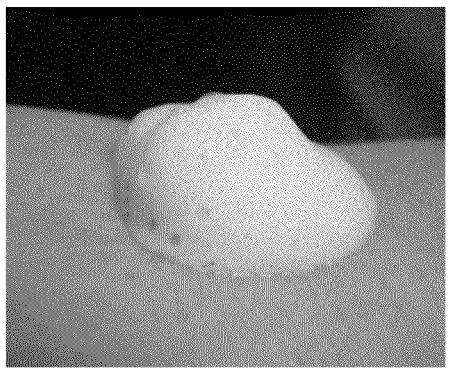
Time = 0 hour
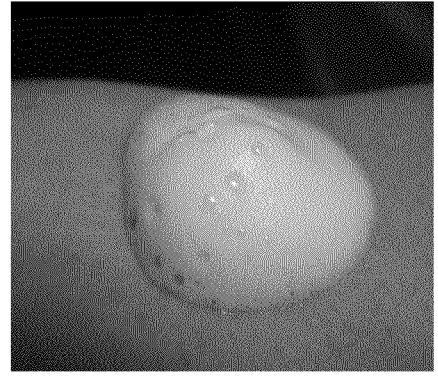
Time = 1 minute
Time = 2 minute
Time = 0 hour after being rubbed
Time = 2 minutes after being rubbed
*FIG. 43*

Foam Collapse for Formulation P100310-03 after being dispensed with Rexam M3 Foamer and after being rubbed on application site
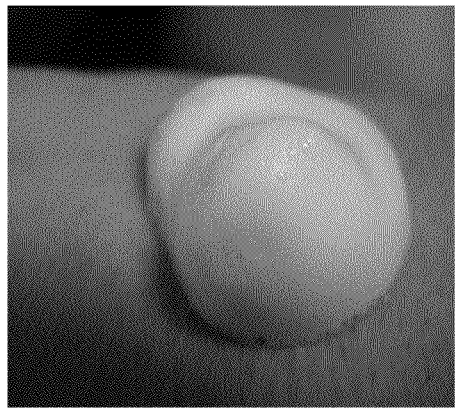
Time = 0 hour
Time = 1 minute
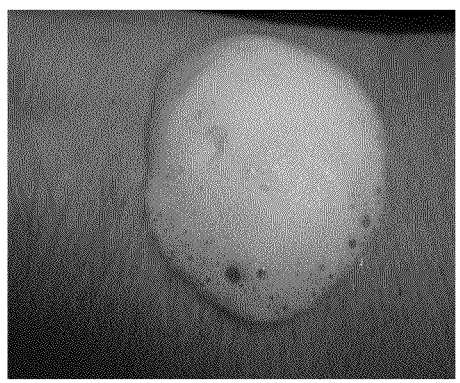
Time = 2 minute
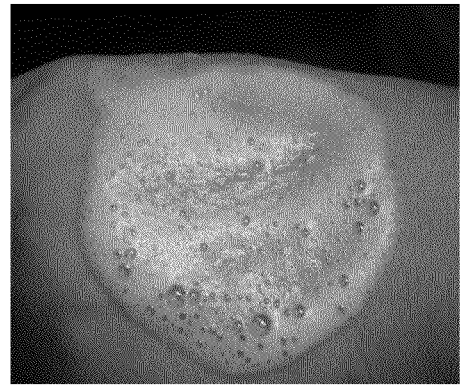
Time =0 hour after being rubbed
Time = 2 minutes after being rubbed
*FIG. 44*

Foam Collapse for Formulation P100310-04 after being dispensed with Rexam M3 Foamer and after being rubbed on application site
Time = 0 hour
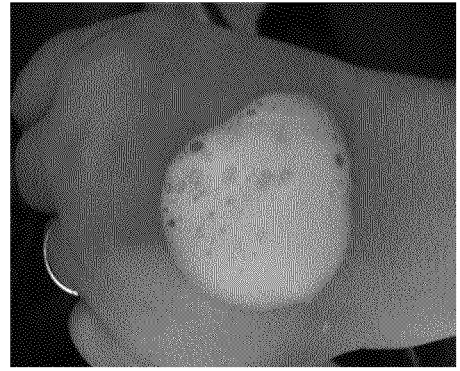
Time =1 minute
Time = 2 minute
Time = 0 hour after being rubbed
Time = 2 minutes after being rubbed
*FIG. 45*

Foam Collapse for Formulation P100310-05 after being dispensed with Rexam M3 Foamer and after being rubbed on application site
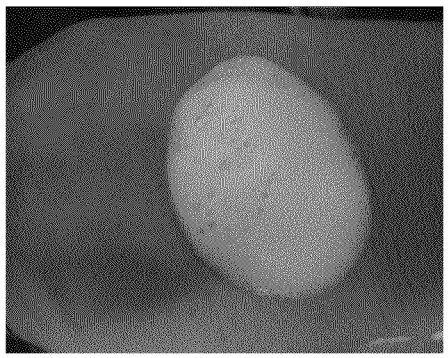
Time = 0 hour
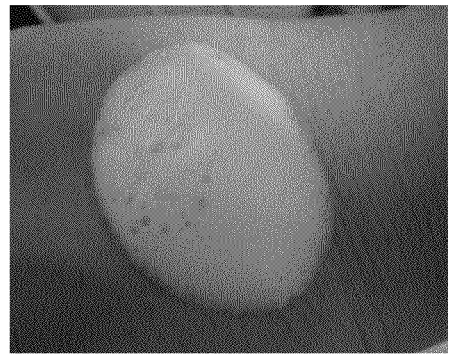
Time = 1 minute
Time = 2 minutes
Time = 0 hour after being rubbed
Time = 2 minutes after being rubbed
*FIG. 46*

Foam Collapse for Formulation P100310-06 after being dispensed with Rexam M3 Foamer and after being rubbed on application site
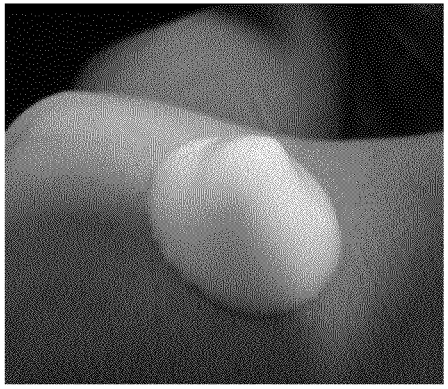
Time = 0 hour
Time = 1 minute
Time = 2 minutes
Time = 0 hour after being rubbed
Time = 1 minute after being rubbed
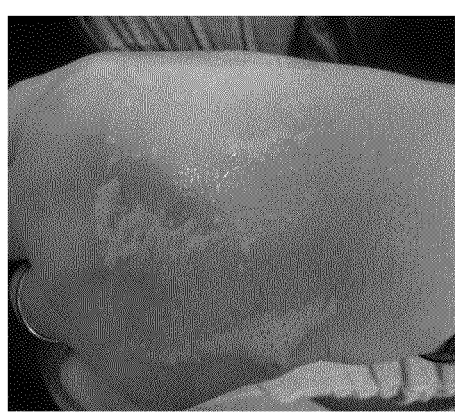
Time = 2 minutes after being rubbed
*FIG. 47*

Foam Collapse for Formulation P100310-07 after being dispensed with Rexam M3 Foamer and after being rubbed on application site
Time = 0 hour
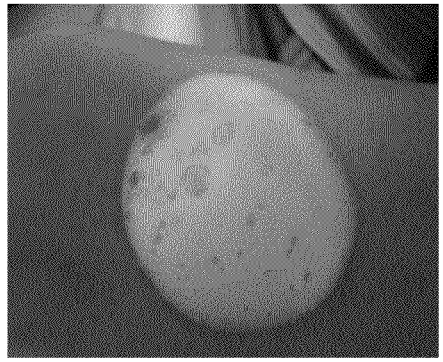
Time = 1 minute
Time = 2 minute
Time = 0 hour after being rubbed
Time = 2 minutes after being rubbed
*FIG. 48*

Foam Collapse for Formulation P100310-08 after being dispensed with Rexam M3 Foamer and after being rubbed on application site
Time = 0 hour
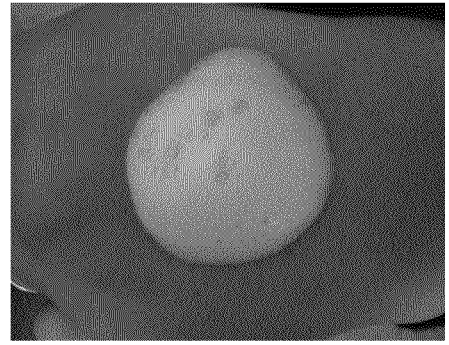
Time = 1 minute
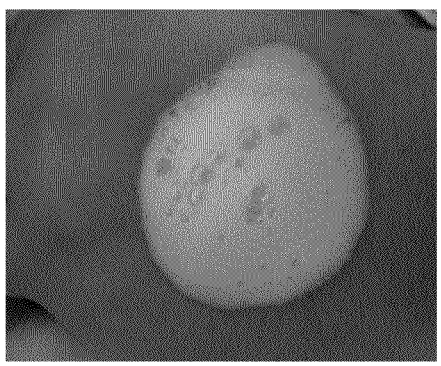
Time = 2 minutes
Time = 0 hour after being rubbed
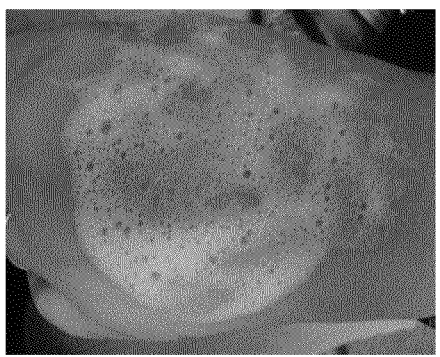
Time = 2 minutes after being rubbed
*FIG. 49*

Foam Collapse for Formulation P100310-09 after being dispensed with Rexam M3 Foamer and after being rubbed on application site
Time = 0 hour
Time = 1 minute
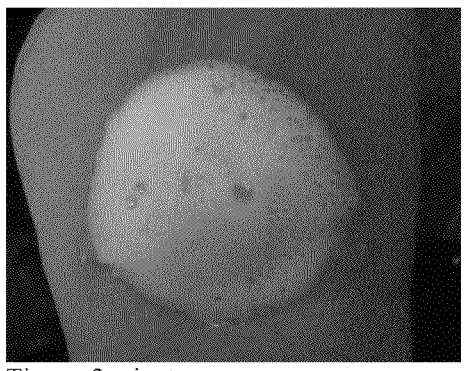
Time = 2 minutes
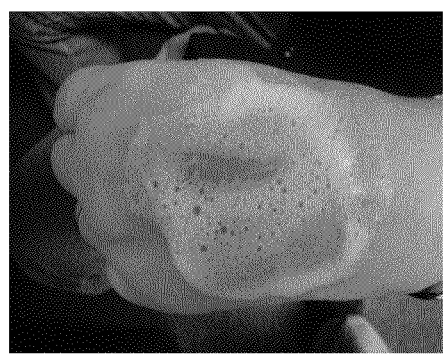
Time = 0 hour after being rubbed
Time = 1 minute after being rubbed
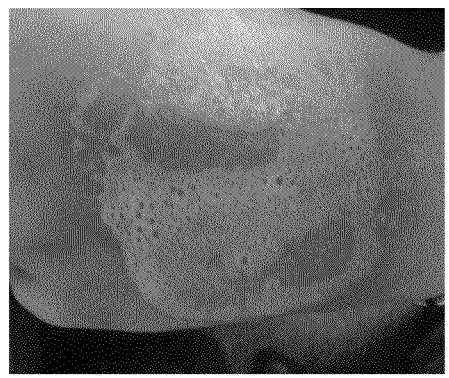
Time = 2 minutes after being rubbed
*FIG. 50*

Foam Collapse for Formulation P100312-01 after being dispensed with Rexam M3 Foamer and after being rubbed on the application site
Time = 0 hour
Time = 1 minute
Time = 2 minute
Time = 0 hour after being rubbed
Time = 1 minute after being rubbed
Time = 2 minutes after being rubbed
*FIG. 51*

Foam Collapse for Formulation P100312-03 after being dispensed with Rexam M3 Foamer and after being rubbed on the application site
Time = 0 hour
Time = 1 minute
Time = 2 minutes
Time = 0 hour after being rubbed
Time = 1 minute after being rubbed
Time = 2 minutes after being rubbed
*FIG. 52*

Foam Collapse for Formulation P100312-04 after being dispensed with Rexam M3 Foamer and after being rubbed on the application site
Time = 0 hour
Time = 1 minute
Time = 2 minutes
Time = 0 hour after being rubbed
Time = 1 minute after being rubbed
Time = 2 minutes after being rubbed
*FIG. 53*

Foam Collapse for Formulation P100312-05 after being dispensed with Rexam M3 Foamer and after being rubbed on the application site
Time = 0 hour
Time = 1 minute
Time = 2 minutes
Time = 0 hour after being rubbed
Time = 1 minute after being rubbed
Time = 2 minutes after being rubbed
*FIG. 54*

Foam Collapse for Formulation P100312-06 after being dispensed with Rexam M3 Foamer and after being rubbed on the application site
Time = 0 hour
Time = 1 minute
Time = 2 minutes
Time = 0 hour after being rubbed
Time = 1 minute after being rubbed
Time = 2 minutes after being rubbed.
*FIG. 55*

Formulation no. 1

Formulation no. 2

Formulation no. 3

Formulation no. 4

Formulation no. 5

Formulation no. 6

Formulation no. 7

Formulation no. 8

Formulation no. 9

Formulation no. 10

Formulation no. 11

Formulation no. 12

Formulation no. 13

Formulation no. 14

Formulation no. 15

FOAMABLE FORMULATION

CROSS-REFERENCE TO RELATED APPLICATIONS

This application is a continuation of International Patent Application PCT/US11/28004 (filed Mar. 10, 2011), which claims the benefit of U.S. Provisional Application No. 61/312,629 (filed Mar. 10, 2010). The contents of these priority documents and all other references disclosed herein are incorporated in their entirety for all purposes.

BACKGROUND OF THE INVENTION

A foam is a multiphase mixture comprising bubbles of a gas phase that are separated by a liquid or solid layer (a film). Pilpel N., Foams in pharmacy, *Endeavour* 9: 87-91 (1985); Durian, D. J. and Weitz, D. A., "Foams" in *Kirk-Othmer Encyclo. Chem. Tech.*, 4th ed., 11: 783-805 (1994). Liquid-based foams are dynamic systems that eventually collapse or break to release the gas phase. A foam's collapsibility or breakability depends on numerous physical properties of its components, such as the liquid phase's viscosity and surface tension, the gas phase's pressure and bubble size, and the film's elasticity.

To persist for more than a short period, a foam preferably includes at least one foaming agent such as a protein or surfactant. Surfactants stabilize the foam, e.g., by inhibiting bubble coalescence. Zhao, Y.; Brown, M. B.; Jones, S. J., Pharmaceutical foams: are they the answer to the dilemma of topical nanoparticles?, *Nanomedicine*, in press (2010).

As discussed in WO2009/090558, the types of topical foam vehicles include aqueous foams, such as commonly available shaving foams; hydroalcoholic foams; emulsion-based foams, comprising oil and water components; and oleaginous foams, which comprise high levels of oil. Lower alcohol compounds may increase penetration, but may also dry the skin and may cause stinging if applied to wounds or sores. Oily components may be emollients, moistening the skin, but may also leave an unpleasant greasy residue.

Some foams are long-lasting (e.g., shaving creams or gels). Other foams are quick-breaking and collapse soon after application, which can allow more rapid absorption of the foam's active agent. However, if the foam breaks too quickly, it will be difficult to apply. Quick-breaking foams may be destabilized by body heat (thermolabile) or by force (labile to mechanical stress), which allows easy spreading over the site of application.

Mere combination of basic ingredients does not automatically produce foams suitable for pharmaceutical or cosmetic use. Small changes in the foam base, such as the addition of active ingredients or co-solvents, may destabilize a foam. Similarly, selection within a group of ingredients may provide a foam or class of foams that provides unpredictably superior properties.

For example, DMSO is a polar aprotic solvent with lower surface tension than water. DMSO has penetration-enhancing properties that make it an attractive as a solvent, but it is difficult to foam. A DMSO-based foam would likely provide improved penetration of its active ingredient in addition to the other advantages of a foam.

Although a foam's properties can be difficult to predict, properties such as collapsibility or stiffness are crucial for the foam's intended use. For example, a pharmaceutical foam for internal application must sometimes persist for hours or days to release an active agent slowly. A pharmaceutical foam for topical application to skin must break down more quickly, but not so quickly that the liquid or solid phase will drip off the skin before absorption of sufficient active agent.

Qualities such as foam stability, easiness to spread, and appropriate breakability upon application to the skin or joint are desirable features. These characteristics can be measured by conducting foam formation and foam collapsibility experiments. Foam formation (foam height vs. time), for example, is predictive of the generation of a sprayable/spreadable foam. The rate of collapsibility is an important property in the appropriate administration of the foam.

Many foams are generated by dispensing a foam base in combination with a dissolved, gaseous propellant that expands upon release from a container to produce the foam's bubbles (e.g., those disclosed in WO 2010/125470). However, propellant-based foams take longer to collapse as compared to quick-breaking aqueous foams and as such may not be useful in certain applications. Manufacturing a propellant-based composition can also be more costly and difficult, and the associated canisters can harm the environment. Additionally, there is an increased risk in handling and transporting pressurized canisters due to the dangers associated with their explosive properties. It is therefore preferable to develop a composition comprising DMSO that is foamable in the absence of a propellant.

Pharmaceutical foams have been used in wound and burn dressings, contraception, and topical drug delivery. They are easy to apply uniformly to skin, less messy than cream or liquid dosage forms, and less irritating to sensitive or abraded skin. Zhao, Y. et al., Id. The superior properties of foams may enhance patient compliance. The dispensing means of a foam formulation can help to prevent contamination of the container during application. For at least these reasons, foams are attractive dosage forms for topically absorbable active agents.

Osteoarthritis (OA) is a chronic joint disease characterized by progressive degeneration of articular cartilage. Symptoms include joint pain and impaired movement. OA is one of the leading causes of disability worldwide and a major financial burden to health care systems. It is estimated to affect over 15 million adults in the United States alone. See Boh L. E. Osteoarthritis. In: DiPiro J. T., Talbert R. L., Yee G. C., et al., editors. *Pharmacotherapy: a pathophysiological approach.* 4th ed. Norwalk (CT): Appleton & Lange, pp. 1441-59 (1999).

Oral non-steroidal anti-inflammatory drugs (NSAIDs) are a mainstay in the management of OA. Oral NSAIDs are also commonly used in the management of pain associated with injuries such as minor strains, sprains and contusions. These drugs are thought to exert their analgesic effect by impeding the production of signaling molecules called prostaglandins through inhibition of the cyclooxygenase ("COX") enzyme. The COX enzyme has two isoforms, COX-1 and COX-2. Traditional NSAIDs inhibit both isoforms of the COX enzyme, while the selective COX-2 (coxib) class of NSAIDs preferentially inhibits COX-2.

NSAIDs have analgesic, anti-inflammatory, and antipyretic effects and are useful in reducing pain and inflammation. They are, however, associated with serious potential side effects including nausea, vomiting, peptic ulcer disease, and gastrointestinal (GI) hemorrhage. Although selective COX-2 inhibitors produce fewer gastrointestinal side effects, they may increase the risk of thrombotic events (e.g., stroke or heart attack). Because of this potential side effect, most of the selective COX-2 inhibitors have been withdrawn from the market.

Topical NSAIDs offer the possibility of achieving local therapeutic benefit while reducing or eliminating the risk of systemic side effects. Difficulties in topical NSAID treatment of OA or minor injuries partially arise from the difficulty associated with delivering a therapeutically effective dose of the NSAID through the skin in a manner that makes the treatment itself tolerable. It is generally believed that clinical efficacy in OA requires absorption of the active ingredient and its penetration in sufficient quantities into underlying inflamed tissues including the synovium and synovial fluid of joints. See Rosenstein, Topical agents in the treatment of rheumatic disorders, *Rheum. Dis. Clin North Am.*, 25: 899-918 (1999).

Various factors can affect the absorption rates and penetration depth of topical pharmaceutical preparations, including the nature of the active ingredient, the nature of the vehicle, the pH, and the relative solubility of the active in the vehicle versus the skin (Ostrenga J. et al., Significance of vehicle composition I: relationship between topical vehicle composition, skin penetrability, and clinical efficacy, *Journal of Pharmaceutical Sciences*, 60: 1175-1179 (1971)). More specifically, drug attributes such as solubility, size and charge, as well as vehicle attributes such as the drug dissolution rate, spreadability, adhesion, and ability to alter the membrane permeability can each have significant effects on permeability. The skin barrier also can be compromised by physical methods, such as iontophoresis, ultrasound, electroporation, heat, and microneedles.

Topical NSAIDs take various forms such as liquids, gels, ointments and salves. Pharmaceutical foams are formed from the dispersion of a gas phase in a second immiscible liquid or solid phase. Pharmaceutical foams have been used in wound and burn dressings, contraception and topical skin delivery. The collapsibility or breakability of a pharmaceutical foam is often unpredictable and follows no particular theory. However, the feature of collapsibility or stiffness of a foam is crucial for many uses.

In light of the foregoing, there is a need for a topical DMSO foam formulation such as a topical NSAID foam suitable for long-term use in the treatment of OA. A diclofenac or ibuprofen foam would be especially useful. The challenge has been to develop a formulation that will deliver the active agent to the underlying tissue in sufficient concentration to treat a disorder, possibly on a long-term basis, while still providing a foam with an appropriate collapsibility or breakability. The present invention satisfies these and other needs.

BRIEF SUMMARY OF THE INVENTION

The present invention relates generally to foamable formulations and methods of using the foamable formulations to treat pain. In a preferred embodiment, the foamable formulation comprises dimethyl sulfoxide (DMSO) and an active agent. More preferably, the active agent is a non-steroidal anti-inflammatory drug (NSAID) such as diclofenac sodium or ibuprofen. In another preferred embodiment, the method of treatment is directed to pain associated with OA or minor injuries.

In one embodiment, the invention provides a foamable formulation, the formulation comprising, consisting essentially of, or consisting of: (i) DMSO; (ii) an active agent; (iii) a monohydric lower alcohol; (iv) a diol; (v) a polyalkylene glycol alkyl ether; and (vi) water. Optionally, the formulation comprises glycerol.

Alternatively, the invention provides a foamable formulation, the formulation comprising: (i) DMSO; (ii) an active agent; and (iii) a polyalkylene glycol alkyl ether. Preferably, the formulation additionally comprises (iv) a diol; and (v) water. Optionally, the formulation comprises glycerol. Preferably, the formulation additionally comprises a monohydric lower alcohol (e.g., ethanol).

In a first aspect, the formulation is propellant-free. Preferably, the formulation is foamable by manual aeration.

In a second aspect, the foamable formulation comprises at least 15% w/w DMSO. Preferably, the formulation comprises at least 25% w/w DMSO. Preferably, the formulation comprises at least 40% w/w DMSO. Preferably, the formulation comprises about 45% w/w DMSO.

In a third aspect, the active agent is a non-steroidal anti-inflammatory drug. Preferably, the non-steroidal anti-inflammatory drug is a diclofenac salt. More preferably, the diclofenac salt is diclofenac sodium. Preferably, the non-steroidal anti-inflammatory drug is ibuprofen.

In a fourth aspect, the active agent is diclofenac sodium (or, alternatively, ibuprofen) and is present at 1-10% w/w; DMSO is present at 5-80% w/w; the monohydric lower alcohol is present at 0-50% w/w; the diol is present at 1-15% w/w; the polyalkylene glycol alkyl ether is present at up to 10% w/w; and q.s. water. Preferably, the polyalkylene glycol alkyl ether is present at up to 5% w/w. More preferably, the polyalkylene glycol alkyl ether is present at up to 2% w/w. Preferably, the monohydric lower alcohol is present at 1-50% w/w.

Alternatively, diclofenac sodium is present at a concentration selected from the group of 1, 1.5, 2 and 3% w/w; DMSO is present at a concentration selected from the group of 42, 43, 44, 45, 45.5, 46, 47, 48% w/w, and fractions between; the monohydric lower alcohol is present at 23-29% w/w; the diol is present at a concentration selected from the group of 9, 10, 11, 12, 13% w/w and fractions between; the polyalkylene glycol alkyl ether is present at up to 2% w/w; and q.s. water.

Alternatively, ibuprofen is present at a concentration selected from the group of 3, 4, 5, 6, 7, and 8% w/w; DMSO is present at a concentration selected from the group of 14, 16, 18, 20, 22, 24, 26, 28 and 30% w/w and percentages between; the monohydric lower alcohol is present at 0, 1, 3, 5, 7, 9, 11, 13, 15, and 17% w/w; the diol is present at a concentration selected from the group of 5, 6, 7, 8, and 9% w/w and fractions between; the polyalkylene glycol alkyl ether is present at up to 3% w/w; and q.s. water.

In a fifth aspect, the formulation comprises glycerol or any other suitable polyol. Preferably, the formulation comprises 1-15% w/w glycerol or any other suitable polyol.

In a sixth aspect, the active agent is diclofenac sodium, and the diclofenac sodium degrades by less than 2% over the course of six months. Preferably, the diclofenac sodium degrades by less than 0.04% over the course of six months at room temperature.

Alternatively, the active agent is ibuprofen, and the active agent degrades by less than 0.6% over the course of three months at 25° C. Alternatively, the ibuprofen degrades by less than 2.0% over the course of three months at 24° C.

In a seventh aspect, the foamable formulation has a pH between about 6.0 and 10.0.

In an eighth aspect, the polyalkylene glycol alkyl ether is a polyethylene glycol alkyl ether.

In a ninth aspect, the foamable formulation comprises at most 2% w/w of the polyalkylene glycol alkyl ether.

In a tenth aspect, the foamable formulation comprises a steroid. More preferably, the steroid is cholesterol. Alternatively, the formulation comprises at most 1% w/w of the steroid. Preferably, the formulation comprises at most 0.5% w/w of the steroid. Still more preferably, the formulation comprises at most 0.2% w/w of the steroid. Alternatively, the formulation comprises at most 0.15% w/w of the steroid.

Alternatively, the formulation comprises at most 0.05% w/w of the steroid.

In an eleventh aspect, the foamable formulation comprises a surfactant. Preferably, the surfactant is a salt of an aryl sulfonate, alkyl sulfonate, aryl sulfate, or alkyl sulfate. More preferably, the aryl sulfonate salt is sodium dodecyl benzene sulfonate, and the alkyl sulfate salt is sodium laureth sulfate or sodium lauryl sulphate. Alternatively, the surfactant is selected from the group of a polyalkylene glycol, a polyalkylene glycol copolymer, and a phospholipid.

Preferably, the foamable formulation comprises at most 0.5% w/w of the surfactant. Still more preferably, the formulation comprises at most 0.2% w/w of the surfactant. Alternatively, the formulation comprises at most 0.15% w/w of the surfactant.

Preferably, the foamable formulation further comprises a pH adjusting agent. More preferably, the pH adjusting agent is sodium carbonate.

In a twelfth aspect, the foamable formulation when foamed does not collapse to a liquid phase for at least 30 seconds at 37° C. or at skin temperature. Preferably, the formulation when foamed does not collapse to a liquid phase for at least 60 seconds at 37° C. or at skin temperature. More preferably, the formulation when foamed does not collapse to a liquid phase for at least two minutes at 37° C. or at skin temperature. Alternatively, the formulation when foamed does not collapse to a liquid phase for at least five minutes at 37° C. or at skin temperature.

In a thirteenth aspect, the foamable formulation when applied topically provides a reduction of pain over 12 weeks. Preferably, the pain is due to osteoarthritis or minor injury. Preferably, the formulation is applied twice daily. Alternatively, the formulation is applied three times daily. Alternatively, the formulation is applied four times daily.

In a fourteenth aspect, the foamable formulation comprises a thickening agent. Preferably, the composition comprises up to 2% (w/w) of the thickening agent. Alternatively, the viscosity of the composition is at most about 1000 centipoise (cP). Preferably, the composition comprises 0.2% w/w of the thickening agent. Still more preferably, the composition comprises 0.1% w/w of the thickening agent. Alternatively, the viscosity of the composition is at most about 100 cP. More preferably, the viscosity is at most about 50 cP.

In a second embodiment, the invention provides a method for treating osteoarthritis or minor injury (e.g., minor strains, sprains, or contusions) in a subject suffering from pain, the method comprising, consisting essentially of, or consisting of the topical administration to an afflicted area of the subject a therapeutically effective amount of a foamable formulation, the formulation comprising: (i) DMSO; (ii) an active agent; and (iii) a polyalkylene glycol alkyl ether. More preferably, the formulation comprises: (i) DMSO; (ii) an active agent; (iii) a monohydric lower alcohol; (iv) a diol; (v) a polyalkylene glycol alkyl ether; and (vi) water. Optionally, the formulation comprises glycerol.

Alternatively, the invention provides a method for treating osteoarthritis or minor injury (e.g., minor strains, sprains, or contusions) in a subject suffering from pain, the method comprising, consisting essentially of, or consisting of the topical administration to an afflicted area of the subject a therapeutically effective amount of a foamable formulation, the formulation comprising: (i) DMSO; (ii) an active agent; and (iii) a polyalkylene glycol alkyl ether. Preferably, the formulation additionally comprises (iv) a diol; and (v) water. Optionally, the formulation comprises glycerol. Preferably, the formulation additionally comprises a monohydric lower alcohol (e.g., ethanol).

In a first aspect of the second embodiment, the formulation is propellant-free. Preferably, the formulation is foamable by manual aeration.

In a second aspect of the second embodiment, the foamable formulation comprises at least 15% w/w DMSO. Preferably, the formulation comprises at least 25% w/w DMSO. Preferably, the formulation comprises at least 40% w/w DMSO. Preferably, the formulation comprises about 45% w/w DMSO.

In a third aspect of the second embodiment, the active agent is a non-steroidal anti-inflammatory drug (NSAID). Preferably, the NSAID is a diclofenac salt. More preferably, the diclofenac salt is diclofenac sodium. Preferably, the NSAID is ibuprofen.

In a fourth aspect of the second embodiment, the active agent is diclofenac sodium (or, alternatively, ibuprofen) and is present at 1-10% w/w; DMSO is present at 5-80% w/w; monohydric lower alcohol is present at 0-50% w/w; the diol is present at 1-15% w/w; the polyalkylene glycol alkyl ether is present at up to 10% w/w; and q.s. water. Preferably, the polyalkylene glycol alkyl ether is present at up to 5% w/w. More preferably, the polyalkylene glycol alkyl ether is present at up to 2% w/w. Preferably, the monohydric lower alcohol is present at 1-50% w/w.

Alternatively, diclofenac sodium is present at a concentration selected from the group of 1, 1.5, 2 and 3% w/w; DMSO is present at a concentration selected from the group of 42, 43, 44, 45, 45.5, 46, 47, 48% w/w and fractions between; the monohydric lower alcohol is present at 23-29% w/w; the diol is present at a concentration selected from the group of 9, 10, 11, 12, 13% w/w and fractions between; the polyalkylene glycol alkyl ether is present at up to 2% w/w; and q.s. water.

Alternatively, ibuprofen is present at a concentration selected from the group of 3, 4, 5, 6, 7, and 8% w/w; DMSO is present at a concentration selected from the group of 14, 16, 18, 20, 22, 24, 26, 28 and 30% w/w and percentages between; the monohydric lower alcohol is present at 0, 1, 3, 5, 7, 9, 11, 13, 15 and 17% w/w; the diol is present at a concentration selected from the group of 5, 6, 7, 8, and 9% w/w and fractions between; the polyalkylene glycol alkyl ether is present at up to 3% w/w; and q.s. water.

In a fifth aspect of the second embodiment, the formulation comprises 1-15% w/w glycerol or any other suitable polyol.

In a sixth aspect of the second embodiment, the active agent is diclofenac sodium, and the diclofenac sodium degrades by less than 2% over the course of six months. Preferably, the diclofenac sodium degrades by less than 0.04% over the course of six months at room temperature.

Alternatively, the active agent is ibuprofen, and the active agent degrades by less than 0.6% over the course of three months at 25° C. Alternatively, the ibuprofen degrades by less than 2.0% over the course of three months at 24° C.

In a seventh aspect of the second embodiment, the foamable formulation has a pH between about 6.0 and 10.0.

In an eighth aspect of the second embodiment, the polyalkylene glycol alkyl ether is a polyethylene glycol alkyl ether.

In a ninth aspect of the second embodiment, the foamable formulation comprises at most 2% w/w of the polyalkylene glycol alkyl ether.

In a tenth aspect of the second embodiment, the foamable formulation comprises a steroid. More preferably, the steroid is cholesterol. Alternatively, the formulation comprises at most 1% w/w of the steroid. Preferably, the formulation comprises at most 0.5% w/w of the steroid. Still more preferably, the formulation comprises at most 0.2% w/w of the steroid. Alternatively, the formulation comprises at most 0.15% w/w of the steroid. Alternatively, the formulation comprises at most 0.05% w/w of the steroid.

In an eleventh aspect of the second embodiment, the foamable formulation comprises a surfactant. Preferably, the surfactant is a salt of an aryl sulfonate, alkyl sulfonate, aryl sulfate, or alkyl sulfate. More preferably, the aryl sulfonate salt is sodium dodecyl benzene sulfonate, and the alkyl sulfate is sodium laureth sulfate or sodium lauryl sulfate. Alternatively, the surfactant is selected from the group of a polyalkylene glycol, a polyalkylene glycol copolymer, and a phospholipid.

Preferably, the foamable formulation comprises at most 0.5% w/w of the surfactant. Still more preferably, the formulation comprises at most 0.2% w/w of the surfactant. Alternatively, the formulation comprises at most 0.15% w/w of the surfactant.

Preferably, the foamable formulation further comprises a pH adjusting agent. More preferably, the pH adjusting agent is sodium carbonate.

In an twelfth aspect of the second embodiment, the foamable formulation when foamed does not collapse to a liquid phase for at least 30 seconds at 37° C. or at skin temperature. Preferably, the formulation when foamed does not collapse to a liquid phase for at least 60 seconds at 37° C. or at skin temperature. More preferably, the formulation when foamed does not collapse to a liquid phase for at least two minutes at 37° C. or at skin temperature. Alternatively, the formulation when foamed does not collapse to a liquid phase for at least five minutes at 37° C. or at skin temperature.

In a thirteenth aspect of the second embodiment, the foamable formulation when applied topically provides a reduction of pain over 12 weeks. Preferably, the formulation is applied twice daily. Alternatively, the formulation is applied three times daily. Alternatively, the formulation is applied four times daily.

In a fourteenth aspect of the second embodiment, the foamable formulation comprises a thickening agent. Preferably, the composition comprises up to 2% (w/w) of the thickening agent. Alternatively, the viscosity of the composition is at most about 1000 centipoise (cP). Preferably, the composition comprises 0.2% w/w of the thickening agent. Still more preferably, the composition comprises 0.1% w/w of the thickening agent. Alternatively, the viscosity of the composition is at most about 100 cP. More preferably, the viscosity is at most about 50 cP.

In a third embodiment, the invention provides a dispenser comprising a reservoir operably linked (e.g., in fluid communication) with a release assembly, wherein the reservoir contains a foamable formulation as previously described, and wherein the release assembly allows the foamable formulation to be released as a foam. Preferably, the release assembly is a dispensing head. More preferably, the foam dispensed is a quick-breaking foam.

In a fourth embodiment, the invention provides a pressurized container, the container holding a foamable formulation as previously defined and optionally a propellant. Preferably, a release assembly comprising a nozzle or sprayer is operably linked to the container (e.g., a release assembly for dispensing a foam from an aerosol spray can wherein the release assembly is in fluid communication with the spray can), wherein the release assembly allows the foamable formulation and optionally a propellant to be released as a foam.

In a fifth embodiment, the present invention provides a method for manually foaming a formulation, the method comprising the steps of:
(i) providing a dispenser comprising a reservoir operably linked (e.g., in fluid communication) with a release assembly (e.g., dispensing head),
(ii) filling the reservoir with a foamable formulation as previously described, and
(iii) actuating the release assembly to manaully aerate the formulation, thereby releasing a foam from the release assembly.

Preferably, the release assembly is a dispensing head that is a pump head. Preferably the foam is a quick-breaking foam.

In a sixth embodiment, the present invention provides a topical foam prepared according the previously described method.

In a seventh embodiment, the present invention provides use of a foamable formulation in the manufacture of a medicament for the treatment of pain wherein the formulation comprises:
(i) dimethyl sulfoxide (DMSO);
(ii) an active agent; and
(iii) a polyalkylene glycol alkyl ether.

These and other objects, aspects, and embodiments will become more apparent when read with the following detailed description and drawings.

BRIEF DESCRIPTION OF THE DRAWINGS

FIG. 1 illustrates foams produced by manual shaking of the Example 3 formulations (Table 3). The picture was taken immediately after manual shaking for 30 sec.

FIG. 2 illustrates foams produced by manual shaking of the Example 3 formulations (Table 3). The picture was taken 2 minutes after manual shaking for 30 sec.

FIG. 3 illustrates foams produced by manual shaking of the Example 3 formulations (Table 3). The picture was taken 5 minutes after manual shaking for 30 sec.

FIG. 4 illustrates foams produced by manual shaking of the Example 3 formulations (Table 3). The picture was taken 35 minutes after manual shaking for 30 sec.

FIG. 5 illustrates foams produced by manual shaking of the Example 3 formulations (Table 3). The picture was taken 1 hour after manual shaking for 30 sec.

FIG. 6 illustrates foams produced by manual shaking of the Example 3 formulations (Table 3). The picture was taken 2 hours after manual shaking for 30 sec.

FIG. 7 illustrates foams produced by manual shaking of the Example 3 formulations (Table 3). The picture was taken 3 hours after manual shaking for 30 sec.

FIG. 8 illustrates foams produced by manual shaking of the Example 3 formulations (Table 3). The picture was taken 24 hours after manual shaking for 30 sec.

FIG. 21 illustrates the foam collapsibility of a series of topical formulations (P100223) at 0, 5 and 30 minutes after shaking.

FIG. 39 illustrates general properties of the Rexam M3 foaming head.

FIG. 42 illustrates the foam collapse for formulation P100310-01 after being dispensed from a Rexam M3 foamer and after being rubbed on an application site.

FIG. 43 illustrates the foam collapse for formulation P100310-02 after being dispensed from a Rexam M3 foamer and after being rubbed on an application site.

FIG. 44 illustrates the foam collapse for formulation P100310-03 after being dispensed from a Rexam M3 foamer and after being rubbed on an application site.

FIG. 45 illustrates the foam collapse for formulation P100310-04 after being dispensed from a Rexam M3 foamer and after being rubbed on an application site.

FIG. 46 illustrates the foam collapse for formulation P100310-05 after being dispensed from a Rexam M3 foamer and after being rubbed on an application site.

FIG. 47 illustrates the foam collapse for formulation P100310-06 after being dispensed from a Rexam M3 foamer and after being rubbed on an application site.

FIG. 48 illustrates the foam collapse for formulation P100310-07 after being dispensed from a Rexam M3 foamer and after being rubbed on an application site.

FIG. 49 illustrates the foam collapse for formulation P100310-08 after being dispensed from a Rexam M3 foamer and after being rubbed on an application site.

FIG. 50 illustrates the foam collapse for formulation P100310-09 after being dispensed from a Rexam M3 foamer and after being rubbed on an application site.

FIG. 51 illustrates the foam collapse for formulation P100312-01 after being dispensed from a Rexam M3 foamer and after being rubbed on an application site.

FIG. 52 illustrates the foam collapse for formulation P100312-03 after being dispensed from a Rexam M3 foamer and after being rubbed on an application site.

FIG. 53 illustrates the foam collapse for formulation P100312-04 after being dispensed from a Rexam M3 foamer and after being rubbed on an application site.

FIG. 54 illustrates the foam collapse for formulation P100312-05 after being dispensed from a Rexam M3 foamer and after being rubbed on an application site.

FIG. 55 illustrates the foam collapse for formulation P100312-06 after being dispensed from a Rexam M3 foamer and after being rubbed on an application site.

DETAILED DESCRIPTION OF THE INVENTION

I. Definitions of Terms

Figure 9:
FIG. 9 illustrates the foam produced by dispensing Formulation I (Example 3) when sprayed using a hand dispenser. The picture was taken immediately after dispensing the foam.

The terms "a," "an," or "the" as used herein not only includes aspects with one member, but also includes aspects with more than one member. For example, an embodiment including "a cellulosic thickening agent and a lower monohydric alcohol" should be understood to present certain aspects with at least a second cellulosic thickening agents, at least a second lower monohydric alcohol, or both. An embodiment including "an active agent" should be understood to present certain aspects with at least a second active agent, which may be of a different class (e.g., a non-steroidal anti-inflammatory drug with an anti-inflammatory steroid or a local anesthetic).

The term "about" as used herein to modify a numerical value indicates a defined range around that value. If "X" were the value, "about X" would generally indicate a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X." When the quantity "X" only includes whole-integer values (e.g., "X carbons"), "about X" indicates from (X−1) to (X+1). In this case, "about X" as used herein specifically indicates at least the values X, X−1, and X+1.

When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11%" is equivalent to "about 7%, about 9%, or about 11%."

In compositions comprising an "additional" or "second" component, the second component as used herein is chemically different from the other components or first component. A "third" component is different from the other, first, and second components, and further enumerated or "additional" components are similarly different.

"Agent" as used herein indicates a compound or mixture of compounds that, when added to a pharmaceutical composition, tend to produce a particular effect on the composition's properties. For example, a composition comprising a thickening agent is likely to be more viscous than an otherwise identical comparative composition that lacks the thickening agent.

As used herein, the phrase "effective amount" or "effective dose" means an amount sufficient to achieve the desired result and accordingly will depend on the ingredient and its desired result. Nonetheless, once the desired effect is known, determining the effective amount is within the skill of a person skilled in the art.

"Enhancement ratio" ("ER") as used herein is the ratio of a test result (e.g., ug/cm$^2$ accumulated dose of product) from a formulation comprising an active to the corresponding test result from a control composition comprising the same active at the same concentration in the formulation.

In general, the "error bars" on the graphs represent the standard error of the mean value, whereas the top of the solid, shaded bar represents a single data value, which is the mean value of the distribution of data values.

"Finite dosing" as used herein generally includes an application of a limited reservoir of an active agent. The active agent in the reservoir is depleted with time, leading to a decrease of the absorption rate after a maximum rate is reached.

"Formulation," "pharmaceutical composition," and "composition" as used interchangeably herein are equivalent terms referring to a composition of matter for pharmaceutical use.

"Monohydric alcohol" as used herein includes straight- or branched-chain alkyl alcohols with a single hydroxyl group. Representative monohydric alcohols include methanol, ethanol, n-propanol, isopropanol, n-butanol, t-butanol, n-pentanol, 3-pentanol, 2-methoxyethanol, 2-(2-ethoxyethoxy) ethanol, olelyl alcohol, and the like.

The term "or" as used herein should in general be construed non-exclusively. For example, an embodiment of "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

"Penetration enhancer", "molecular penetration enhancer" or "MPE™" as used herein includes an agent or a combination of agents that improves the transport of molecules such as a pharmaceutically or cosmetically active agent into or through a natural membrane such as skin or nail. Various conditions may occur at different sites in the body, either in the skin or below the skin, creating a need to target delivery of compounds. For example, in a treatment for osteoarthritis, delivery of the active agent to the underlying tissues surrounding the joint may be necessary to achieve therapeutic benefit. A molecular penetration enhancer may be used to assist in the delivery of an active agent i) directly into the skin or nail; ii) locally, or regionally, into tissue(s) underlying the skin or nail; or iii) indirectly via systemic distribution to the site of the disease. If systemic distribution of an active agent (e.g., ibuprofen) would be likely to produce side effects, a molecular penetration enhancer is preferably selected to maximize direct delivery and to minimize systemic distribution. A molecular penetration enhancer may be a pure substance or may comprise, consist essentially of, or consist of a mixture of different chemical entities.

The term "pH adjusting agent" as used herein refers to a compound added to the compositions of the present application for the purpose of changing the pH of the composition. Examples of such agents include pharmaceutically acceptable acids, pharmaceutically acceptable bases, and pharmaceutically acceptable buffers.

The term "pharmaceutically acceptable" means compatible with the treatment of animals, and in particular, humans.

The term "pharmaceutically acceptable salt" means a pharmaceutically acceptable acid addition salt or a pharmaceutically acceptable basic addition salt. The formation of a desired compound salt is achieved using standard techniques. For example, the neutral compound is treated with an acid or base in a suitable solvent and the formed salt is isolated by filtration, extraction, or any other suitable method.

The term "subject" as used herein includes all members of the animal kingdom, preferably mammals, and most preferably, humans.

"Surfactant" as used herein includes a surface-active agent. Surfactants reduce the surface tension of a solvent in which they are dissolved.

"Thickening agent" as used herein includes an agent or combination of agents that increases the viscosity of a composition. A thickening agent may be a pure substance, or it may comprise, consist essentially of, or consist of a mixture of different chemical entities. Exemplary thickening agents include cellulose polymers, carbomer polymers, carbomer derivatives, cellulose derivatives, polyvinyl alcohol, poloxamers, polysaccharides, and the like, as well as mixtures thereof.

"Topical formulation" as used herein includes a composition that is suitable for topical application to the skin, a nail, or a mucosa. A topical formulation may, for example, be used to confer a therapeutic or cosmetic benefit to its user. Specific topical formulations can be used for local, regional, or transdermal application of substances.

"Transdermal" as used herein includes a process that occurs through the skin. The terms "transdermal," "percutaneous," and "transcutaneous" can be used interchangeably. In certain embodiments, "transdermal" may also include epicutaneous.

"Transdermal application" as used herein includes administration through the skin. Transdermal application can be used for systemic delivery of an active agent; however, it is also useful for delivery of an active agent to tissues underlying the skin with minimal systemic absorption. In certain embodiments, "transdermal application" may also include epicutaneous application.

The term "treating" or "treatment" as used herein (and as well understood in the art) means an approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable.

"Treating" and "treatment" as used herein also include prophylactic treatment. Treatment methods comprise administering to a subject a therapeutically effective amount of an active agent. The administering step may consist of a single administration or may comprise a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The prefix "micro" as used herein can be alternatively abbreviated as "µ" or "u." For example, micrograms are typically abbreviated as µg, but can alternatively be abbreviated as "ug."

The term "w/w" or "wt/wt" means a percentage expressed in terms of the weight of the ingredient or agent over the total weight of the composition multiplied by 100.

II. Embodiments

A. Active Agent

In one preferred aspect, the active agent is an anti-inflammatory agent. More preferably, the agent is a non-steroidal anti-inflammatory drug (NSAID). Preferably, the agent is a diclofenac salt. More preferably, the diclofenac salt is diclofenac sodium. An embodiment including "an active agent" should be understood to present certain aspects with at least a second active agent, which may be the same class or a different class (e.g., a non-steroidal anti-inflammatory drug with an anti-inflammatory steroid or a local anesthetic).

Non-limiting examples of NSAIDs include acetic acid derivatives such as indomethacin, sulindac, etodolac, and diclofenac; propionic acid derivatives such as ibuprofen, naproxen, fenoprofen, ketoprofen, fluriprofen, and oxaprozin; coxibs such as celecoxib, rofecoxib, valdecoxib, parecoxib, lumiracoxib, and etoricoxib; fenamic acid derivatives such as mefenamic acid, meclofenamic acid, flufenamic acid, and tolfenamic acid; enolic acid derivatives such as piroxicam, meloxicam, tenoxicam, droxicam, and isoxicam; and the compounds' pharmaceutically acceptable salts such as diclofenac sodium, naproxen sodium, and diclofenac potassium. Acetic acid derivatives, coxibs, and their pharmaceutically acceptable salts are preferred.

Other NSAIDs include aspirin, salicylic acid, diflunisal, etodolac, nabumetone, salsalate, bromfenac, ketorolac, tolmetin, and their pharmaceutically acceptable salts. Also included are dexibuprofen (i.e., (S)-+-ibuprofen) or ibuprofen that is enantiomerically enriched with the dexibuprofen enantiomer.

B. Dimethyl Sulfoxide (DMSO)

In one preferred aspect, the compositions and formulations include DMSO. The DMSO may be present in an amount of 5% to 80% w/w. Preferably, DMSO is present in an amount ranging from about 5-30% w/w, about 10-40% w/w, about 15-50% w/w, about 20-60% w/w, about 25-70% w/w, or about 30-80% w/w. Alternatively, a clinically effective amount of DMSO may range from 5% to 60% w/w. Preferably, DMSO is present in an amount of at least 15% w/w. More preferably, DMSO is present in an amount of at least 25% w/w. Still more preferably, DMSO is present in an amount of at least 45% w/w. In a particular embodiment of the invention, DMSO is used at a concentration of about 12 to 48% w/w. Preferably, DMSO is used at a concentration such as 42, 43, 44, 45, 45, 46, 47 and 48% w/w as well as all fractions between such as 42.5, 43.5 44.5, 45.5, and the like. Alternatively, DMSO is used at a concentration such as 14, 16, 18, 20, 22, 24, 26, 28 and 30% w/w as well as all percentages between.

DMSO is a polar aprotic solvent characterized as having low surface tension. Producing a foamable formulation comprising DMSO (or high concentration DMSO liquids) is difficult, requiring extensive experimentation and analyses. As discussed below, the constituents required to achieve a foamable formulation are not readily discernable. In fact, the majority of compounds tested had less than desirable qualities for producing a foamable DMSO-containing formulation. Despite this, polyethylene glycol alkyl ethers (e.g., Brij 30, Brij 78, Brij 90, Brij 98, and the like) provided surprisingly good results. In addition, altering the ratio of DMSO to ethanol improved foam quality. Best foams were produced at a ratio of 0:70 to 20:60 (EtOH:DMSO).

C. Lower Alcohols and Diols

In one preferred aspect, the compositions and formulations include a lower alcohol. More preferably, the lower alcohol is a monohydric lower alcohol, and still more preferably, the lower alcohol is selected from a $C_1$ to $C_6$ alkanol, such as methanol, ethanol, propanol, isopropanol, butanol, isobutanol, sec-butanol, pentanol, and the like, as well as a mixture thereof. Ethanol is preferred.

In certain aspects the composition includes about 0% to 60% (w/w) or about 1 to 50% (w/w) of the lower alcohol (e.g., ethanol). In other aspects, the formulations include about 5, 10, 15, 20, 22, 23, 25, 30 32, 33, 35, 36, 40, 41, 42, 45, 50, 55, or 60% (w/w) of a lower alcohol. More preferably, the composition comprises from about 5% to 25% (w/w) of a lower alcohol, such as about 5, 6, 7, 8, 9, 10, 11, 11.2, 12, 13, 15, 18, 20, 22, 23, or 25%. Alternatively, the composition comprises from about 1 to 5%, about 1 to 12%, about 5 to 15%, about 5 to 22.5%, about 10 to 23%, about 15 to 30%, about 20 to 40%, about 25 to 50%, about 35 to 50%, about 35 to 60% (w/w) of a lower alcohol. Alternatively, the composition comprises about 22, 22.5, 23, 25, 30, 32, 32.5, 33, 35, 35.5, 36, 39, 39.5, 40, 41, 41.7, 42, or 50% (w/w) of a lower alcohol.

In another aspect, the formulations include a diol. Suitable diols include, but are not limited to, propylene glycol, butanediol, butynediol, pentanediol, hexanediol, octanediol, neopentyl glycol, 2-methyl-1,3-propanediol, diethylene glycol, triethylene glycol, tetraethylene glycol, dipropylene glycol, dibutylene glycol, propylene glycol, and the like, as well as a mixture thereof. In one aspect, the formulation comprises about 0% to 15% (w/w) of propylene glycol, and preferably about 0 to 8%. In certain preferred aspects, the diol is a glycol, such as ethylene glycol, propylene glycol, or a mixture thereof. More preferably, the diol is propylene glycol.

In still another aspect, the formulation includes at least two alcohols. Preferably, the formulation includes a monohydric alcohol and a diol. More preferably, the monohydric alcohol is ethanol. Alternatively, the diol is propylene glycol. Still more preferably, the monohydric alcohol is ethanol, and the diol is propylene glycol.

D. Polyalkylene Glycol Alkyl Ether

In one preferred aspect, the composition includes at least one pharmaceutically acceptable surfactant that is a polyalkylene glycol alkyl ether. The polyalkylene glycol alkyl ether may be present at up to about 5% w/w, such as about 0.1, 0.15, 0.2, 0.3, 0.4, 0.5, 1.0, 1.5, 2, 2.5, 3, 3.5, 4, 4.5 or 5% w/w. More preferably, the polyalkylene glycol alkyl ether is present at up to about 3% w/w, such as about 0.1, 0.15, 0.2, 0.3, 0.4, 0.5, 1.0, 1.25, 1.5, 1.75, 2.0; 2.25, 2.5, 2.75 or 3% w/w.

Preferably, the composition includes a polyalkyene glycol alkyl ether; more preferably, a polyalkylene glycol alkyl ether such as a polypropylene oxide alkyl ether or a polyethylene glycol alkyl ether. Some non-limiting examples of polyalkylene glycol alkyl ethers include poly(oxyethylene) cetyl ether, poly(oxyethylene) palmityl ether, polyethylene oxide hexadecyl ether, polyethylene glycol cetyl ether, Brij 30, Brij 38, Brij 52, Brij 56, Brij 58, Brij 78, Brij 98, Brij 700, Brij 700P, Brij 721, and Brij W1. Preferably, the polyalkylene glycol alkyl ether is a combination of Brij 30 and Brij 78. The Brij group of non-ionic surfactants are particularly preferred for their surprising effectiveness at producing foams from formulations including large proportions of DMSO. Further, these surfactants are particularly effective in producing a foamable formulation in the absence of a propellant.

Other non-limiting examples include members of the class of alkyl ether nonionic surfactants with two to 100 alkylene glycol repeat units in their polyalkylene glycol polymeric chains. Preferably, the alkyl group is derived from a fatty acid alcohol. Preferably, the polyalkenene glycol is polyethylene glycol.

The composition may include a polyalkylene glycol block co-polymer such as Poloxamer 188 or Poloxamer 407. Alternatively, the formulation includes a phospholipid. These components may be preferred for use with a foamable formulation that requires use of a propellant, such as octane, butane or isopentane, for conversion to a foam or for stability of the resulting foam.

D. Surfactants

In one aspect, the composition may include one or more additional nonionic, cationic, anionic, and/or zwitterionic surfactants. The one or more surfactants may be present at about 0.1% or 0.15% to 10% w/w, such as about 0.1, 0.15, 0.2, 0.3, 0.4, 0.5, 1.0, 1.5, 2, 3, 4, 5, 6, 7, 8, 9 or 10% w/w.

1. Nonionic Surfactants

Non-limiting examples of nonionic surfactants include polysorbates, such as polysorbate 20 (Tween 20), Tween 40, Tween 60, and Tween 80; poly(oxyethylene) (POE) fatty acid esters, such as Myrj 45, Myrj 49, Myrj 52 and Myrj 59; sucrose esters; partial esters of sorbitol and its anhydrides, such as sorbitan monolaurate; mono or diglycerides; and isoceteth-20.

Other non-limiting examples include members of the class of alkyl ester nonionic surfactants with 8 to 100 alkylene glycol repeat units in their polyalkylene glycol polymeric chains (e.g., 8, 40, 50, or 100). Preferably, the ester group is derived from a fatty acid. Preferably, the polyalkene glycol is polyethylene glycol.

Other nonionic surfactants include, but are not limited to, cetomacrogol 1000, cetostearyl alcohol, cetyl alcohol, cocoamide diethanolamine, cocoamide monoethanolamine, decyl glucoside, glyceryl laurate, lauryl glucoside, polyoxyethylene ethers of fatty acids such as cetyl alcohol or stearyl alcohol, narrow-range ethoxylates, octyl glucoside, oleyl alcohol, poloxamers, polyethylene glycol, sorbitan monolaurate, polyoxyethylene sorbitan monolaurate, sorbitan dioleate, sorbitan trilaurate, sorbitan monopalmitate, polyoxyethylene (20) sorbitan monopalmitate, sorbitan monostearate, sorbitan tristearate, polyoxyethylene (20) sorbitan monostearate, sorbitan monooleate, sorbitan trioleate, polyoxyethylene sorbitan monooleate, stearyl alcohol, sucrose coconut fatty ester mixtures, glycerin monolaurate, and sucrose monolaurate.

Still other non-ionic surfactants include, but are not limited to, fatty acid diesters, polyethylene glycol glycerol fatty acid esters, alcohol-oil transesterification products, polyglycerized fatty acids, sterol and sterol derivatives, polyethylene glycol alkyl ethers, sugar esters, polyethylene glycol alkyl phenols, polyoxyethylene-polyoxypropylene block copolymers, sorbitan fatty acid esters and lower alcohol fatty acid esters.

2. Cationic Surfactants

Non-limiting examples of cationic surfactants include octyl trimethylammonium salts, cetyl trimethyl ammonium salts, stearyl trimethyl ammonium salts, benzyl trimethyl ammonium salts, alkylamines, alkylimidazoles, ethoxylated amines, non-amphoteric quaternary surfactants, esterquats, and a mixture thereof. Quaternary surfactants contain at least one nitrogen atom, which is covalently bonded to four alkyl or aryl groups.

Cationic surfactants include, but are not limited to, non-amphoteric quaternary ammonium compounds, in particular benzyltrialkyl ammonium chlorides or bromides, e.g., benzyl dimethylstearyl ammonium chloride; alkyl trialkyl ammonium salts, e.g., cetyl trimethyl ammonium chloride or bromide, alkyl dimethylhydroxyethyl ammonium chloride or bromide, dialkyl dimethyl ammonium chloride or bromide, and alkylamide ethyltrimethyl ammonium ether sulfates; alkylpyridinium salts, e.g., lauryl or cetyl pyrimidinium chloride; N,N'-dialkylimidazole derivatives; compounds having cationic character, such as amine oxides, e.g., alkyl dimethylamine oxides or alkylaminoethyl dimethylamine oxides; and the like.

3. Anionic Surfactants

Non-limiting examples of anionic surfactants include alkyl sulfates, e.g., sodium, ammonium or triethylammonium (TEA) lauryl sulfate or laureth sulfate; acylamino acids (and their salts), such as acyl glutamates, e.g., sodium acyl glutamate, di-TEA palmitoyl aspartate, and sodium caprylic/capric glutamate; acyl peptides, e.g., palmitoyl-hydrolyzed milk protein, sodium cocoyl-hydrolyzed soya protein and sodium/potassium cocoyl-hydrolyzed collagen; sarcosinates, e.g., myristoyl sarcosin, TEA-lauroyl sarcosinate, sodium lauroyl sarcosinate and sodium cocoyl sarcosinate; taurates, e.g., sodium lauroyl taurate and sodium methylcocoyl taurate; acyl lactylates, lauroyl lactylate, caproyl lactylate; and alaninates; and the like.

Other anionic surfactants include carboxylic acids and derivatives, such as carboxylic acids, e.g., lauric acid, aluminum stearate, magnesium alkanolate, and zinc undecylenate; ester carboxylic acids, e.g., calcium and sodium stearoyl lactylates, laureth-6 citrate, and sodium PEG-4 lauramide carboxylate; ether carboxylic acids, e.g., sodium laureth-13 carboxylate, and sodium PEG-6 cocoamide carboxylate; and the like.

Other anionic surfactants include esters of phosphoric acid and salts, e.g., dilaureth-4 phosphate.

Other anionic surfactants include sulfonic acids and salts, such as acyl isethionate, e.g., sodium-ammoniumcocoyl isethionate, alkylaryl sulfonates; alkyl sulfonates, e.g., sodium coco monoglyceride sulfate, sodium $C_{12-14}$ olefinsulfonate, sodium lauryl sulfoacetate and magnesium PEG-3 cocamide sulfate; sulfosuccinates, e.g., dioctyl sodium sulfosuccinate, disodium laureth sulfosuccinate, disodium lauryl sulfosuccinate, disodium undecylenamido-MEA-sulfosuccinate, and PEG-5 lauryl citrate sulfosuccinate; esters of sulfuric acid, such as alkyl ether sulfate, e.g., sodium, ammonium, magnesium, MIPA, TIPA, laureth sulfate, lauryl sulfate, sodium myreth sulfate and sodium $C_{12-13}$ pareth sulfate; and the like.

4. Zwitterionic Surfactants

In one aspect, the composition comprises a zwitterionic surfactant or a charged derivative thereof. In one aspect, the zwitterionic surfactant or charged derivative thereof is selected from the group of disodium cocoamphodiacetate, sodium cocoamphodiacetate, cocoamidopropyl betaine, and a mixture thereof.

Other zwitterionic surfactants or charged derivatives thereof include, but are not limited to, amino acids such as β-N-alkylaminopropionic acids, aminopropyl alkylglutamide, alkylaminopropionic acid, sodium alkylimidodipropionate, dihydroxyethyl alkyl glycinate, and lauroamphocarboxyglycinate; imino acids such as N-alkyl-β-iminodipropionic acids; imidazoline derivatives that are not N,N'-dialkylated; quaternary ammonium amino acid sulfobetaines such as alkyl amidopropyl hydroxysultaines, cocoamidopropyl hydroxysultaine, sodium cocoamphohydroxypropyl sulfonate, or sodium capryloamphohydroxypropyl sulfonate; quaternary ammonium amino acid betaines, e.g., dodecyl betaine; alkyl amidopropyl betaines such as cocoamidopropyl betaine; alkyl dimethyl betaines; phospholipids such as lecithin; acyl dialkyl ethylenediamines, e.g., sodium acyl amphoacetate, disodium acyl amphodipropionate, disodium alkyl amphodiacetate, sodium acyl amphohydroxypropyl sulfonate, disodium acyl amphodiacetate, and sodium acyl amphopropionate; a salt of cocamphodiactetate, such as sodium cocamphodiacetate; and the like.

E. Water

In certain aspects, the compositions include water. Preferably, water is present from about 5% to 75% (w/w) such as about 5, 6, 7, 8, 9, 10, 11, 12, 12.5, 13, 14, 15, 16, 16.6, 17, 17.5, 18, 18.5, 19, 20, 21, 22, 23, 24, 25, 30, 35, 40, 45, 50, 55, 60, 65, 70 or 75% by weight. Preferably, water is present from about 5% to 25% (w/w). More preferably, the composition includes from about 5 to 10%, about 10 to 20%, about 10 to 15%, about 15 to 20%, about 20 to 30%, about 30 to 40%, about 40 to 50%, about 50 to 60%, about 60 to 70%, or about 70 to 75% (w/w) water. Alternatively, the mixture includes about 8, 9, 10, 12, 12.5, 13, 16, 16.6, or 17% (w/w) or q.s. water.

F. Steroids

In another aspect, the composition may include a steroid. Non-limiting examples include cholesterol and derivatives thereof. Preferably, the formulation comprises at most 1% (w/w) of the steroid. More preferably, the formulation comprises at most 0.5% (w/w) of the steroid. Still more preferably, the formulation comprises at most 0.2% (w/w) of the steroid. Alternatively, the formulation comprises at most 0.15% w/w of the steroid; more preferably, at most 0.05% w/w of the steroid.

Steroids may be included in the composition to enhance or improve foam stability. In particular, where surfactant-type components in the formulation result in short-lived foams, a steroid may be added to extend the life of the foam. As discussed below, measureable aspects of foam stability include foam formation, foam height and foam collapsibility.

Procedurally, the surfactant (e.g., Brij) and steroid may be added to the formulation by vortexing and heating. Alternately, the surfactant may be added into the hydroalchoholic fraction and the steroid into the remaining organic part, and the resulting phases then combined. This is the preferred process as it does not require heating.

G. Emollients

Emollients can optionally be added to the foamable formulations of the invention so that the formulations can maintain or increase the moisture content of the stratum corneum when the composition is applied (e.g., the skin of the knee). Emollients may be added to the formulations in addition to the components already described, which may also aid in maintaining or improving the skin condition of the user. The use of emollients in a foamable composition is discussed in U.S. Pat. No. 7,651,990.

In one aspect, added emollients are included in the compositions of the invention at a concentration between about 0.1 and 20% w/w. In another aspect, the added emollient can be present in the composition at a concentration between about 0.5% and 10% w/w. In still another aspect, the emollient concentration can be between about 1% and 5% w/w.

Emollients are generally separated into two broad classes based on their function. The first class of emollients functions by forming an occlusive barrier to prevent water evaporation from the stratum corneum. The second class of emollients penetrate into the stratum corneum and physically bind water to prevent evaporation. The first class of emollients is subdivided into compounds which are waxes at room temperature and compounds which are liquid oils. The second class of emollients includes those which are water soluble and are often referred to as humectants.

Suitable emollients may be selected from any of the classes known in the art. A general list of useful emollients appears, for example, in U.S. Pat. No. 4,478,853 and in EP patent application 0 522 624A1 as well as in the CTFA Cosmetic Ingredient Handbook published by The Cosmetic, Toiletry, and Fragrance Association, Wash. D.C. (1992) under the listings "Skin Conditioning agents," "emollients," "humectants," "miscellaneous" and "occlusive."

In some aspects, emollients may be chosen from the following non-limiting list of general emollients, occlusive emollients, and humectants. Examples of general emollients include short-chain alkyl or aryl esters ($C_1$-$C_7$) of long-chain straight- or branched-chain alkyl or alkenyl alcohols or acids ($C_9$-$C_{32}$) and their polyethoxylated derivatives; short-chain alkyl or aryl esters ($C_1$-$C_7$) of $C_4$-$C_{12}$ diacids or diols optionally substituted with one or more hydroxyl groups; alkyl or aryl $C_1$-$C_{10}$ esters of glycerol, pentaerythritol, ethylene glycol, propylene glycol, as well as polyethoxylated derivatives of these and polyethylene glycol; $C_{12}$-$C_{22}$ alkyl esters or ethers of polypropylene; $C_{12}$-$C_{22}$ alkyl esters or ethers of polypropylene/polyethylene glycol copolymer.

Non-limiting examples of occlusive emollients include cyclic and linear dimethicones; polydialkylsiloxanes; polyarylalkylsiloxanes; long chain ($C_8$-$C_{36}$)alkyl and alkenyl esters of long straight or branched chain alkyl or alkenyl alcohols or acids; long chain ($C_8$-$C_{36}$)alkyl and alkenyl amides of long straight or branched chain ($C_8$-$C_{36}$)alkyl or alkenyl amines or acids; hydrocarbons including straight and branched chain alkanes and alkenes such as squalene, squalane and mineral oil; jojoba oil; polysiloxane polyalkylene copolymers; short chain alkyl or aryl esters ($C_1$-$C_{36}$) of $C_{12}$-$C_{22}$ diacids or diols optionally substituted with one or more hydroxyl groups such as diisopropyl dimer dilinoleate; and $C_{12}$-$C_{22}$ alkyl and alkenyl alcohols; long chain alkyl or aryl esters ($C_8$-$C_{36}$) of $C_{12}$-$C_{22}$ diacids or diols optionally substituted in available positions by —OH, such as diisostearyl dimer dilinoleate; lanolin and lanolin derivatives; and beeswax and its derivatives.

Non-limiting examples of humectant-type emollients include glycerol, polyglycerols (including: diglycerol, triglycerol, polyglycerin-3, tetraglycerol, hexaglycerol, decaglycerols) propylene glycol, dipropylene glycol, polypropylene glycol, polyethylene glycol (PEG-2 to PEG-45M, preferably a molecular weight between about 300 and 1,000), sorbitol, polyhydric alcohol ethoxylates (e.g., sorbeth-6, sorbeth-30, glycereth-1 to glycereth-31) methoxides of polyethylene glycol (Methoxy PEG-2 to Methoxy PEG-100) methoxides of polyhydric alcohol ethoxylates (e.g., glycereth-7 methoxide), pantothenol, gluconic acid salts and the like. Other humectant-type agents like that could also be employed include: 1,2,6-hexanetriol, acetamide mea, aluminum hydroxide, arginine pea, butoxypropanol, butylene glycol, dimethyl imidazolidinone, dimethylsilanol hyaluronate, dipotassium glycyrrhizate, erythritol, ethoxy-diglycol, fructose, glucamine, gluconic acid, glucose, glucose glutamate, glucuronic acid, glutamic acid, glycogen, glycyrrhizic acid, heilmoor clay, hexacosyl glycol, histidine, hyaluronic acid, hydrogenated honey, hydrogenated starch, hydrolysate, hydrolyzed collagen, hydrolyzed elastin, hydrolyzed glycosaminoglycans, hydrolyzed keratin, hydrolyzed silk, hydrolyzed soy protein, hydrolyzed wheat protein, hydroxyethyl sorbitol, inositol, inositol hexa-pea, lactamide mea, lactic acid, lactitol, lactose, lysine pea, magnesium pea, maltitol, manganese pea, mannitol, mel (honey extract), menthyl pea, methyl gluceth-10, methyl gluceth-20, pea (pidolic acid), lactamide, polydextrose, polyglucuronic acid, polyglyceryl sorbitol, potassium pea, ppg-20 methyl glucose ether, ppg-38-buteth-37, saccharide isomerate, serica, silk amino acids, sodium carboxymethyl chitin, sodium lactate, sodium mannuronate methylsilanol, sodium pea, sodium pea methylsilanol, sodium polyglutamate, soluble collagen, sorbitol, sucrose, tea-lactate, tea-pea, trehalose, trilactin, urea, xylitol, *zea mays*, zinc pea, and combinations thereof.

The addition of one or more emollients may affect the viscosity and stability of the compositions of the present invention. In some embodiments, a single emollient may be added to the composition. In some embodiments, two or more emollients may be added to the composition. While any of a variety of emollients may be added to the formulations of the present invention, some embodiments will include wax and oil type emollients either alone or combined with water soluble emollients. In some embodiments of the invention, emollient systems can be comprised of humectants in addition to occlusive wax and oil emollients in concentrations that achieve a moisturizing effect and which maintains and improves the condition of the skin upon repeated use. Emollients may be non-comedogenic and chosen to avoid skin irritation or sensitization reactions.

H. Propellants

The formulations of the present invention are preferably not propellant-based (i.e., substantially propellant-free or propellant-free). However, the option of including a propellant in the inventive formulations is herein contemplated.

Preferably, the propellant is from about 3 to 45% (w/w) of the foamable formulation. More preferably, the propellant is about 5%, about 10%, about 15%, about 20%, about 25%, about 30%, about 35%, about 40%, or about 45% (w/w) of the foamable formulation.

Without being bound by theory, the addition of propellants to inherently foamable formulations (e.g., those formulations foamable by manual aeration) can provide a more consistent delivery of the active agent. For example, addition of a propellant to a foamable formulation may be useful in producing metered dosing of the composition, as required by certain regulatory bodies to prevent over- or under-doing. However, the addition of a propellant is not key for deriving a foam from the formulations of the invention.

In some aspects, the formulations are capable of being formulated into an aerosol foam or a mousse by addition of propellant to the composition. The propellant may form a separate layer on the composition or the propellant may be emulsified or miscible in the composition. The use of emollients in a foamable composition is discussed in U.S. Pat. No. 7,651,990.

Suitable propellants can be chosen from chlorofluorocarbons (CFCs), hydrochlorofluorocarbons (HCFCs), hydrofluorocarbons (HFCs), perfluorinated alkanes, and lower alkanes ($C_1$-$C_5$) as well as nitrous oxide dimethyl ether and other solvent-soluble propellants. Suitable lower alkanes include n-pentane, propane, butane, and isobutane or mixtures thereof. In some aspects, the propellant can comprise a 70/30 mixture of propane/isobutane. In other aspects, the propellant is A-46, which is a blend of 84% A-31 isobutane and 16% A 108 propane. In order to produce an aerosol composition, the composition is first formulated and charged into an appropriate pressure-rated container. A suitable propellant may then be added to the composition under pressure at approximately 1-30%, and preferably 3-20%, by volume. Non-limiting examples of canisters useful in dispensing propellant-based foams include Aptar's BOV and EP systems.

In one aspect, the composition comprises a foamable formulation as previously described mixed with a propellant in a ratio from about 70:30 to 99:1% (w/w). In another aspect, the composition comprises a foamable formulation as previously described mixed with a propellant in a ratio from about 85:15 to 97:3% (w/w). In a further aspect, the composition comprises a foamable formulation as previously described mixed with a propellant in a ratio of about 90:10% (w/w). Preferably, the propellant is A-46.

In another embodiment, the process for preparing a propellant formulation comprises adding the propellant (e.g., at 10% concentration by weight) to the foamable formulation (e.g., at 90% concentration by weight) and pressure-filling the cans using a Kartridge Pak pressure filler.

I. Other Components

In one aspect, the formulation additionally comprises an anti-oxidant. Preferred anti-oxidants for use in the present invention include butylated hydroxytoluene, butylated hydroxyanisole, ascorbyl linoleate, ascorbyl dipalmitate, ascorbyl tocopherol maleate, calcium ascorbate, carotenoids, kojic acid and its pharmaceutically acceptable salts, thioglycolic acid and its pharmaceutically acceptable salts (e.g., ammonium), tocopherol, tocopherol acetate, tocophereth-5, tocophereth-12, tocophereth-18, or tocophereth-80.

In another aspect, the compositions of the present application additionally comprise a pH-adjusting agent. In a further aspect, the pH-adjusting agent is present in an effective amount. In another aspect, the pH-adjusting agent adjusts the pH so that the active (e.g., ibuprofen) is in a protonated form. Accordingly, the pH adjusting agent is present in an amount effective to keep the active in a protonated form.

In one aspect, the pH-adjusting agent is a base. Suitable pH-adjusting bases include bicarbonates, carbonates, hydroxides (e.g., ammonium hydroxide, alkali or alkaline earth metal hydroxides, transition metal hydroxides), and the like. In an alternative aspect, suitable pH-adjusting bases include amines, such as diethanolamine, triethanolamine, or aminopropanol. Additionally or alternatively, the pH-adjusting agent can be an acid, an acid salt, or mixtures thereof. In an embodiment, the pH-adjusting agent comprises two agents (e.g., sodium hydroxide and hydrochloric acid) that are included as needed to adjust the final pH of the composition to a desired pH.

In an embodiment, the pH-adjusting agent is sodium carbonate. In an further embodiment, the composition comprises about 0.1% (w/w) to about 5% (w/w), about 0.15% (w/w) to about 4% (w/w), about 0.25% (w/w) to about 3.0% (w/w), about 0.5% (w/w) to about 2.0% (w/w) or about 1.0% (w/w) of a pH adjusting agent, suitably sodium carbonate.

Other pH-adjusting agents can also be included in the composition, such as other acids, acid salts, or mixtures thereof. Further, the pH-adjusting agent can additionally or alternatively be a buffer. Suitable buffers include citrate/citric acid buffers, acetate/acetic acid buffers, phosphate/phosphoric acid buffers, formate/formic acid buffers, propionate/propionic acid buffers, lactate/lactic acid buffers, carbonate/carbonic acid buffers, and the like. In one aspect, the buffer is phosphate buffered saline (PBS). In an alternate aspect, the buffer is a citrate buffer. In a further embodiment, the buffer comprises or is included in the water component of the hydroalcholic chassis.

In another aspect, the inventive formulation includes a buffer and a second pH-adjusting agent (e.g., sodium hydroxide or hydrochloric acid) to adjust the pH of the composition to a desired pH. More preferably, the second pH-adjusting agent comprises two agents (e.g., sodium hydroxide and hydrochloric acid) that are included as needed to adjust the pH of the hydroalcoholic chassis or final composition to a desired pH.

In still another aspect, the formulation is acidic. In certain aspects, the formulation has a pH of below about 7.5, 6.5, 5.5, 4.5, 3.5, or 2.5. In certain other aspects, the pH of the formulation may range from about 1.5 to 7, about 2 to 7, about 3 to 7, about 4 to 7, or about 5 to 7. In still other aspects, the pH of the formulation may range from about 1.5 to 5.5, about 2.5 to 5.5, about 3.5 to 5.5, or about 4.5 to 5.5. The formulation may include a buffering agent to maintain its acidic pH. Preferably, the formulation has a pH value between about 4 and 7.

In yet another aspect, the formulation is basic. In certain aspects, the formulation has a pH of above about 7, 8, 9, 10, 11, or 12. In certain other aspects, the pH of the formulation may range from about 7 to 12.5, about 7 to 11.5, about 7 to 10.5, about 7 to 9.5, or about 7 to 8.5. In still other aspects, the pH of the formulation may range from about 9 to 12.5, about 9 to 11.5, about 9 to 10.5, or about 8.5 to 10. The formulation may include a buffering agent to maintain its basic pH. Preferably, the formulation has a pH value between about 7 and 10.

In still yet another aspect, the formulation is neutral. In certain aspects, the formulation has a pH of about 7. In certain other aspects, the formulation has a pH from about 6 to about 8.5, from about 5.5 to 8, about 6 to 8, about 6.5 to 8.5, or from about 6.5 to 7.5. The formulation may include a buffering agent to maintain its neutral pH. Preferably, the formulation has a pH value between about 6 and 8.5.

II. Characteristics of Foamable Formulations

Foamability

Despite difficulties in foaming DMSO-based formulations, the inventors have surprisingly been able to prepare topical DMSO formulations that are foamable. In certain preferred aspects, the formulations of the current invention have the advantage of being foamable in the absence of a propellant. For example, the formulations are foamable by manual aeration, wherein a gas is passed through the formulation to produce a foam by manual actuation of a dispensing head. As shown in FIG. 9, DMSO-based formulations were foamed by actuating the pump head of a dispensing system containing the inventive formulation.

Stability

In certain aspects of the instant invention, the foamable formulations have the advantage of maintaining chemical or physical stability over a period of time. In Table 40, for instance, the chemical attributes of preferred formulations were monitored over the course of a three-month period.

In certain aspects of the invention, the pharmaceutical composition is substantially stable with respect to its chemical or physical attributes over a predetermined period of time. The measurable attributes may include, but are not limited to, percentage of active, percentage of impurities, pH, or visual attributes, such as colour and the presence of particulates. In other aspects of the invention, the pharmaceutical composition is substantially stable following storage for about 4, 8, or 12 weeks at 25° C. In still other aspects of the invention, the pharmaceutical composition is substantially stable following storage for about 4, 8, or 12 weeks at 40° C.

In previous work, long term stability results for storage of DMSO-free ibuprofen formulations demonstrated a possible interaction between ibuprofen and ethanol that appeared to result in the production of a degradant (Compound A) presumed to be the ethyl ester of ibuprofen. Surprisingly, the foamable formulations of the present invention containing ethanol show good stability after three months of storage at 40° C. More surprisingly, the inventors have found that the ratio of ethanol to DMSO can be adjusted to improve foam stability. Such characteristics were not previously known for DMSO-based formulations. Best foams were produced at a ratio of 0:70 to 20:60 (EtOH:DMSO)

III. Methods of Preparation

In another embodiment, the present invention provides a method for making foamable formulations of an active agent (e.g., an NSAID, such as diclofenac sodium or ibuprofen). The formulations of the present invention may be made by carrying out the following steps: (i) dispersing some or all of formulation components in dimethyl sulfoxide (preferably, the DMSO-soluble components); (ii) dissolving diclofenac sodium in an aqueous alcohol mixture (e.g., an ethanol/water mixture); (iii) dispersing propylene glycol and glycerol into the NSAID solution from (ii); and (iv) mixing the resulting NSAID solution into the dimethyl sulfoxide blend. Any remaining ingredients (e.g., surfactants) can be added after preparation of the base solution. Heating can also be used during these mixing processes.

Alternatively, the formulations of the present invention may be made by carrying out the following steps: (i) dissolving the NSAID (e.g., diclofenac sodium) in an alcohol solution of DMSO (e.g., an ethanol/dimethyl sulfoxide mixture); (ii) dispersing some or all of the formulation components in a solution of water/diol/(optionally) glycerol (preferably, the components soluble in this solution); and (iii) mixing the NSAID solution from (i) into the thickener blend from (ii). Any remaining ingredients (e.g., surfactants) can be added after preparation of the base solution. Heating can also be used during these mixing processes.

Preferably, the surfactant components can be added last to a DMSO base solution comprising the other ingredients. See, e.g., Example 3.

The formulation can be converted to a foam by several methods. For example, a form can be produced by vigorously shaking or mixing the formulations (e.g., by manual shaking for 10 or 30 sec; by mixing in a Vortex mixer). Preferably, the foam is produced by use of a foaming head (e.g., a dispenser such as those detailed further below; an aerosol spray dispenser).

IV. Methods of Treatment

In certain embodiments, the invention describes a method for treating osteoarthritis comprising the step of applying a topical foamable formulation to a subject to treat the osteoarthritis.

Alternatively, the invention describes a method for treating an injury such as a minor strain, sprain or contusion comprising the step of applying a topical foamable formulation to a subject to treat the injury.

Also included in the present application is a use of the foamable formulation of the application to treat pain as well as a topical composition of the application for use to treat pain. The foamable formulations of the application are useful to alleviate acute pain, chronic pain, or both. Compositions of the application are particularly suited for use in treating acute pain due to minor strains, sprains, and contusions.

In aone aspect, the pain is associated with osteoarthritis. In another aspect, the compositions of the present application are useful for the treatment of other chronic joint diseases characterized by joint pain, degeneration of articular cartilage, impaired movement, and stiffness. Suitable joints include, for example, the knee, elbow, hand, wrist and hip.

In another aspect, the pain is associated with inflammation. In a further aspect, the compositions of the application are useful for the treatment of other pain-associated disorders, including (but not limited to) muscle pain, lower-back pain, neck pain, rheumatoid arthritis, tendonitis, fibromyalgia, myofascial pain, Carpal tunnel syndrome, gout and neuropathic pain conditions.

In certain aspects, the pharmaceutical composition is applied to a joint of the subject. Preferably, the pharmaceutical composition is applied to the knee and the surrounding tissue.

In another aspect, the active agent (preferably, the NSAID) is delivered locally to the joint. In still another aspect, the active agent is delivered to the joint with minimal systemic absorption. In yet another aspect, the active agent is delivered to the tissue surrounding the joint with minimal systemic absorption.

In other aspects, the subject is a human. Alternatively, the subject is a non-human mammal.

In still other aspects, the active agent alleviates pain. Preferably, the pain is caused by arthritis or an injury. More preferably, the pain is caused by osteoarthritis.

In yet still other aspects, the treatment is continued for at least 12 weeks. More preferably, the treatment is continued for at least six months.

In one embodiment, the treatment may be administered once a day. In another embodiment, the treatment may be administered twice a day. In still another embodiment, the treatment may be administered three times a day. In yet another embodiment, the treatment may be administered four times a day. Preferably, the treatment is administered one to two times a day.

Compositions of the present invention produce foams with measurable characteristics. In certain aspects, qualities such as foam stability, easiness to spread and appropriate breakability upon application to the skin or joint are desirable features. These characteristics can be measured by conducting foam formation and foam collapsibility experiments. Foam formation (foam height vs time), for example, is predictive of the generation of a sprayable/spreadable foam. The rate of collapsibility is an important property in the appropriate administration of the foam.

With reference to the figures, foam generation may be monitored by measuring foam height following shaking of the formulation for up to 80 seconds (see FIGS. 11 to 18). Foam collapsing behavior may be monitored by measuring foam deterioration at 0, 5 and 30 minutes following shaking (see FIGS. 19 to 22).

Compositions of the present invention may, if desired, be presented in a canister, foaming dispenser, or other closure system approved by the Food and Drug Administration (FDA) or other government regulatory agencies, which may contain one or more unit dosage forms containing the active ingredient. The canister or dispenser may also be accompanied by a notice associated with the container in a form prescribed by a governmental agency regulating the manufacture, use, or sale of pharmaceuticals, the notice indicating approval by the agency.

Formulation embodiments of the present invention are useful and effective when applied topically to treat a condition. The amount of the active agent present in the composition will be the amount that is therapeutically effective, i.e., an amount that will result in the effective treatment of the condition (e.g., joint pain) when applied. The therapeutically effective amount will vary depending on the subject and the severity of the affliction and can be determined routinely by one of ordinary skill in the art.

In another aspect, the foamable formulation comprising an active agent provides about equal flux (as determined by the Franz cell procedure of Example 5) as a comparative formulation containing the same active agent.

In another, preferred aspect, the foamable formulation comprising an active agent provides better flux than a comparative formulation containing the same active agent. More preferably, the flux of the foamable formulation is at least 1.5 times the flux of the comparative formulation's active. In other words, the ratio of (i) the formulation's active agent flux to (ii) the comparative formulation's active agent is preferably greater than 1.0, and more preferably at least about 1.5. Still more preferably, the composition has a flux that is at least 2.0 times greater than the flux of the comparative formulation. Yet still more preferably, the composition has a flux that is at least 4.0 times greater than the comparative formulation's flux.

In an alternative aspect, a foamable formulation comprising a diclofenac salt has a flux about equal to the flux of a known comparative formulation comprising the same diclofenac salt.

In another, preferred aspect, the foamable composition flux is greater than the flux of the comparative formulation. More preferably, the foamable composition flux is at least 1.5 times the flux of a comparative formulation. In other words, the ratio of (i) the flux of the foamable composition comprising a diclofenac salt to (ii) the flux of a comparative formulation with the same diclofenac salt is preferably greater than 1.0, and more preferably at least about 1.5. In a preferred aspect, the comparative formulation is Pennsaid as disclosed in the Examples, wherein the formulation comprises 1.5% w/w diclofenac sodium, 45.5% DMSO, water, propylene glycol, alcohol, and glycerin.

Still more preferably, the foamable composition comprising a diclofenac salt has a flux that is at least 2.0 times the flux of a comparative formulation having the same diclofenac salt. Yet still more preferably, the foamable composition has a flux that is at least 4.0 times the flux of a comparative formulation.

In another alternative aspect, the present invention provides a foamable composition providing a diclofenac salt flux (as determined by the Franz cell procedure of Example 5) of at least 0.1 $\mu g/hr/cm^2$ over the first 24 hours, preferably at least 0.2 $\mu g/hr/cm^2$ over the first 24 hours. Alternatively, the present invention provides a foamable composition providing an average ibuprofen flux (as determined by the Franz cell procedure of Example 5) of at least 0.4 $\mu g/hr/cm^2$ over the first 24 hours, and preferably, at least 0.8 $\mu g/hr/cm^2$ over the first 24 hours.

V. Dispensing System

Surprisingly, the compositions of the present invention may be formulated into products that can be dispensed as foams from a reservoir using a release assembly (e.g., a hand pump) whenever the release assembly is put into action. The amount of the foam dispensed by the pump may or may not be metered to dispense a consistent amount of the foam. Preferably, the amount is metered to deliver a specific dose.

Figure 40:
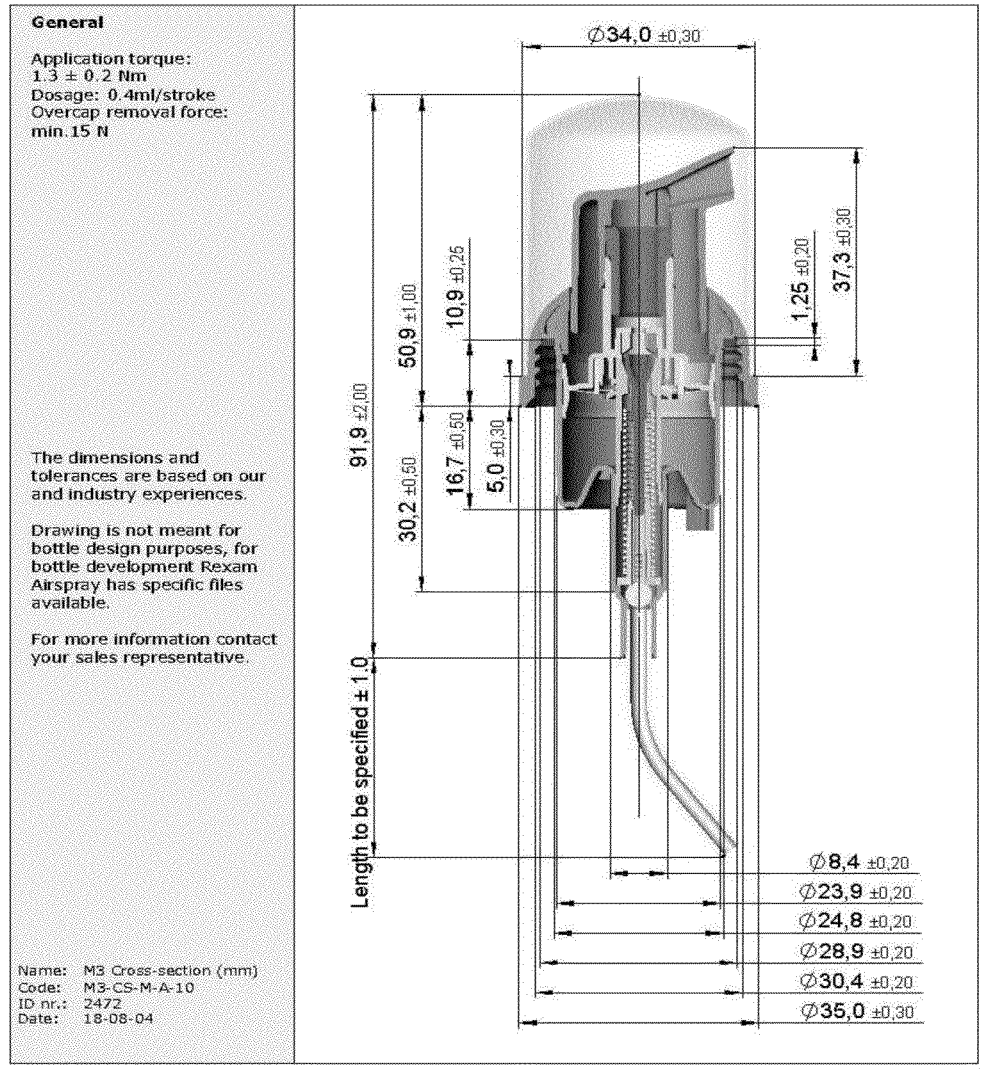
FIG. 40 illustrates the structure of the Rexam M3 foaming head.
Figure 41:
FIG. 41 illustrates the material components of the Rexam M3 foaming head.

Non-limiting examples of pumps useful in dispensing the compositions of the invention include the Rexam M3 foaming head (see, e.g., FIGS. 39-41), the Rexam G3 foaming head, and the Rexam F3 foaming head. For examples of various Rexam pumps, see, e.g., U.S. Pat. No. 5,443,369; US 2010/0320232 (WO 08/133,491); US 2009/0236371 (WO 08/007,943); U.S. Pat. No. 7,757,899 (WO 06/01445); U.S. Pat. No. 6,053,364 (WO 97/13585); US 2008/0314931 (WO 07/86731); and WO 09/136,781. Other pumps useful in dispensing the compositions include the Meadwestvaco Ocean T and Ocean H spray heads. For examples of various Meadwestvaco pumps, see, e.g., US 2009/0212074 (WO 06/112704); US 2009/039110 (WO 06/112701); U.S. Pat. No. 7,726,518 (WO 05/28121); U.S. Pat. No. 7,673,854 (WO 04/69418); U.S. Pat. No. 7,147,133 (WO 02/42005); U.S. Pat. No. 7,735,692 (WO 08/45822); and U.S. Pat. No. 6,547,162 (WO 99/54054). However, the compositions of the invention are not limited to being dispensed from only one type of dispenser or through only one type of hand pump.

Further, the dispenser or pump head may include additional or altered features that assist in optimizing foam stability, especially for low-viscosity formulations. These features include, but are not limited to, the inclusion, arrangement, and hole size of meshes in the pump head; the size and shape of the mix chamber; and varied dip tube and nozzle lengths. Non-limiting pump parameters that may assist in optimizing foam include the output volume (e.g., 0.4 ml; 0.75 ml; 1.20 ml; 1.50 ml), the stroke length (e.g., 11.0 mm; 14.8 mm; 18.8 mm). and the thread diameter (e.g., 30; 40; 43).

Other pump parameters may be useful for ease of operation and manufacture. Preferably, the hand pump includes only one reservoir. Preferably, the dip tube length is 18.8 mm or less.

In certain aspects, the present invention sets forth a method of mechanically aerating a foamable DMSO formulation, thereby producing a foam. Preferably, the foam is a quick-breaking-foam. Preferably, the method includes a step of passing the DMSO formulation and a gas through a mesh to form a foam. Preferably, the gas is air; alternatively, the gas may comprise up to 5%, 10%, or 15% (w/w) propellant.

The compositions of the invention are suitable for use on mammalian skin including the skin covering or surrounding a human knee joint. In non-aerosol formulations of the invention, the compositions may be contained in a non-aerosol dispenser equipped with a conventional hand pump, and the composition may be pumped onto the hands or other areas of the body. The pumping action required to dispense the compositions will create a discrete volume of a dispensed composition as a stable foam.

One method for producing a foam of the present invention comprises: providing a dispenser comprising a reservoir operably linked (e.g., in fluid communication) with a release assembly (e.g., dispensing head); filling the reservoir of the dispensing system with a foamable formulation as previously described; and actuating the release assembly to manaully aerate the formulation, thereby releasing a foam from the release assembly. This method is a particular advantage of some aspects of the present invention, since producing a foam from a formulation comprising DMSO by manual aeration is difficult.

EXAMPLES

Example 1

Diclofenac Sodium Foaming Formulations

Materials

Diclofenac sodium was obtained from Nuvo Manufacturing (Varennes). All ingredients were USP/NF grade materials, and all excipients are available from commercial sources without further custom manufacturing.

TABLE 1

Chemicals

| Chemical Name | Vendor | Catalog # | CAS number |
|---|---|---|---|
| Plantapon ACG 50 | Cognis | na | na |
| Pluoronic F-68 | Hyclone | SH30612.01 | 9003-11-6 |
| Pluracare L 64 | BASF | 52048478 | na |
| Span 80 | Fluka | 85548 | 1338-43-8 |
| Span20 | Sigma | S6635 | 1338-39-2 |
| Tween 20 | Sigma-Aldrich | P1379 | 9005-64-5 |
| Tween 60 | Acros | 278620010 | 9005-67-8 |
| Tween 80 | Sigma-Aldrich | P1754 | 9005-65-6 |
| Phospholipid GmbH | Sample | na | na |
| Brij 30 | Acros | 21672500 | 9002-92-0 |
| Brij 58 | Acros | 344295000 | 9004-95-9 |
| Brij 78 | Acros | 368225000 | 9005-00-9 |
| Brij 98 | Acros | 347185000 | 9004-98-2 |
| Brij 721 | Spectrum | B1685 | 9005-00-9 |
| Polaxamer 407 | Spectrum | P1166 | 9003-11-6 |
| Sodium Laureth Sulfate (Steol CS-370) | Stepan | Steol CS-370 | na |
| Sodium Cocoyl-sarcosinate (Perlastan C-30) | Struktol | n/a | 61791-59-1 |
| Disodium Lauryl Sulfosuccinate | McIntyre | n/a | 26838-05-1 |
| Glycerol Ricinoleate | Phoenix | na | 68459-67-6 |
| Glyceryl Dilaurate | Pfaltz & Bauer | G03120 | 539-93-5 |
| Glyceryl Monooleate | Pfaltz & Bauer | G03225 | 25496-72-4 |

TABLE 1-continued

Chemicals

| Chemical Name | Vendor | Catalog # | CAS number |
|---|---|---|---|
| Ammonium Lauryl Sulfate | Spectrum | A1987 | 68081-96-9 |
| Triethanolamine Lauryl Sulfate | Spectrum | T1484 | 139-96-8 |
| Docusate Sodium | Spectrum | DO105 | 577-11-7 |
| Lathanol (Sodium Lauryl Sulfoacetate) | Stepan | SPN-5779-A | na |
| N-Lauryl Sarcosinate | Sigma | L5000 | 97-78-9 |
| Glyceryl Laurate (Glycerol Monolaurate) | TCI (VWR) | TCG0081 | 142-18-7 |
| Sodium Lauryl Ether(2) Sulfate | Colonial Chemicals | Colonial SLES - 70% | 3088-31-1 |
| Cocamidopropyl Hydroxysultaine | Stepan (50%) - sample | Amphosol CS-50 | 68139-30-0 |
| Glyceryl Caprylate | Abitec - sample | Capmul MCM | 26402-26-6 |
| Oleyl Betaine | McIntyre group | Mackam OB-30 | 871-37-4 |

Stability of DMSO Foams I

The potential foaming qualities of excipients were tested with a DMSO solution base. The solution base was composed of DMSO (45.5% w/w), water, propylene glycol, ethanol, glycerin, and the active agent diclofenac sodium (1.5% w/w). In some cases, the base could be composed of Pennsaid® (DMSO and active agent as above, glycerin, water, propylene glycol, ethanol), while in others the base contained the above amounts of DMSO and active agent, along with water (5 to 19% w/w), propylene glycol (9 to 13% w/w), ethanol (1 to 50% such as 9.8 to 29.8% w/w) and glycerin (9.2 to 11.2% w/w) (See also US 2008/0300311 A1, incorporated herein by reference.) Glycerin-free bases may also be used. Unless where indicated otherwise, "DMSO base" as used herein consistutes Pennsaid® less 2% glycerine.

Each excipient was added directly to a DMSO solution base at 2% w/w. The foaming qualities of the formulations were then tested by two methods:

1) Vortexing: A 40-ml glass vial containing 10 ml of the formulation was briefly vortexed. The time for the foam to collapse was then measured. For this experiment, a foam was considered collapsed when the surface of the liquid was visible in the center of the vial. Residual bubbles could still be present around the perimeter of the glass vial.

2) Foaming Head: The formulation was dispensed from a Rexam M3 foaming head. The dispenser was primed twice prior to dispensing on the laboratory benchtop. The collapse time for the foam was then measured. For this experiment, a foam was considered collapsed when a distinct liquid phase was visible. A dissipating foam head still existed on top of the liquid phase, but the formulation would flow freely due to the liquid phase. This was a qualitative assessment meant to give a general idea of foam characteristics.

The specific foam dispenser utilized in the foaming studies was acquired from Airspray International, Inc, a wholly owned subsidiary of Rexam International Groups, located at 3768 Park Central Blvd, North Pompano Beach, Fla. 33064. Specific configuration and foaming properties of the Airspray (Rexam) M3 Mini Foamer are provided in FIGS. 39-41.

Table 2 lists the results of this study. Values are in seconds.

TABLE 2

Effects of surfactant types on foam quality.

| Additive (added to DMSO Base at 2 wt %) | pH | Vortex foam time (in seconds unless indicated otherwise) | Spray time |
|---|---|---|---|
| Poloxamer 188 (ethylene oxide (A)/propylene oxide (B) block copolymer, A:B:A, A = 80 repeating units, B = 27 units) | 8.82 | >1 min | 8, very liquid |
| Poloxamer 407 (as 188, but A = 101, B = 56) | 8.76 | >1 min | 12, very liquid |
| Brij 30 (polyoxyethylene (4) lauryl ether) | 8.71 | >1 min | 23 |
| Brij 58 (polyoxyethylene (20) cetyl ether) | 8.7 | >1 min | 12 |
| Brij 78 (polyoxyethylene (20) stearyl ether) | 8.7 | >1 min | 10 |
| Brij 98 (polyoxyethylene (20) oleyl ether) | 8.4 | >1 min | 8 |
| Brij 721 | | >1 min | 6 |
| Phospholipon NG90 | | >1 min | 2, very runny |
| Tween 20 | 8.48 | 10 | 2 |
| Tween 60 | 8.5 | 10 | 2 |
| Tween 80 | 8.5 | 18 | 2 |
| Sodium lauryl sulfoacetate | 7.98 | 4 | negligible |
| Sodium laureth sulfate | 8.24 | 4 | negligible |
| N-lauroyl sarcosinate | 6.3 | 3 | negligible |
| Span 20 | 8.1 | negligible | negligible |
| Span 80 | 8.16 | negligible | negligible |
| Sodium cocoyl sarcosinate | 8.73 | negligible | negligible |
| Disodium lauryl sulfosuccinate | 7.86 | negligible | negligible |
| Triethanolamine lauryl sulfate | 7.5 | 2 | negligible |
| Glyceryl dilaurate | 7.98 | negligible | negligible |
| Glycerol monooleate | 8.05 | negligible | negligible |
| Glyceryl ricinoleate | 8.36 | negligible | negligible |
| Glyceryl caprylate | 8.6 | negligible | negligible |
| Glycerol monolaurate | 8.54 | 3 | 2 |
| Cocamidopropyl hydroxysultaine | 8.5 | negligible | negligible |
| Oleyl betaine | 8.54 | negligible | negligible |
| Sodium lauryl ether(2) sulfate | 8.28 | negligible | negligible |
| Amphosol | 8.02 | 7 | negligible |
| Ammonium lauryl sulfate | 8.29 | 2 | negligible |
| Sodium docusate | | negligible | negligible |
| Pluronic L-62 | | negligible | negligible |
| Pluronic F-68 | | 12 | 3 |
| Plantapon ACG 50 | | negligible | negligible |

The majority of surfactant types produced negligible foam formation from the DMSO solution. Any foam produced was short-lived and dissipated almost immediately.

Some surfactant types formed stable foams after vortexing, but did not foam properly upon dispensing from the foaming head. This group of excipients included the poloxamers and phospholipid.

Only the polyalkylene oxide alkyl ether class of surfactants (e.g., Brij) formed a stable foam. These surfactants consistently formed the most stable foams after dispensation from the foaming head.

Example 2

Effects of Polyethylene Glycol Alkyl Ether Surfactant

A number of additives were tested in conjunction with Brij 30 in attempts to further stabilize the foam. These additives were added up to 2% w/w (or up to the maximum solubility limit in the case of cetostearyl and cetyl alcohol) in combination with 1% w/w Brij 30. Both the Brij 30 and the additive were mixed directly with the DMSO solution.

The DMSO base was prepared as in Example 1. The space left by the removal of the 2% glycerin was used to incorporate up to 2% w/w foam-forming and foam-stabilizing agents.

In these studies, foam stability was estimated as the time elapsed until the foam completely collapsed, which is a different endpoint than when a distinct liquid phase is visible. The latter endpoint leads to a longer measured "stability" time.

As in Example 1, the foam stability was measured both by vortexing and by dispensing from a Rexam M3 foaming head. None of the additives tested improved the qualities of the foam made in comparison to a 2% w/w Brij 30/DMSO base solution (the control).

In later experiments, foam formation studies were performed using Meadwestvaco Ocean T and Ocean H spray heads. Experiments with longer vortexing times than those performed in Table 2 were also conducted.

An outline of some of the combinations can be seen in Table 3:

TABLE 3

Polyalkylene Oxide Alkyl Ether Variants with Varying Additives

DMSO Base Foam Formulations

| Ingredients | Base/1.5% Brij 98 % w/w | Base/1% Brij 30 % w/w | Base/ 2% Brij 30 % w/w | Base/ 1% Brij 30/ 0.15% 250M % w/w | Base/1% Brij 30/ 0.5% 250M % w/w | Base/ 1% Brij 30/ 1% PVP % w/w | Base/ 1% Brij 30/1% PVA % w/w | Base/ 1% Brij 30/1.5% 407 % w/w |
|---|---|---|---|---|---|---|---|---|
| DMSO Base | 98.5 | 99 | 98 | 98.85 | 98.5 | 98 | 98 | 97.5 |
| Brij 30 | | 1 | 2 | 1 | 1 | 1 | 1 | 1 |
| Brij 98 | 1.5 | | | | | | | |
| Hydroxyethyl-cellulose 250M | | | | 0.15 | 0.5 | | | |
| Polyvinylpyrrolidone | | | | | | 1 | | |
| Polyvinyl alcohol | | | | | | | 1 | |
| Poloxamer 407 | | | | | | | | 1.5 |
| Foam stability after vortexing for 20 sec | 16 min 40 sec | 9 min 20 sec | 5 min 10 sec | 12 min 50 sec | 2 min 20 sec | 4 min 10 sec | 6 min 20 sec | 10 min 40 sec |
| Foam stability after dispensation from a | 70 sec | 70 sec | 60-80 sec | 45 sec | 10 sec | 30 sec | 30 sec | 30-40 sec |

TABLE 3-continued

Polyalkylene Oxide Alkyl Ether Variants with Varying Additives

DMSO Base Foam Formulations

| Ingredients | Base/1.5% Brij 98 % w/w | Base/1% Brij 30 % w/w | Base/ 2% Brij 30 % w/w | Base/1% Brij 30/ 0.15% 250M % w/w | Base/1% Brij 30/ 0.5% 250M % w/w | Base/ 1% Brij 30/ 1% PVP % w/w | Base/ 1% Brij 30/1% PVA % w/w | Base/ 1% Brij 30/1.5% 407 % w/w |
|---|---|---|---|---|---|---|---|---|
| Rexam M3 foaming head | | | | | | | | |

Brij 30 in combination with cococaprylate, oleyl alcohol, Imwitor 948, or cholesteryl palmitate all formed foams with reduced stability in comparison to the control solution.

Cetostearyl alcohol and cetyl alcohol are relatively insoluble in the solution base, and were added at <0.25% w/w. Both additives reduced foam stability.

Cocamide DEA was first reported as slightly increasing the stability of the foam. After further testing, this effect was deemed negligible. It was most likely observed due to difficulties in reproducible dispensations from the dispensing head.

The addition of Phospholipon NG90 with Brij 30 was observed to increase the foam stability slightly when compared to the control. However, although the foam demonstrated some increase in stability, it was substantially more runny.

The addition of Poloxamer 407 with Brij 30 led to a foam with considerable stability when vortexed in a glass vial. This increase in stability was not observed when the solution was dispensed from the foaming head. A similar trend was also observed with sole addition of Poloxamer 407 to the DMSO solution base (Example 1). It is possible that Poloxamer 407 may foam sufficiently under pressurized conditions, but that the manual foaming head dispenser is not sufficient to adequately form a poloxamer foam.

Thickeners were also tested in conjunction with Brij 30. These thickeners included hydroxylpropyl cellulose, hydroxylpropylmethyl cellulose, hydroxyethyl cellulose, polyvinyl alcohol, and polyvinylpyrrolidone. In the cases tested, increasing the viscosity of the formulation was detrimental to the foam quality during dispensation.

Conclusions

A DMSO foam formulation is difficult to make, with the majority of surfactants forming foams with less than desirable qualities. Despite this, polyethylene glycol alkyl ethers (e.g., Brij 30, Brij 78, Brij 90, Brij 98 and the like) provided surprisingly good results. Other additives were tested in conjunction with Brij, but did not demonstrate any increase in foam quality/stability.

Example 3

Investigation of Foam-Stabilizing Agents

For superior properties, the foams containing polyalkylene glycol alkyl ether may also contain cholesterol as a foam stabilizer. Optionally, adding another ingredient such as a second surfactant may improve the foam characteristics.

Addition of Foam Forming and Foam Stabilizing Agents: Ingredients were incorporated into the formulation by vortexing and (if needed) by heating up to 80° C. for 10 min in a covered vial. The scale was approximately 20 g product per formulation batch. The formulations were left overnight at room temperature. The next day, the formulations were filtered through a LuerLock NormJect syringe, Henke Sass Wolf GmbH (Tuttlingen, Germany) equipped with a 25 mm diameter Pall filter with 0.2 μm GHP membrane. The product formulations were clear solutions with no suspended particles and precipitates.

TABLE 4

Selected Formulation Compositions

Formulations (P100118)

| Ingredients | I | II | III | IV | V | VI | VII | VIII | IX | X | XI | XII |
|---|---|---|---|---|---|---|---|---|---|---|---|---|
| DMSO base | 98 | 98 | 98 | 98 | 98 | 99.85 | 99.7 | 98 | 98 | 98 | 98 | 98 |
| Brij 30 | 1.7 | 1.85 | 1.85 | | 2 | | | 1.7 | 1.7 | 1.7 | | |
| Brij 98 | | | | | | | | | | | 1.85 | 2 |
| Cholesterol | 0.15 | 0.15 | | 0.15 | | | 0.3 | | | | 0.15 | |
| Sodium dodecyl benzene sulfonate | 0.15 | | 0.15 | 0.15 | | 0.15 | | 0.15 | 0.15 | 0.15 | | |
| Cetyl alcohol | | | | | | | | | | 0.15 | | |
| Cetostearyl alcohol | | | | | | | | 0.15 | | | | |
| Oleyl alcohol | | | | | | | | | 0.15 | | | |

Foaming Studies: The filtered solutions were transferred into VWR 11 dram glass vials with phenolic cup. The set of formulations were manually shaken (all together) for 30 seconds. Immediately the foam heights were measured, and pictures were taken at predetermined intervals as shown in FIGS. 1-8.

Results and Conclusions: Formulations with more lipophilic ingredients, but with some hydrophilic character provided the best foams. Obtained foams were repeatable, not a one-time event. Compositions VIII-X did not give any foam. Although not pictured in this set, the foam formation properties of XI-XII were similar to their Brij 30 counterparts.

The combination of steroids with a polyalkylene glycol alkyl ether surfactant gave good foam stabilizing properties.

A typical steroid such as cholesterol in conjunction with Brij gave stable foams with a duration of at least 5 minutes after spraying.

To further improve the foam, a small amount of ionic surfactant (sodium dodecylbenzene sulfate) was added into the formulations. In some cases, the addition of this surfactant further improved the formulation by forming smaller foam cells (visual observation).

At the concentrations tested, foam stabilizers such as cetyl alcohol, cetostearyl alcohol, oleyl alcohol, glycerin monolaurate, glycerin monostearate, glycerin palmitate, glycerin monoricinoleate, and lecithin (of animal or vegetal origin) did not give stable foams when combined with polyethylene glycol alkyl ethers.

After 24 hours, all the foams reverted to clear solutions. After collapsing of the foam, the formulation reverted to the original clear solution, which can be re-foamed.

Example 4

Foam Spraying Studies

The formulations which appear to give stable foams in vials were sprayed using Meadwestvaco dispensers. The formulations I and II gave spreadable and stable formulations.

Figure 10:
FIG. 10 illustrates the foam produced by dispensing Formulation I (Example 3) when sprayed using a hand dispenser. The picture was taken 2 minutes after dispensing the foam.
Figure 11:
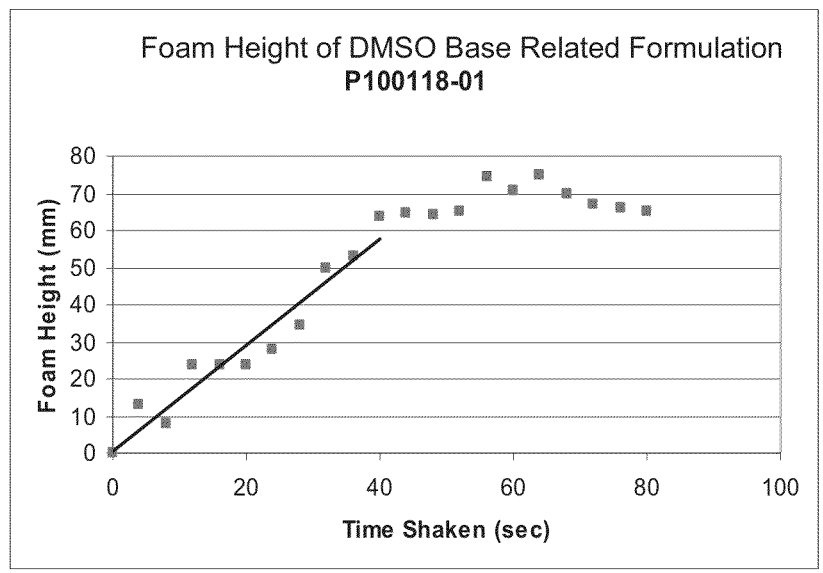
FIG. 11 illustrates the foam height produced by shaking Formulation P100118-01 for 4, 8, 12, 16, 20, 24, 28, 32, 36, 40, 44, 48, 52, 56, 60, 64, 68, 72, 76 and 80 seconds.
Figure 12:
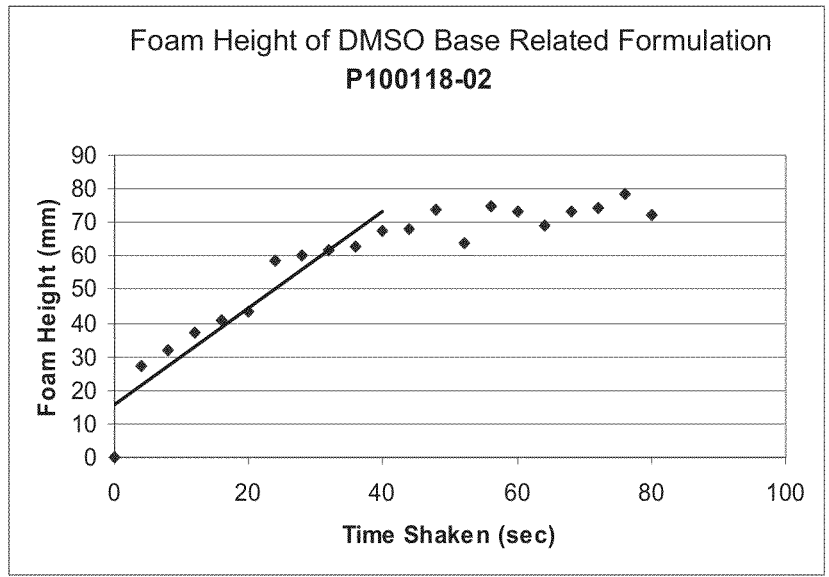
FIG. 12 illustrates the foam height produced by shaking Formulation P100118-02 for 4, 8, 12, 16, 20, 24, 28, 32, 36, 40, 44, 48, 52, 56, 60, 64, 68, 72, 76 and 80 seconds.
Figure 13:
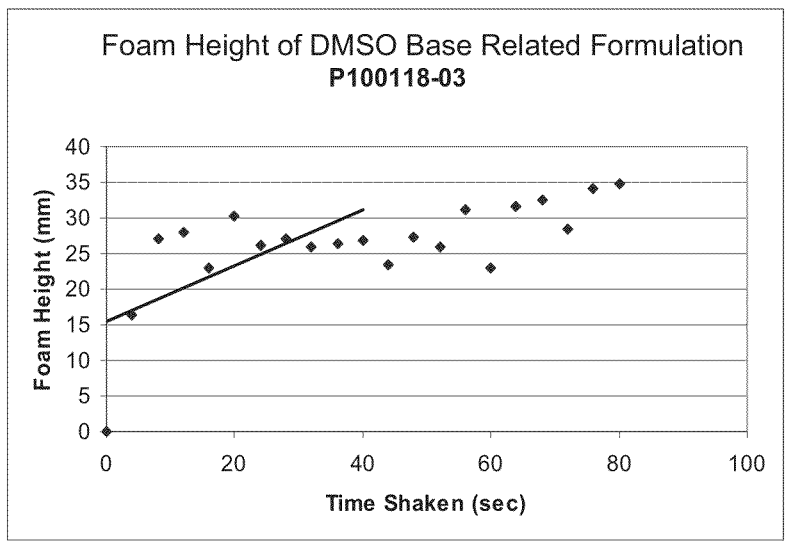
FIG. 13 illustrates the foam height produced by shaking Formulation P100118-03 for 4, 8, 12, 16, 20, 24, 28, 32, 36, 40, 44, 48, 52, 56, 60, 64, 68, 72, 76 and 80 seconds.
Figure 14:
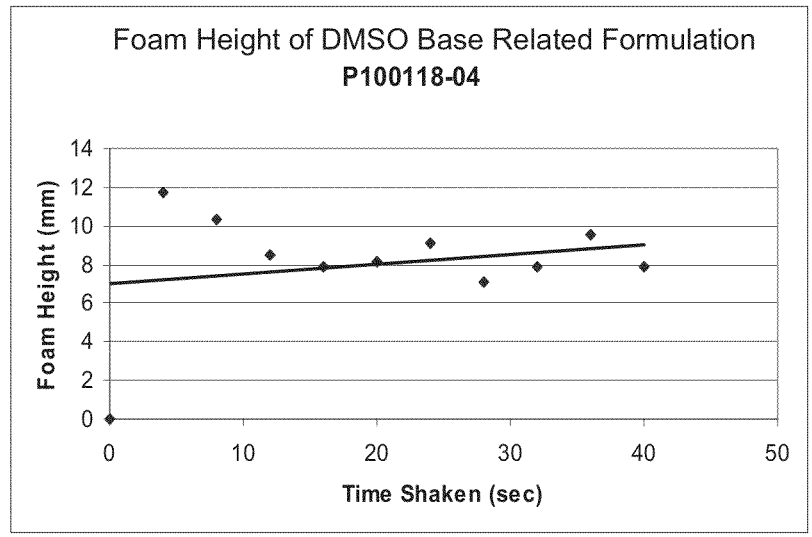
FIG. 14 illustrates the foam height produced by shaking Formulation P100118-04 for 4, 8, 12, 16, 20, 24, 28, 32, 36 and 40 seconds.
Figure 15:
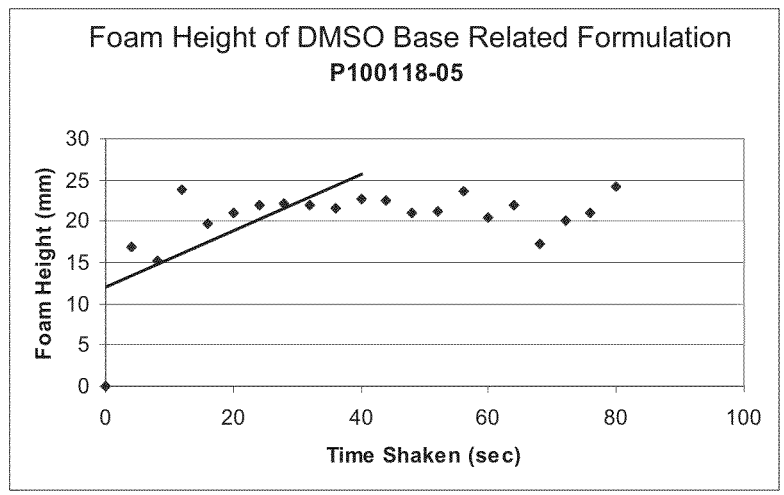
FIG. 15 illustrates the foam height produced by shaking Formulation P100118-05 for 4, 8, 12, 16, 20, 24, 28, 32, 36, 40, 44, 48, 52, 56, 60, 64, 68, 72, 76 and 80 seconds.
Figure 16:
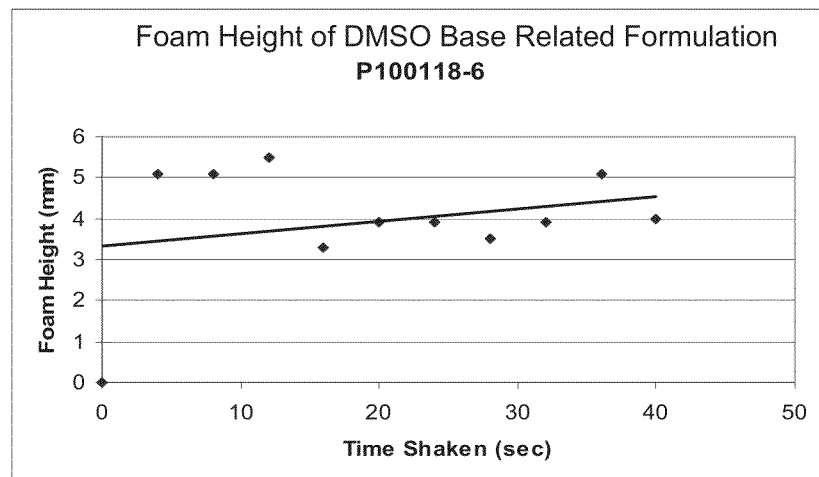
FIG. 16 illustrates the foam height produced by shaking Formulation P100118-06 for 4, 8, 12, 16, 20, 24, 28, 32, 36 and 40 seconds.
Figure 17:
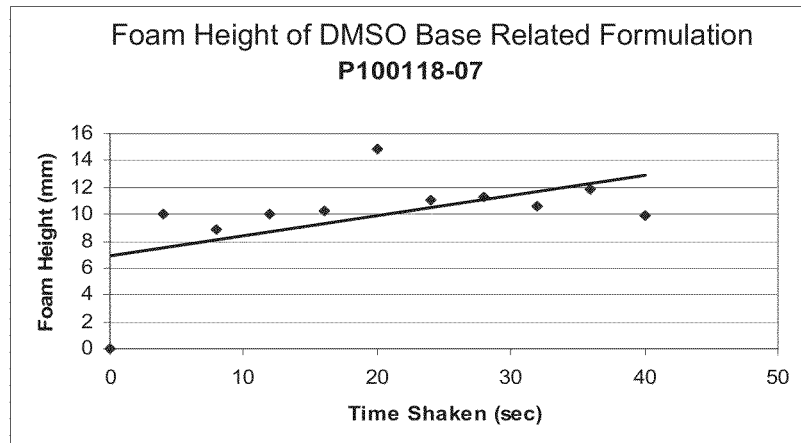
FIG. 17 illustrates the foam height produced by shaking Formulation P100118-07 for 4, 8, 12, 16, 20, 24, 28, 32, 36 and 40 seconds.
Figure 18:
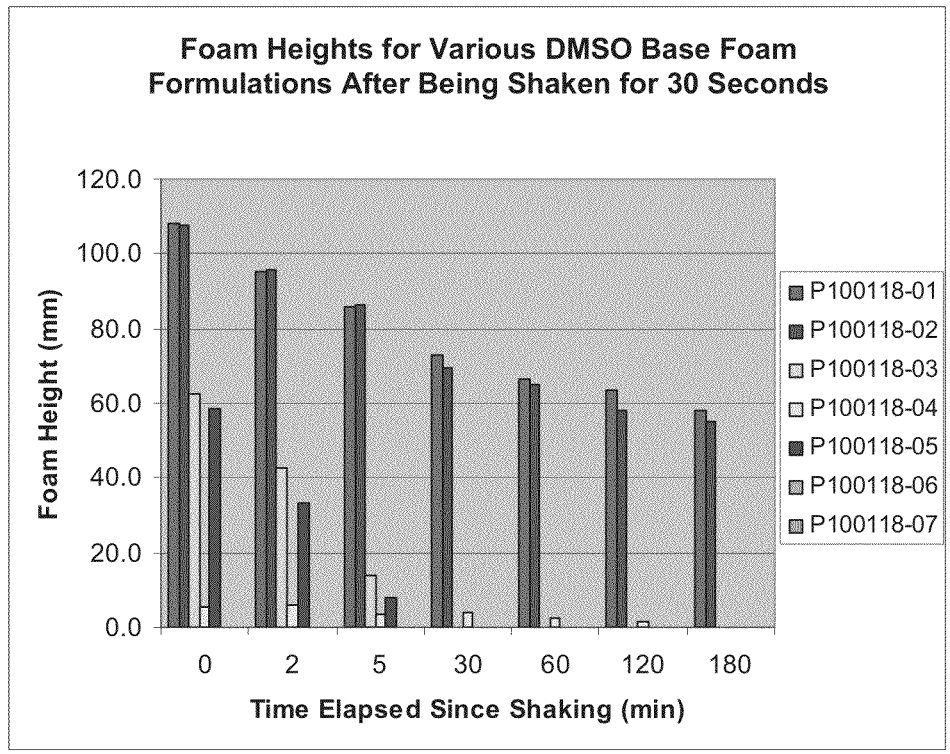
FIG. 18 illustrates the foam height produced by shaking Formulations P100118-01 to P100118-07 after 30 seconds of shaking.
Figure 19:
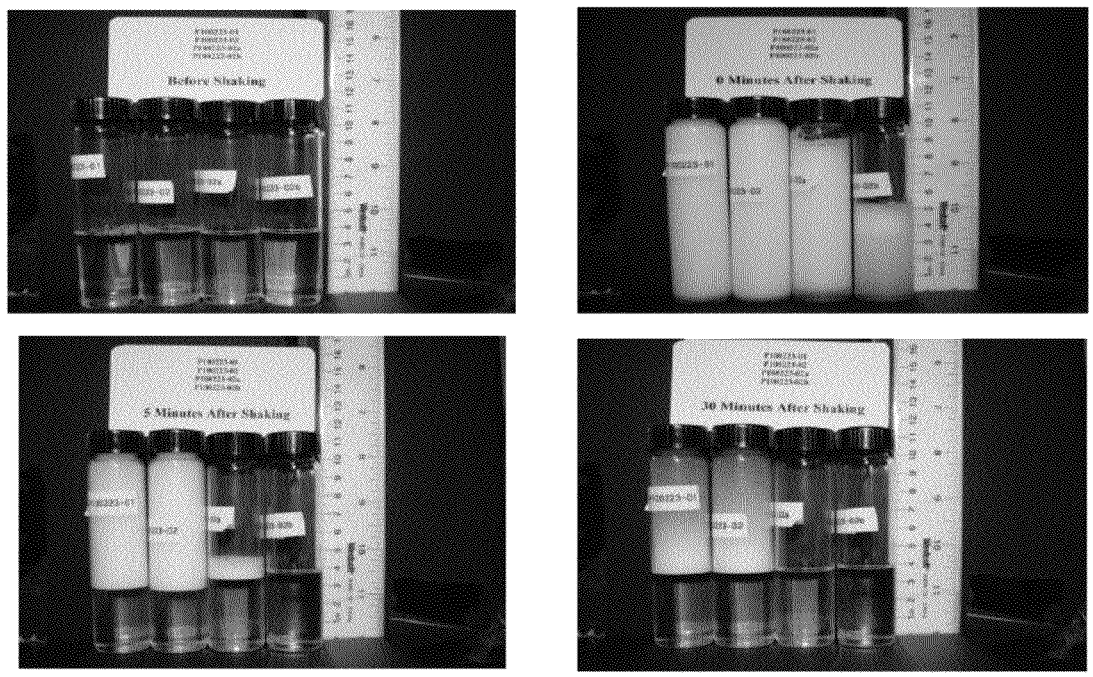
FIG. 19 illustrates the foam collapsibility of a series of topical formulations (P100223) at 0, 5 and 30 minutes after shaking.
Figure 20:
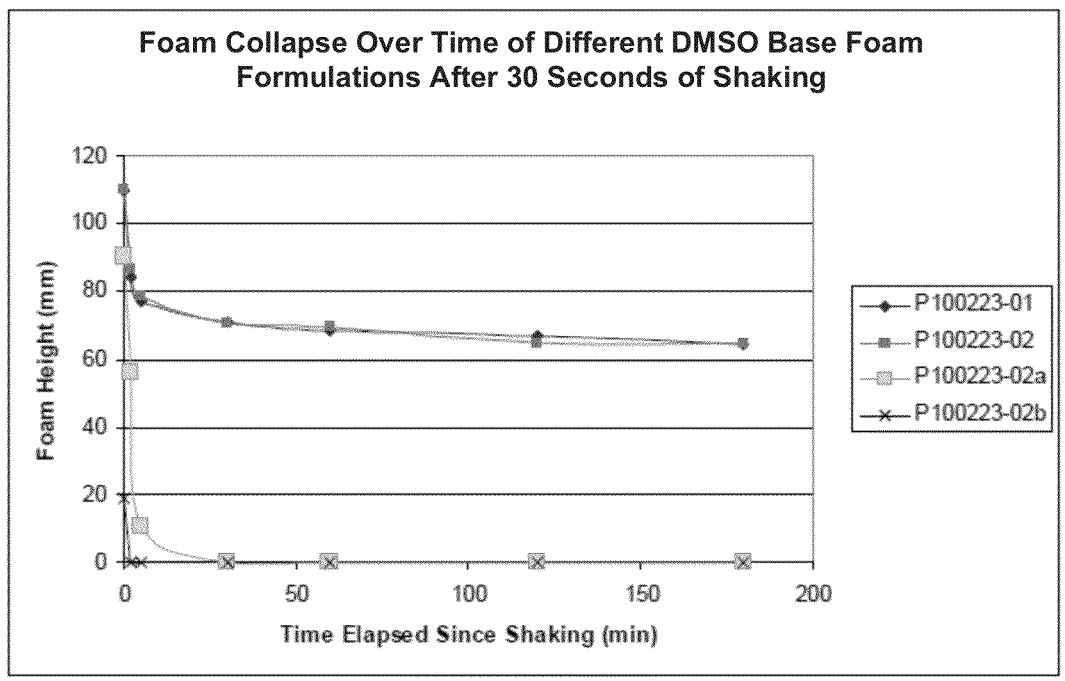
FIG. 20 illustrates the foam collapsibility of a series of topical formulations (P100223) after 30 seconds of shaking.
Figure 22:
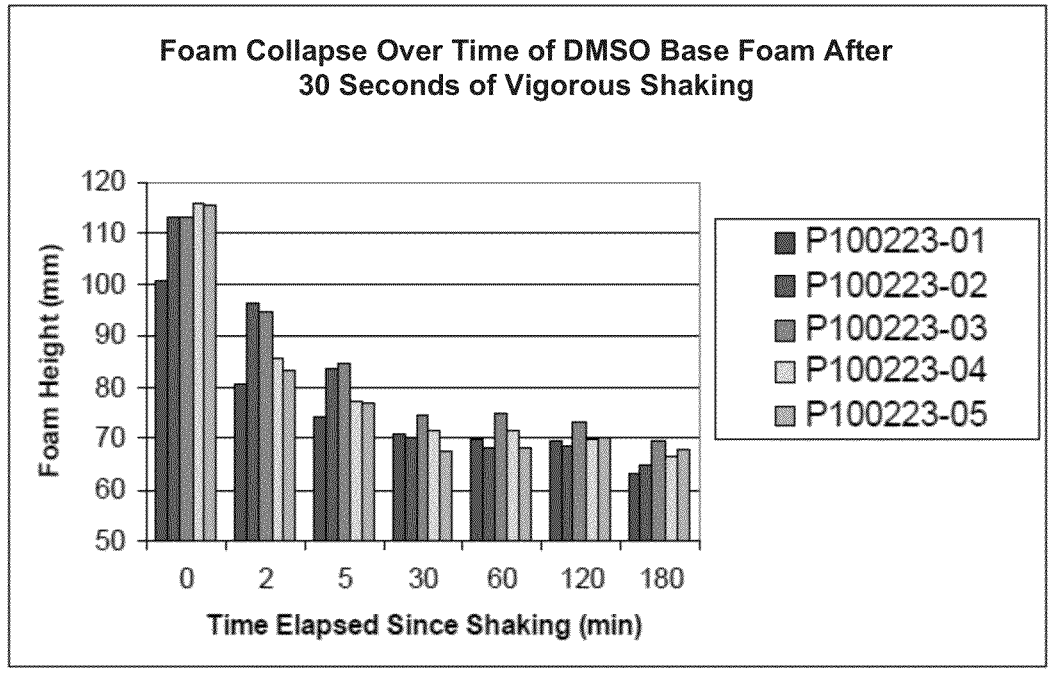
FIG. 22 illustrates the foam collapsibility of a series of topical formulations (P100223) after 30 seconds of shaking.
Figure 23:
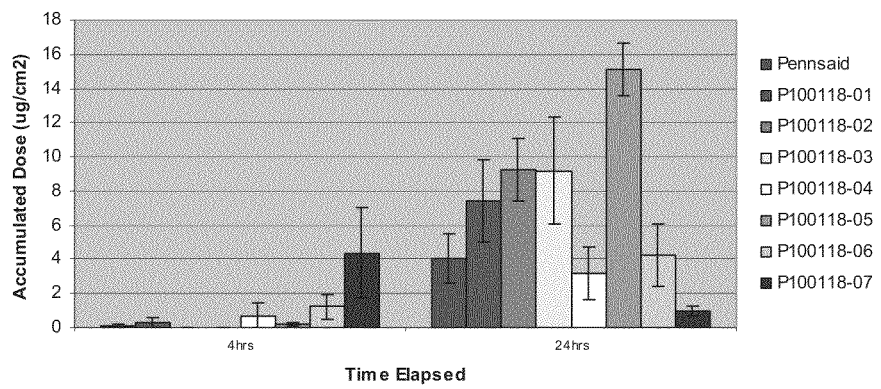
FIG. 23 illustrates diclofenac sodium permeation through dermatomed porcine skin from a series of topical formulations (P100118) at 4 and 24 hours after application.
Figure 24:
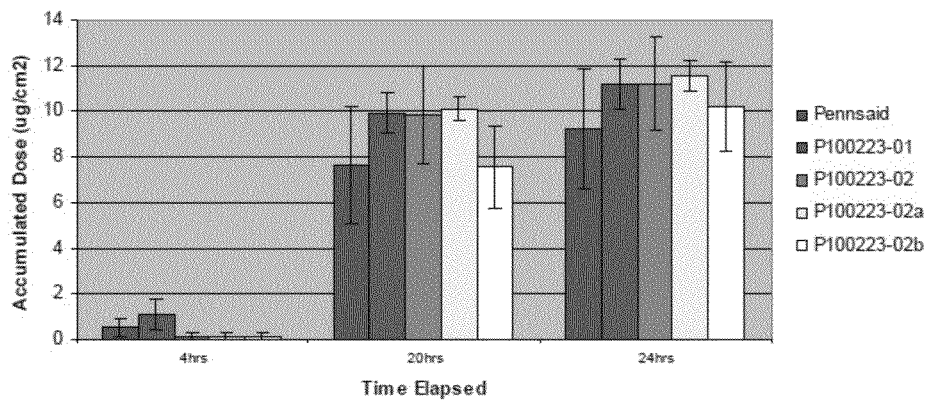
FIG. 24 illustrates diclofenac sodium permeation through Dermatomed procine skin from a series of topical formulations (P100223) at 4, 20 and 24 hours after application.

At 0, 2 and 5 minute intervals, pictures were taken as shown in FIGS. 9 and 10 (for 0 and 2 min).

Figure 25:
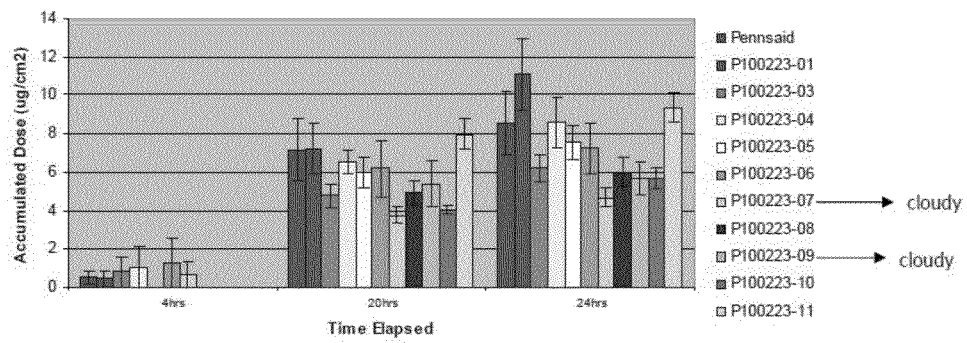
FIG. 25 illustrates diclofenac sodium permeation through dermatomed porcine skin from a series of topical formulations (P100223) at 4, 20 and 24 hours after application.
Figure 26:
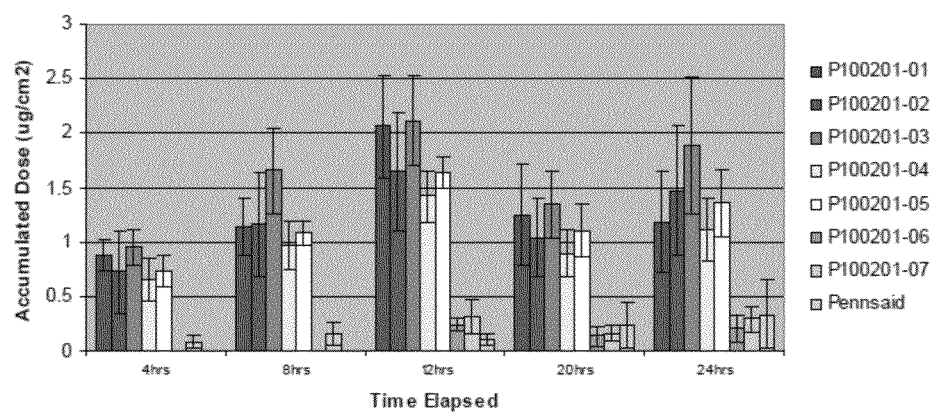
FIG. 26 illustrates diclofenac sodium permeation through human cadaver skin from a series of topical formulations (P100201) at 4, 8, 12, 20 and 24 hours after application.

In later studies, additional embodiments of the inventive foam were examined. Foam generation was monitored by measuring foam height following shaking of the formulation for up to 80 seconds (FIGS. 11 to 18). Foam collapsing behavior for the P100223 series was monitored by measuring foam deterioration at 0, 5 and 30 minutes following shaking (see FIGS. 19 to 22; also see FIG. 25 for P100223 compositions).

Results and Conclusions

Foamable DMSO/diclofenac sodium formulations are possible. The ingredients in the formulation exhibited synergistic foaming activity. Only a convenient spraying head was needed to produce a usable foam.

Example 5

Skin Permeation Studies

General Procedure for Skin Permeation Measurement

Franz diffusion cell experiments were used to analyze flux rates of varying foamable formulations across a substrate membrane. Franz diffusion cells are a common and well known method for measuring transdermal flux rates. The general Franz cell procedure is described in Franz, T. J., Percutaneous absorption: on the relevance of in vitro data. J. Invest. Derm., 64:190-195 (1975).

In the present Examples, Franz cells with a 3-ml receptor well volume were used with split thickness cadaver skin (0.015"-0.018", AlloSource) or Dermatomed porcine skin. The donor well had an area of about 0.55 cm². The receptor wells were filled with isotonic phosphate-buffered saline (PBS) doped with 0.01% sodium azide. The receptor wells of the Franz cells were maintained at 37° C. (the temperature on the surface of the skin is often about 32° C.) in a stirring dry block with continual agitation via a stir bar. The flanges of the Franz cells were coated with vacuum grease to ensure a complete seal and were clamped together with uniform pressure using a pinch clamp (SS #18 VWR 80073-350).

Porcine skin pieces were obtained from Lampire Biological Laboratories, Inc., Pipersville, Pa. Porcine skins were collected immediately following animal sacrifice, and the hairs were trimmed with clippers. Larger pieces of excess fat were removed with a filet knife. The skin was then trimmed to a set thickness of some 2 mm, cut into individual pieces, wrapped in aluminum foil, frozen, shipped, and stored at −78° C. Prior to use, the skin pieces were allowed to thaw, in air, to room temperature. Before use, the skin was dermatomed to a thickness of 0.5 to 1 mm and cut into circular pieces of an appropriate size prior to mounting in the FDC.

After the Franz cells were assembled, the skin was allowed to pre-hydrate for 45 minutes with PBS. The PBS was then removed and an appropriate amount of formulation was added to the skin. The dosing level was 3 µl per cell (~5.5 µl/cm²). The receptor wells were maintained at 37° C. (temperature on the surface of the skin is about 30° C.) in a stirring block with continual agitation via a stir bar. Samples were drawn from the receptor wells at varying time points. Measurements were made in six-fold replicates. The concentration of diclofenac in the samples was then analyzed using high-performance liquid chromatography.

Data Analysis

The cumulative amount of diclofenac transported across intact porcine skin or human cadaver skin at 4 h, 21 h, and 24 h was computed using in house software. In each experiment, the enhancement ratio of diclofenac delivery from the formulations over Pennsaid® was calculated at the 24 h time point as follows:

$$\text{Enhancement Ratio }(ER) = \frac{\text{Cumulative amount of } diclofenac \text{ delivered from test formulation}}{\text{Cumulative amount of } diclofenac \text{ delivered from } Pennsaid®}$$

Both the cumulative diclofenac delivery at the 24-hour time point and enhancement ratio is included in the tables below. A difference equal or greater than 20% in enhancement ratio over Pennsaid® is considered a meaningful difference. If the difference between the test formulation and the Pennsaid® control is within 20%, it is concluded that the diclofenac delivery from the test formulation has no demonstrated advantage over Pennsaid®.

Results

As illustrated in FIGS. 23 to 26, the inventive formulations (P100223, P100118, P100201) performed equally or better than the comparator (Pennsaid®).

Foaming Studies

The inventive formulations were additionally tested for foam stability. Results of the foam stabilization study (Table 5 below) from various combinations of surfactants and steroids showed that the combination of Brij and cholesterol (P100118-02) produced similar foam stability as the combination of Brij, cholesterol and SDBS (P100118-01). See FIGS. 23-26. Both P100118-01 and P100118-02 produced stable foams with the greatest foam heights suggesting that combinations of Brij 30, cholesterol and SDBS can produce stable foams. Furthermore, it appears that cholesterol is an effective foam stabilizer. Brij-containing formulations without cholesterol (P100118-03 and P100118-05) showed a rapid reduction in foam heights when compared to Brij-containing formulations with cholesterol. The lowest foam height was observed with formulation P100118-04, which does not contain Brij. Comparison of the foam heights between formulations P100118-01 and P100118-04, P100118-06, and P100118-07 strongly suggests that Brij is essential for foam formation from the DMSO base formulation.

TABLE 5

Foam Stability of Foamable DMSO Base Solutions containing Various Combinations of Surfactants and Steroids

| Formulation | Foam Heights (mm) at Different Time point | | | | | | |
|---|---|---|---|---|---|---|---|
| | 0 min | 2 mins | 5 mins | 30 mins | 60 mins | 120 mins | 180 mins |
| P100118-01 | 108.2 | 95.2 | 86.0 | 73.0 | 66.3 | 63.7 | 58.2 |
| P100118-02 | 107.7 | 95.5 | 86.2 | 69.3 | 64.8 | 58.2 | 55.2 |
| P100118-03 | 62.3 | 42.5 | 13.7 | 0.0 | 0.0 | 0.0 | 0.0 |
| P100118-04 | 5.3 | 5.8 | 3.7 | 4.2 | 2.7 | 1.5 | 0.0 |
| P100118-05 | 58.7 | 33.0 | 8.2 | 0.0 | 0.0 | 0.0 | 0.0 |
| P100118-06 | 0.0 | 0.0 | 0.0 | 0.0 | 0.0 | 0.0 | 0.0 |
| P100118-07 | 0.0 | 0.0 | 0.0 | 0.0 | 0.0 | 0.0 | 0.0 |
| P100118-08* | 0.0 | 0.0 | 0.0 | 0.0 | 0.0 | 0.0 | 0.0 |

*Base Solution

Example 6

Foam Stabilization and Permeation Studies, P100310 Series

A second set of formulations includes combinations of Brij 30, Brij 78, cholesterol, and sodium laureth sulfate (SLES); formulation compositions of these formulations are presented in Table 6 below.

TABLE 6

Formulation Composition of Foamable DMSO Base Solutions Containing Brij 30 and 78, Cholesterol, and SLES

| Ingredients | Formulations (w/w %) | | | | | | | | |
|---|---|---|---|---|---|---|---|---|---|
| | P100310-01 | P100310-02 | P100310-03 | P100310-04 | P100310-05 | P100310-06 | P100310-07 | P100310-08 | P100310-09 |
| DMSO Base | 98 | 98.05 | 98.1 | 98.05 | 98.1 | 98.15 | 98.1 | 98.15 | 98.2 |
| Brij 30 | 1 | 1 | 1 | 1 | 1 | 1 | 1 | 1 | 1 |
| Cholesterol | 0.15 | 0.1 | 0.05 | 0.15 | 0.1 | 0.05 | 0.15 | 0.1 | 0.05 |
| SLES | 0.15 | 0.15 | 0.15 | 0.1 | 0.1 | 0.1 | 0.05 | 0.05 | 0.05 |
| Brij 78 | 0.7 | 0.7 | 0.7 | 0.7 | 0.7 | 0.7 | 0.7 | 0.7 | 0.7 |

Foams were produced with a Rexam M3 foaming dispenser after the foam head was primed four times, after which the foam was dispensed to back of a volunteer's hand. The foam was considered to have collapsed when liquid started to appear at the base of the foam (leak). The following scale was used to measure collapse of foams:

3=No leak; 2=slight leak; 1=leak

Figure 27:
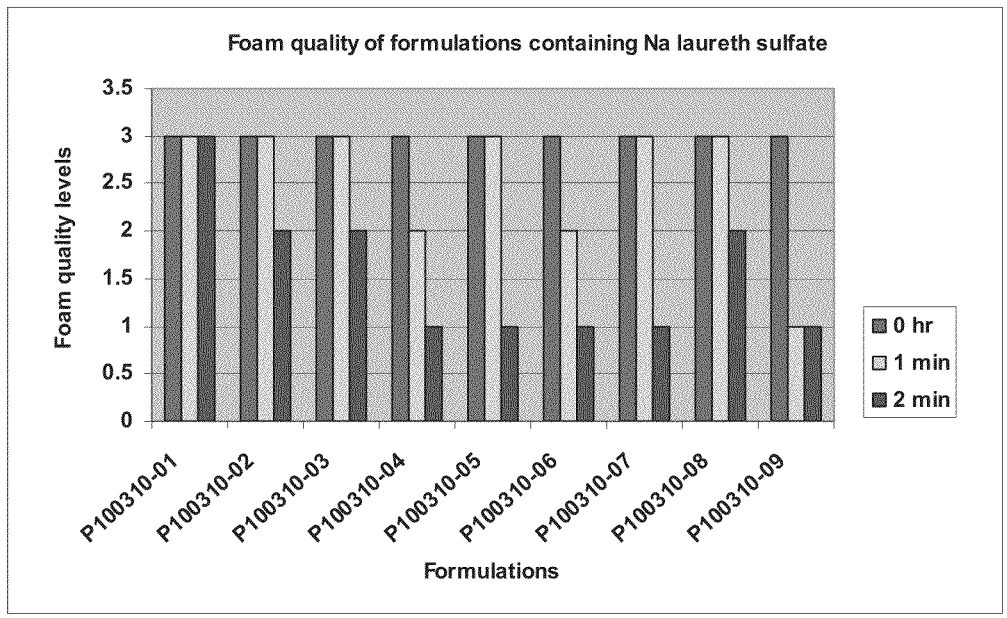
FIG. 27 illustrates the foam stability of a series of formulations (P100310) over two minutes following dispensing from a Rexam M3 foamer on the back of a volunteer's hand.

Results are presented in Table 7 and FIG. 27.

It appears that formulations P100310-01, P100310-02, P100310-03, P100310-07 and P100310-08 produced stable foams when dispensed from the Rexam M3 foaming dispenser. P100310-01 produced the most stable foam that did not collapse after 2 minutes. The ranking order of foam stability is P100310-01>P100310-02=P100310-03=P100310-08>P100310-04=P100310-05=P100310-06=P100310-07=P100310-09.

non-ionic surfactant Brij 30. Stable foams with a collapse time greater than 2 minutes were obtained from DMSO base formulation that contains a combination of non-ionic surfactants (Brij 30 and Brij 78), a steroid (cholesterol) and an anionic surfactant (SLES or SDBS) when dispensed from the Rexam M3 foaming dispenser. Both SDBS and SLES are listed on the FDA Inactive Ingredient List (IIG) for topical use; however, SDBS is listed for use in wash off products and SLES is listed for washed off and non-washed off products. Since Pennsaid® is indicated for non-wash off use, SLES was considered as the preferred anionic surfactant for further evaluation.

Based on the stability of the foam dispensed from the Rexam M3 foaming dispenser and the ease of collapsing the foam upon spreading, four foamable formulations with the combination of non-ionic surfactants (Brij 30 and Brij 78), a

TABLE 7

Foam Stability of P 100310 Series of Formulations over Two minutes
Following Dispensing with Rexam M3 Foamer on the Hand of a Volunteer

| | Foam Quality Scale | | | | | | | | |
|---|---|---|---|---|---|---|---|---|---|
| Time (min) | P100310-01 | P100310-02 | P100310-03 | P100310-04 | P100310-05 | P100310-06 | P100310-07 | P100310-08 | P100310-09 |
| 0 hr | 3 | 3 | 3 | 3 | 3 | 3 | 3 | 3 | 3 |
| 1 min | 3 | 3 | 3 | 2 | 3 | 2 | 3 | 3 | 1 |
| 2 min | 3 | 2 | 2 | 1 | 1 | 1 | 1 | 2 | 1 |

In a second assessment, foam was dispensed to the back of a volunteer's hand from the Rexam M3 dispenser and was gently spread with one stroke. The following scale was used to measure collapse of the foam after spreading:

5=hard foam; 4=light foam; 3=very light foam; 2=slightly light foam; 1=no foam

Figure 28:
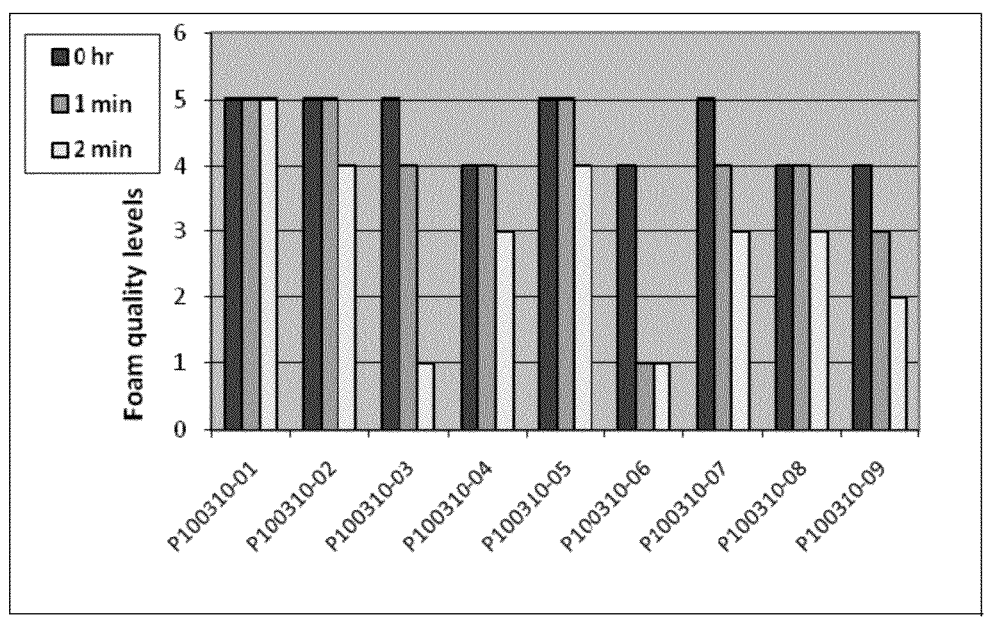
FIG. 28 illustrates the foam quality of P100310 sSeries formulations after spreading.

The formulations P100310-03 and P100310-06 were completely collapsed after 2 minutes. The ranking order of foam stability was P100310-01>P100310-02=P100310-06>P100310-04>P100310-07=P10310-08>P100310-03=P100310-06. Results are presented in Table 8 and FIG. 28. Pictures of the foams are included in FIGS. 42 through 50.

steroid (cholesterol) and an anionic surfactant (SLES) were identified, i.e., P100310-01, P100310-03, P100310-07 and P100310-08. Each of these four formulations contains the same concentration of Brij 30 and Brij 78, but different concentrations of cholesterol and SLES. Formulation P100310-01 is considered too stable since it did not collapse easily after spreading on the skin. Formulations P100310-03, P100310-07, and P100310-08 have similar foam stability characteristics when dispensed onto the skin. However, formulation P100310-03 collapses much more readily than P100310-07 and P100310-08 after the formulation is spread across the application site.

TABLE 8

Foam Stability of P100310 Series of Formulation over Two Minutes After Spreading

| | Foam quality of formulations | | | | | | | | |
|---|---|---|---|---|---|---|---|---|---|
| Time (min) | P100310-01 | P100310-02 | P100310-03 | P100310-04 | P100310-05 | P100310-06 | P100310-07 | P100310-08 | P100310-09 |
| 0 hr | 5 | 5 | 5 | 4 | 5 | 4 | 5 | 4 | 4 |
| 1 min | 5 | 5 | 4 | 4 | 5 | 1 | 4 | 4 | 3 |
| 2 min | 5 | 4 | 1 | 3 | 4 | 1 | 3 | 3 | 2 |

Conclusions on Foam Stabilization Studies

Figure 29:
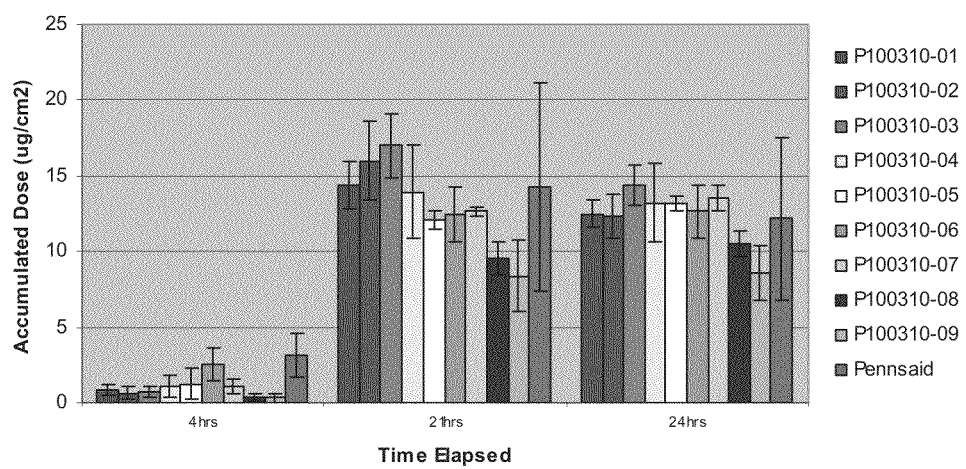
FIG. 29 illustrates diclofenac sodium permeation data for P100310 series formulations (Franz diffusion cell, human cadaver skin).

Thickeners including hydroxyethyl cellulose, polyvinylpyrrolidone, polyvinyl alcohol, poloxamer 407, cetostearyl alcohol, cetyl alcohol, hydroxypropyl cellulose, hydroxypropylmethyl cellulose, oleyl alcohol, glycerine monoricinoleate, glycerine monolaurate, glycerine monosterate, glycerine palmitate and lecithin did not stabilize foams produced from the DMSO base formulation containing In vitro Permeation Studies The in vitro diclofenac delivery results for the P100310 series formulations are presented in Table 9 and in FIG. 29. A modified version of the procedure set out in Example 5 was used. Based on the enhancement ration results, all P100310 series formulations showed equivalent diclofenac delivery relative to Pennsaid®.

TABLE 9

In Vitro Diclofenac Delivery from P100310 Series Foamable Formulations

Cumulative Amount of Diclofenac ($\mu g/cm^2$; avg ± sem)

| Time | P100310-01 | P100310-02 | P100310-03 | P100310-04 | P100310-05 | P100310-06 | P100310-07 | P100310-08 | P100310-09 | Pennsaid ® |
|---|---|---|---|---|---|---|---|---|---|---|
| 4 hrs | 0.83 ± 0.36 | 0.65 ± 0.40 | 0.73 ± 0.33 | 1.11 ± 0.73 | 1.26 ± 1.04 | 2.53 ± 1.03 | 1.09 ± 0.50 | 0.40 ± 0.22 | 0.32 ± 0.32 | 3.12 ± 1.43 |
| 21 hrs | 14.36 ± 1.54 | 16.00 ± 2.58 | 16.98 ± 2.16 | 13.95 ± 3.10 | 12.09 ± 0.59 | 12.42 ± 1.80 | 12.66 ± 0.28 | 9.49 ± 1.09 | 8.38 ± 2.35 | 14.30 ± 6.89 |
| 24 hrs | 12.49 ± 0.90 | 12.32 ± 1.44 | 14.34 ± 1.33 | 13.22 ± 2.63 | 13.17 ± 0.48 | 12.63 ± 1.73 | 13.50 ± 0.83 | 10.49 ± 0.88 | 8.59 ± 1.84 | 12.18 ± 5.39 |
| ER | 1.03 | 1.01 | 1.18 | 1.09 | 1.08 | 1.04 | 1.11 | 0.86 | 0.79 | 1.00 |

In summary, both P100223 (FIGS. 19-22, 24-25) and P100310 series formulations delivered equivalent amount of diclofenac as Pennsaid®. However, the foam characterization studies showed that P100310 series foamable formulations generated stable foams that are easy to spread.

Example 7

Formulation Studies of P100310-01

A further formulation optimization study was carried out with P100310-01 to determine the optimal concentrations of Brij 30, Brij 78, cholesterol, and SLES.

Formulation P100310-01 was coded as the P100323 series. The design of the formulation composition is presented in Table 10. Preliminary foam quality studies were conducted using the vortex mixing method and diclofenac delivery studies performed using with Franz diffusion cell system as described in Example 5.

TABLE 10

Formulation Compositions of the P100323 Series

| Ingredients (w/w %) | P100323-01[a] | P100323-02 | P100323-03 | P100323-04 | P100323-05 | P100323-06 |
|---|---|---|---|---|---|---|
| DMSO Base | 98 | 99 | 98.15 | 98.15 | 98.7 | 98 |
| Brij 30 | 1 | 0 | 1 | 1 | 1 | 0.7 |
| Cholesterol | 0.15 | 0.15 | 0 | 0.15 | 0.15 | 0.15 |
| Sodium laureth sulfate | 0.15 | 0.15 | 0.15 | 0 | 0.15 | 0.15 |
| Brij 78 | 0.7 | 0.7 | 0.7 | 0.7 | 0 | 1 |

[a] = P100310-01

Foam Stability and Diclofenac Delivery of the P100323 Series Formulations

Figure 30:
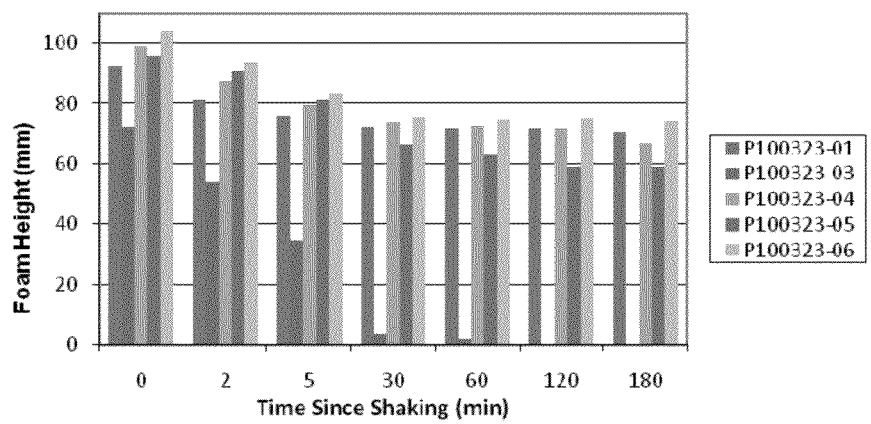
FIG. 30 illustrates foam stability assessed by the vortex mixing method using P100323 series formulations after 30 seconds of vortex mixing.

Results (FIG. 30) from the preliminary foaming studies indicate that P100323-03 produced the least stable foam, suggesting that cholesterol improves foam stability. All other formulations showed similar foam stability. Varying the Brij 30 concentration from 1.0 w/w % to 0.7 w/w %, Brij 78 concentration from 0 w/w % to 0.7 w/w % and 1.0 w/w %, and SLES concentration from 0 w/w % to 0.15 w/w % did not impact foam stability when assessed by the vortex mixing method.

Figure 31:
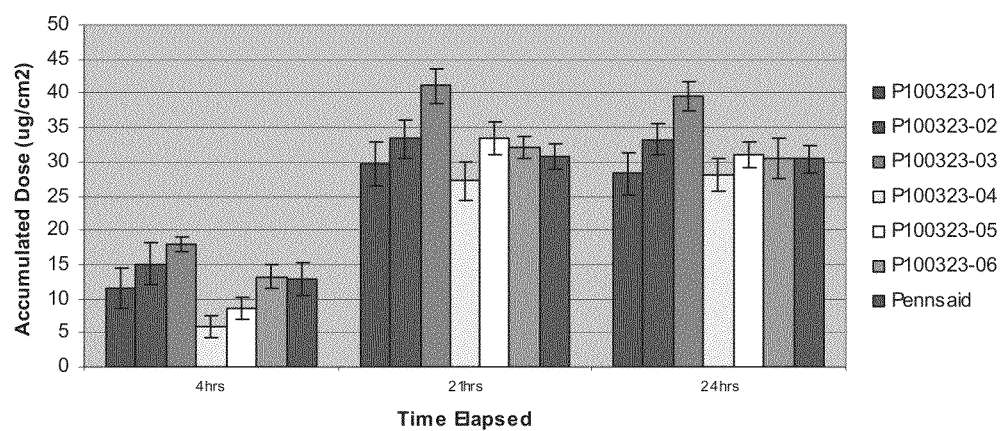
FIG. 31 illustrates in vitro diclofenac delivery from P100323 Formulations (Franz diffusion cells, human cadaver skin).

The results for the Franz diffusion cell delivery studies are presented in FIG. 31 and Table 11 below. Based on the enhancement ratios, all formulations with the exception of P100323-03 showed equivalent diclofenac delivery relative to Pennsaid®. Pictures for foam stability are presented in FIGS. 42 to 50.

TABLE 11

In Vitro Diclofenac Delivery across Intact Human Cadaver Skin from P100323 Series Formulations Formulations/Cumulative Amount of Diclofenac ($\mu g/cm^2$; avg ± sem)

| Time | P100323-01 | P100323-02 | P100323-03 | P100323-04 | P100323-05 | P100323-06 | Pennsaid ® |
|---|---|---|---|---|---|---|---|
| 4 hrs | 11.57 ± 2.97 | 15.08 ± 3.16 | 17.86 ± 1.07 | 5.96 ± 1.65 | 8.58 ± 1.52 | 13.17 ± 1.68 | 12.90 ± 2.47 |
| 21 hrs | 29.67 ± 3.10 | 33.30 ± 2.81 | 41.08 ± 2.53 | 27.20 ± 2.88 | 33.37 ± 2.34 | 32.08 ± 1.72 | 30.76 ± 1.94 |
| 24 hrs | 28.21 ± 2.97 | 33.23 ± 2.26 | 39.58 ± 2.08 | 28.09 ± 2.47 | 30.93 ± 1.91 | 30.52 ± 2.92 | 30.42 ± 2.06 |
| ER | 0.93 | 1.09 | 1.30 | 0.92 | 1.02 | 1.00 | 1.00 |

Conclusions from the P100323 Series Study

The absence of cholesterol in these formulations resulted in poor foam stability. Varying the concentrations of Brij 30, Brij 78 and SLES did not change foam stability characteristics. However, assessment of foam characteristics by the Rexam M3 foaming dispenser, a more relevant assessment, was not conducted except for formulation P100323-01 which showed good foam stability. All formulations with the exception of P100323-03 (no cholesterol) showed comparable diclofenac delivery to Pennsaid®. Formulation P100323-01 (P100310-01) delivered diclofenac across intact human skin equivalent to Pennsaid®, and it formed a stable foam when dispensed from the Rexam M3 foaming dispenser.

Example 8

Formulation Studies of P100310-03, P100312 Series

A further formulation optimization study were carried out with P100310-03 to determine the optimal concentrations of Brij 30, Brij 78, cholesterol, and SLES.

Formulation P100310-03 was coded as the P100312 series. Formulation compositions are presented in Table 12. Preliminary foam quality studies were conducted using both the vortex mixing method and from a Rexam M3 foaming dispenser. Diclofenac delivery from these formulations was also assessed using Franz diffusion cells as described in Example 5.

TABLE 12

Formulation Compositions of the P100312 Series

| Ingredients (w/w %) | P100312-01[a] | P100312-02 | P100312-03 | P100312-04 | P100312-05 | P100312-06 |
|---|---|---|---|---|---|---|
| DMSO Base | 98.1 | 99.1 | 98.15 | 98.25 | 98.8 | 98.1 |
| Brij 30 | 1 | 0 | 1 | 1 | 1 | 0.7 |
| Cholesterol | 0.05 | 0.05 | 0 | 0.05 | 0.05 | 0.05 |
| Sodium laureth sulfate | 0.15 | 0.15 | 0.15 | 0 | 0.15 | 0.15 |
| Brij 78 | 0.7 | 0.7 | 0.7 | 0.7 | 0 | 1 |

[a] = P100310-03

Foam Stability and Diclofenac Delivery of the P100312 Series

Figure 32:
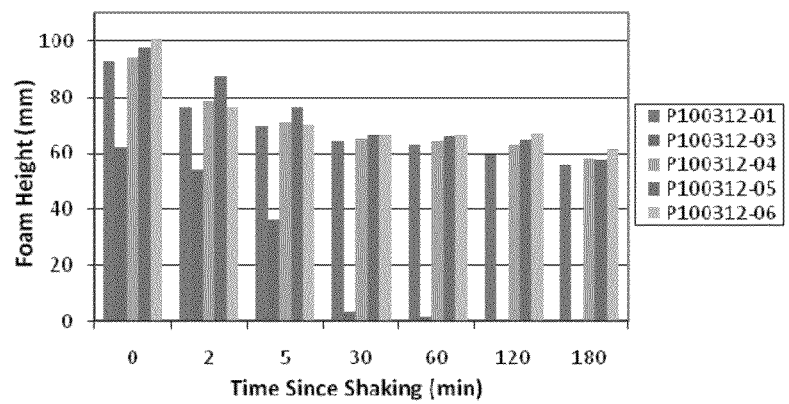
FIG. 32 illustrates foam stability assessed by the vortex mixing method using P100312 series formulations after 30 seconds of vortex mixing.

Results (FIG. 32) from the preliminary foaming studies using the vortex mixing method indicate that P100312-03 gave the least stable foam, suggesting that cholesterol improves foam stability. All other formulations showed similar foam stability. Varying Brij 30 concentration from 1.0 w/w % to 0.7 w/w %, Brij 78 concentration from 0 w/w % to 0.7 w/w % and 1.0 w/w, and SLES concentration from 0 w/w % to 0.15 w/w % did not have any impact on foam stability. Results from the foam stability study using the Rexam M3 foaming dispenser showed that P100312-01 yield the best foaming characteristics.

Pictures for foam stability tests are presented in FIGS. 51 to 55.

Figure 33:
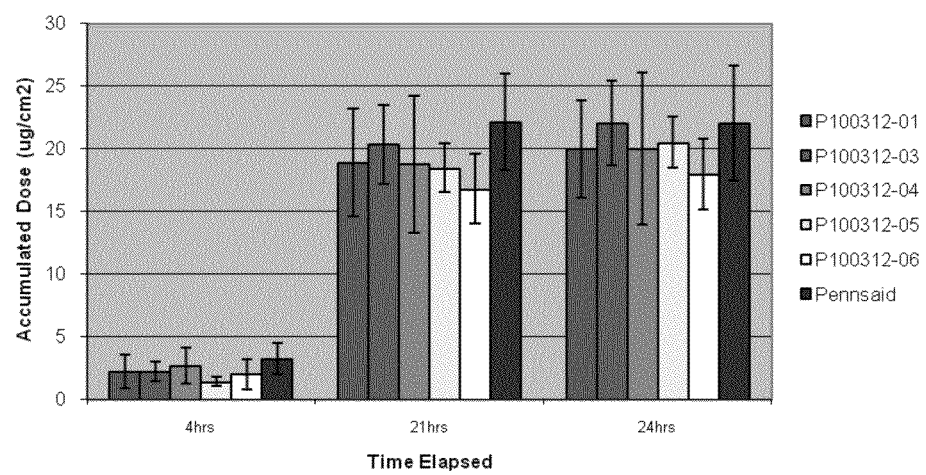
FIG. 33 illustrates diclofenac sodium permeation data for P100312 series formulations (Franz diffusion cell, human cadaver skin).

Results from the Franz diffusion cell studies are presented in FIG. 33 and Table 13. With the exception of P100312006, all other formulations in the series showed equivalent diclofenac delivery relative to Pennsaid®.

TABLE 13

Diclofenac Sodium Permeation of the P100312 Series

Formulations/Cumulative Amount of Diclofenac ($\mu s/cm^2$; avg ± sem)

| Time | P100312-01 | P100312-03 | P100312-04 | P100312-05 | P100312-06 | DMSO Base |
|---|---|---|---|---|---|---|
| 4 hrs | 2.21 ± 1.34 | 2.24 ± 0.74 | 2.67 ± 1.43 | 1.43 ± 0.39 | 2.02 ± 1.20 | 5.46 ± 1.72 |
| 21 hrs | 18.90 ± 4.30 | 20.33 ± 3.17 | 18.76 ± 5.48 | 18.47 ± 1.95 | 16.79 ± 2.79 | 24.45 ± 3.44 |
| 24 hrs | 19.99 ± 3.88 | 22.03 ± 3.40 | 20.01 ± 6.02 | 20.51 ± 2.06 | 17.95 ± 2.82 | 24.14 ± 3.78 |
| ER | 0.83 | 0.91 | 0.83 | 0.85 | 0.74 | 1.00 |

Conclusions from Studies of the P100312 Series Study

In these formulations, the absence of cholesterol results in poor foam stability. Varying the concentrations of Brij 30, Brij 78 and SLES did not change foam stability characteristics. Assessment of foam characteristics by the Rexam M3 foaming dispenser showed that P100312-01 has the best foam stability. All formulations with the exception of P100312-03 (no cholesterol) showed comparable diclofenac delivery to Pennsaid®. Formulation P100312-01 (P100310-03) has equivalent diclofenac delivery to Pennsaid®, and it formed a stable foam when dispensed from the Rexam M3 foaming dispenser.

Example 9

Formulation Studies of P100310-07, P100325 Series

A further formulation optimization study were carried out with P100310-07 to determine the optimal concentrations of Brij 30, Brij 78, cholesterol, and SLES.

Formulation P100310-07 was coded as the P100325 series. The formulation compositions are presented in Table 14. Preliminary foam quality studies were conducted using the vortex mixing method, and diclofenac delivery was assessed using Franz diffusion cells as described in Example 5.

TABLE 14

Formulation Compositions of the P100325 Series

Formulations

| Ingredients (w/w %) | P100325-01[a] | P100325-02 | P100325-03 | P100325-04 | P100325-05 | P100325-06 |
|---|---|---|---|---|---|---|
| DMSO Base | 98.1 | 99.1 | 98.25 | 98.15 | 98.8 | 98.1 |
| Brij 30 | 1 | 0 | 1 | 1 | 1 | 0.7 |
| Cholesterol | 0.15 | 0.15 | 0 | 0.15 | 0.15 | 0.15 |
| Sodium laureth sulfate | 0.05 | 0.05 | 0.05 | 0 | 0.05 | 0.05 |
| Brij 78 | 0.7 | 0.7 | 0.7 | 0.7 | 0 | 1 |

[a] = P100310-07

Foam Stability and Diclofenac Delivery of the P100325 Series

Figure 34:
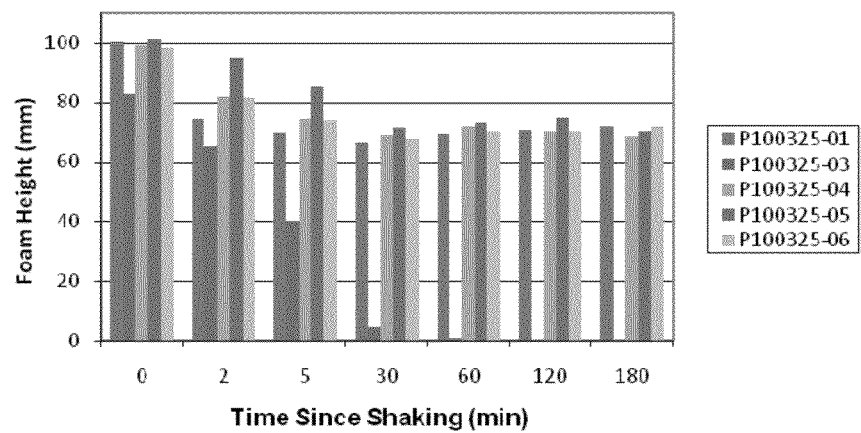
FIG. 34 illustrates foam stability assessed by the vortex mixing method using P100325 series formulations after 30 seconds of vortex mixing.

Results from the preliminary foaming studies (FIG. 34) indicate that P100325-03 produced the least stable foam, suggesting that cholesterol improves foam stability. All other formulations showed similar foam stability. Varying Brij 30 concentration from 1.0 w/w % to 0.7 w/w %, Brij 78 concentration from 0 w/w % to 0.7 w/w % and 1.0 w/w %, and SLES concentration from 0 w/w % to 0.05 w/w % did not have any impact on foam stability when assessed by the vortex mixing method.

Figure 35:
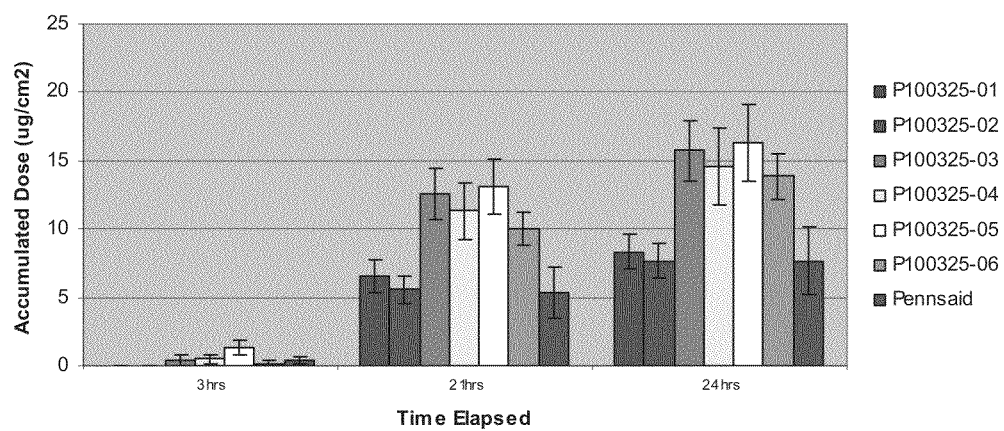
FIG. 35 illustrates diclofenac sodium permeation data for P100325 series formulations (Franz diffusion cell, human cadaver skin).

The results for the Franz diffusion cell permeation studies are presented in FIG. 35 and Table 15. Formulations P100325-01 and P100325-02 showed equivalent diclofenac delivery relative to the Pennsaid® control. Formulations P100325-03, P100325-04, P100325-05 and P100325-06 showed higher diclofenac delivery than the Pennsaid® control.

TABLE 15

Diclofenac Sodium Permeation of the P100325 Series

Formulations/Cumulative Amount of Diclofenac ($\mu g/cm^2$; avg ± sem)

| Time | P100325-01 | P100325-02 | P100325-03 | P100325-04 | P100325-05 | P100325-06 | Pennsaid ® |
|---|---|---|---|---|---|---|---|
| 4 hrs | 0.00 ± 0.00 | 0.00 ± 0.00 | 0.42 ± 0.42 | 0.48 ± 0.31 | 1.34 ± 0.57 | 0.20 ± 0.20 | 0.39 ± 0.27 |
| 21 hrs | 6.54 ± 1.17 | 5.59 ± 0.99 | 12.57 ± 1.90 | 11.30 ± 2.05 | 13.12 ± 1.98 | 10.00 ± 1.23 | 5.31 ± 1.90 |
| 24 hrs | 8.35 ± 1.27 | 7.67 ± 1.22 | 15.72 ± 2.22 | 14.62 ± 2.79 | 16.34 ± 2.81 | 13.89 ± 1.68 | 7.65 ± 2.45 |
| ER | 1.09 | 1.00 | 2.05 | 1.92 | 2.14 | 1.82 | 1.00 |

Conclusions from the P100325 Series Study

In these formulations, the absence of cholesterol results in poor foam stability. Varying the concentrations of Brij 30, Brij 78 and SLES did not change foam stability characteristics. However, assessment of foam characteristics by the Rexam M3 foaming dispenser was not performed except for formulation P100325-01 which demonstrated good foam stability. Formulations P100325-01 and P100325-02 showed equivalent diclofenac delivery relative to Pennsaid®; all other formulations showed higher diclofenac sodium delivery than Pennsaid®. Formulation P100325-01 (P100310-07) has equivalent diclofenac delivery relative to Pennsaid®, and it formed a stable foam when dispensed from the Rexam M3 foaming dispenser.

Example 10

Formulation Optimization Studies of P100310-08, P100324 Series

A further formulation optimization study were carried out with P100310-08 to determine the optimal concentrations of Brij 30, Brij 78, cholesterol, and SLES.

The formulation P100310-08 was coded as the P100324 series. The formulation composition is presented in Table 16. Preliminary foam quality studies were conducted using the vortex mixing method, and diclofenac delivery was assessed using Franz diffusion cells was assessed.

TABLE 16

Formulation Composition for the P100324 Series

| Ingredients (w/w %) | P100324-01[a] | P100324-02 | P100324-03 | P100324-04 | P100324-05 | P100324-06 |
|---|---|---|---|---|---|---|
| DMSO Base | 98.15 | 99.15 | 98.25 | 98.2 | 98.85 | 98.15 |
| Brij 30 | 1 | 0 | 1 | 1 | 1 | 0.7 |
| Cholesterol | 0.1 | 0.1 | 0 | 0.1 | 0.1 | 0.1 |
| Sodium laureth sulfate | 0.05 | 0.05 | 0.05 | 0 | 0.05 | 0.05 |
| Brij 78 | 0.7 | 0.7 | 0.7 | 0.7 | 0 | 1 |

Foam Stability and Diclofenac Delivery for the P100324 Series

Figure 36:
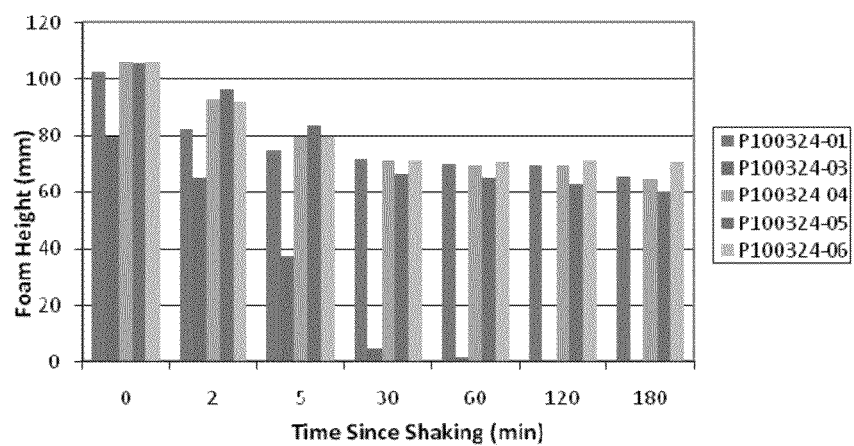
FIG. 36 illustrates foam stability assessed by the vortex mixing method using P100324 series formulations after 30 seconds of vortex mixing.

Results (FIG. 36) from the preliminary foaming studies indicate that P100324-03 produced the least stable foam, suggesting that cholesterol improves foam stability. All other formulations showed similar foam stability. Varying Brij 30 concentrations from 1.0 w/w % to 0.7 w/w %, Brij 78 from 0 w/w % to 0.7 w/w % and 1.0 w/w %, SLES from 0 w/w % to 0.05 w/w %, did not have any impact on foam stability when assessed by the vortex method.

Figure 37:
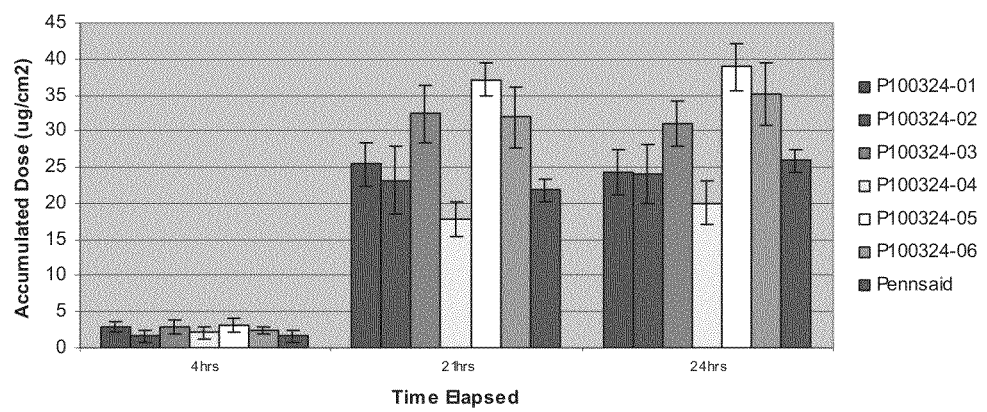
FIG. 37 illustrates diclofenac sodium permeation data for P100324 series formulations (Franz diffusion cell, human cadaver skin).

Results from the Franz diffusion cell studies are presented in FIG. 37 and Table 17. All formulations with the exception of P100324-05 and P100324-06 showed equivalent diclofenac delivery relative to Pennsaid®. Formulations P100324-05 and P100324-06 showed higher diclofenac delivery as compared to Pennsaid®.

TABLE 17

Diclofenac Delivery for the P100324 Series Formulations

Cumulative Amount of Diclofenac ($\mu g/cm^2$; avg ± sem)

| Time | P100324-01[a] | P100324-02 | P100324-03 | P100324-04 | P100324-05 | P100324-06 | Pennsaid® |
|---|---|---|---|---|---|---|---|
| 4 hrs | 2.87 ± 0.74 | 1.60 ± 0.90 | 2.94 ± 0.93 | 2.09 ± 0.81 | 3.20 ± 0.93 | 2.40 ± 0.53 | 1.63 ± 0.89 |
| 21 hrs | 25.42 ± 3.09 | 23.15 ± 4.68 | 32.38 ± 4.05 | 17.85 ± 2.43 | 37.17 ± 2.30 | 31.94 ± 4.15 | 21.84 ± 1.52 |
| 24 hrs | 24.33 ± 3.19 | 24.16 ± 4.08 | 31.12 ± 3.12 | 20.05 ± 2.96 | 38.94 ± 3.20 | 35.11 ± 4.26 | 25.89 ± 1.63 |
| ER | 0.94 | 0.93 | 1.20 | 0.77 | 1.50 | 1.36 | 1.00 |

[a] = P100310-08

Conclusions from the P100324 Series Study

In these formulations, the absence of cholesterol results in poor foam stability. Varying the concentrations of Brij 30, Brij 78 and SLES did not change foam stability characteristics. However, assessment of foam characteristics by the Rexam M3 foaming dispenser was not conducted, except for formulation P100324-01, which showed good foam stability. All formulations except for P100324-05 and P100324-06 showed equivalent diclofenac accumulation relative to Pennsaid®. Formulation P100324-01 (P100310-08) delivered equivalent amount of diclofenac relative to Pennsaid®, and it formed stable foam when dispensed from the Rexam M3 foaming dispenser.

Example 11

General Laboratory Batch Manufacturing Process

The following small-scale, 100-g laboratory batch manufacturing process was established.

Diclofenac sodium, Brij 30, Brij 78, SLES, ethanol, and water are added to a suitable container and mixed until dissolved. DMSO, propylene glycol, glycerine, and cholesterol are added to a second suitable container and mixed until homogeneous. The diclofenac/Brij solution is added to the second container and mixed until homogenous. The combined mixture is stirred overnight at room temperature. The mixture is then filtered through a 0.2 micrometer pore-size filter and added into suitable containers.

Example 12

Comparison of Four Selected P100310 Formulations

Diclofenac Delivery

The diclofenac deliveries from the P100310 formulations were assessed using Franz diffusion cell and human cadaver skin. Pennsaid® was included as a control in this study. Compositions of the P100310 formulations are presented in the table below.

TABLE 18

Composition of Selected P100310 Formulations

% w/w composition

| Excipient | P100310-01 or P100323-01 | P100310-03 or P100312-01 | P100310-07 or P100325-01 | P100310-08 or P100324-01 |
|---|---|---|---|---|
| DMSO Base | 98.00 | 98.10 | 98.10 | 98.15 |
| Brij 30 | 1.00 | 1.00 | 1.00 | 1.00 |
| Brij 78 | 0.7 | 0.7 | 0.7 | 0.7 |
| Cholesterol | 0.15 | 0.05 | 0.15 | 0.10 |
| SLES | 0.15 | 0.15 | 0.05 | 0.05 |

Figure 38:
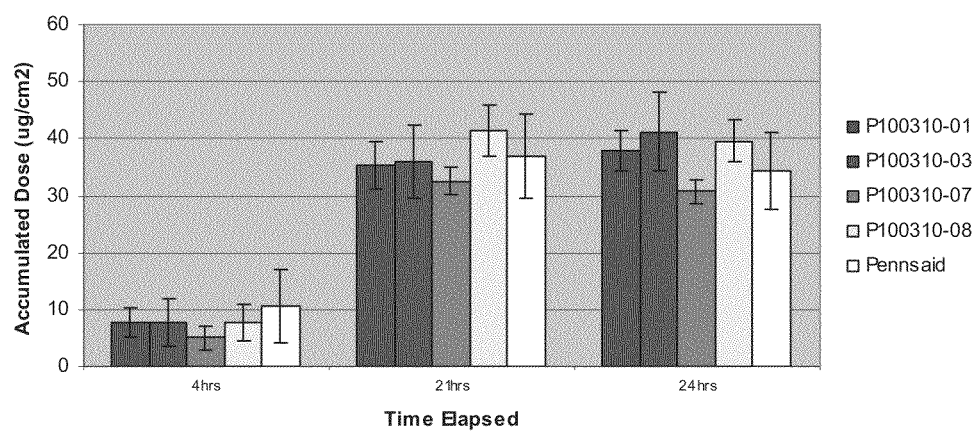
FIG. 38 illustrates a comparison of the diclofenac delivery among four selected formulations (P100310).

The results for the Franz diffusion cell study are presented in FIG. 38 and Table 19. The diclofenac delivery was similar among the four formulations; all four formulations showed equivalent diclofenac delivery relative to Pennsaid®.

TABLE 19

Comparative Diclofenac Delivery from the Selected P100310 Formulations

| | Cumulative Amount of Diclofenac ($\mu g/cm^2$; avg ± sem) | | | | |
|---|---|---|---|---|---|
| Time | P100310-01 | P100310-03 | P100310-07 | P100310-08 | Pennsaid ® |
| 4 hrs | 7.68 ± 2.45 | 7.68 ± 4.30 | 4.98 ± 2.04 | 7.66 ± 3.30 | 10.63 ± 6.39 |
| 21 hrs | 35.22 ± 4.14 | 35.97 ± 6.41 | 32.55 ± 2.54 | 41.45 ± 4.47 | 36.81 ± 7.33 |
| 24 hrs | 37.80 ± 3.48 | 41.17 ± 6.88 | 30.78 ± 2.10 | 39.59 ± 3.81 | 34.36 ± 6.77 |
| ER | 1.10 | 1.20 | 0.90 | 1.15 | 1.00 |

Physicochemical Parameters of Selected P100310 Formulations

The physicochemical properties, pH and specific gravity of the four formulations were measured and compared to Pennsaid® and are presented in the table below. Further measurements of specific gravity may be carried out using a calibrated picnometer using techniques generally known in the art. Both pH and specific gravity for each of the four formulations selected are comparable to each other, and are within the specifications described for Pennsaid®.

TABLE 20

Physicochemical Properties of P100310 Formulations

| Formulation | pH[a] ± SD | Specific Gravity[b] (g/mL) ± SD |
|---|---|---|
| P100310-01 | 8.38 ± 0.03 | 1.045 ± 2.01 |
| P100310-03 | 8.42 ± 0.07 | 1.046 ± 2.41 |
| P100310-07 | 8.48 ± 0.06 | 1.043 ± 1.3 |
| P100310-08 | 8.52 ± 0.08 | 1.040 ± 0.54 |
| Pennsaid ® | 8.0-9.5 | 1.030-1.110 |

[a]pH was measured with a Fisher AR 15 pH meter;
[b]was determined with 5 mL volumetric flask Conclusions The development of a foamable DMSO formulation has been accomplished by (i) combining a DMSO base solution with suitable surfactants and a foam stabilizer, and (ii) dispensing from a suitable foam-dispensing pump. In this study, stable foams with a collapse time greater than two minutes when dispensed from a Rexam M3 foaming dispenser were obtained from the combination of Brij 30, Brij 78, cholesterol and SLES.

Four formulations of interest were identified: P100310-01, P100310-03, P100310-07 and P100310-08. These formulations have the same concentration of Brij 30 (1.0 w/w %) and Brij 78 (0.7 w/w %) but different concentrations of cholesterol or SLES. The four formulations displayed equivalent diclofenac delivery relative to Pennsaid®, but with different foaming characteristics. Formulation P100310-01 was very stable and did not collapse quickly after application. Formulations P100310-03, P100310-07, and P100310-8 have similar foam stability characteristics following dispensing onto the skin surface. However, formulation P100310-03 collapses much more readily than P100310-07 and P100310-08 after the formulation is spread across the application site.

Formulation P100310-03 has several desirable properties, including:
  producing a foam after dispension from a suitable foaming device so that (i) before contacting the skin; the foam is stable for ≥2 mins before it starts to disintegrate (i.e., collapse); (ii) the foam should be spreadable; and (iii) the foam collapsed quickly when gently rubbed into the skin; and
  providing a diclofenac delivery equivalent to or better than the control Pennsaid®.

Example 13

General Procedures for Testing of Sprayable, Microstructured Ibuprofen Formulation A sprayable, microstructured ibuprofen formulation suitable for twice a day (b.i.d) dosing that achieves ≥two times the 12 hour accumulated flux of the comparator gel was investigated. The comparator gel IBUGEL® (ibuprofen 5% w/w gel) is a topical product marketed in the United Kingdom, Ireland and Luxembourg for the treatment of acute pain associated with soft-tissue injuries, sprains and strains.

Long-term storage stability of DMSO-free ibuprofen gel formulations demonstrated a possible interaction between ibuprofen and ethanol resulting in the production of Compound A, a degradant presumed to the ethyl ester of ibuprofen. The foam-type formulation was designed to have an improved stability profile while providing at least two-fold higher permeation of ibuprofen as compared to Ibugel.

Materials

Ibuprofen, USP is the active pharmaceutical ingredient (API) in these formulations. The API used for the experiments described in this application was sourced from Albemarle, USA and met the compendial requirements of USP. Ibuprofen [i.e., 2-(4-isobutylphenyl) propanoic acid] is a member of the propionic acid group of non-steroidal anti-inflammatory compounds. The ibuprofen used for the following studies was a racemic mixture.

Ibuprofen is a white to off-white powder, practically insoluble in water (<0.1 mg/ml), but readily soluble in organic solvents such as ethanol and acetone. The compound has a melting point range of 75 to 77° C., a pKa value of 4.91 and a log P value of 3.6 (DrugBank: a comprehensive resource for in silico drug discovery and exploration. Wishart D S, Knox C, Guo A C, Shrivastava S, Hassanali M, Stothard P, Chang Z, Woolsey J. Nucleic Acids Res. 2006 Jan. 1; 34 (Database issue):D668-72. PMID: 16381955).

Table 21 provides a list of the materials used for the formulation screening activities described in this report and the sourcing information for the materials.

TABLE 21

Materials used in Formulation Screening Experiments for Ibuprofen (5% w/w) Foam Formulations

| Chemical name | Abbreviation | CAS Number | Source |
|---|---|---|---|
| Ibuprofen | — | 15687-27-1 | Albemarle |
| Dimethyl sulfoxide | DMSO | 67-68-5 | Sigma Aldrich |
| Ethanol | — | 64-17-5 | Sigma-Aldrich |
| Water | — | — | — |

TABLE 21-continued

Materials used in Formulation Screening Experiments for Ibuprofen (5% w/w) Foam Formulations

| Chemical name | Abbreviation | CAS Number | Source |
|---|---|---|---|
| Propylene glycol | PG | 57-55-6 | Unilever |
| Glycerin | — | 56-81-5 | J T Baker |
| Polyoxyl stearyl ether | Brij 78 | 9005-00-9 | Acros |
| Polyoxyl lauryl ether | Brij 30 | 9002-92-0 | Spectrum |
| Sodium lauryl sulfate | SLS | 151-21-5 | Sigma Aldrich |
| Sodium laureth sulfate | SLES | NR (Not Recorded) | Stepan |
| Sodium carbonate | | 497-19-8 | Spectrum |
| Cocoamidopropyl betaine (Amphosol® HCG) | Amphosol | 61789-40-0 | Stepan |
| Diethylene glycol monoethyl ether (Transcutol®) | Transcutol | 111-90-0 | Fluka Chemicals |
| Disodium cocoamphodiacetate | DCAM | 68650-39-5 | Rhodia |
| Lactic Acid | — | 50-21-5 | Sigma Aldrich |
| Triethyl citrate | TEC | 77-93-0 | Spectrum, Sigma Aldrich, SAFC |
| Methyl paraben | — | 99-76-3 | Spectrum |
| Propyl paraben | — | 94-13-3 | Sigma Aldrich |
| Cholesterol | — | 57-88-5 | Sigma Aldrich, J T Baker |
| Phosphate buffered saline | PBS | — | — |
| Hydroxypropyl cellulose (HY 121, HY 117) | HPC | 9004-64-2 | Spectrum, Hercules |
| Poly(ethylene oxide-co-Polypropylene oxide) | Poloxamer 407 | 9003-11-6 | Spectrum |
| Polyvinyl alcohol | PVA | 9002-89-5 | Sigma Aldrich |
| Human cadaver skin | — | — | Allosource (Centennial, CO, USA) |
| Porcine skin | — | — | Lampire Biological Laboratories (Pipersville, PA, USA) |

Equipment

High-performance liquid chromatography (HPLC) was conducted with an Agilent 1200 HPLC analytical system equipped with UV detector (Model G1313D DAD; Agilent Technologies, Waldbronn, Germany). The dermatome procedures were conducted with a Zimmer® electric dermatome (Zimmer Orthopaedic Products, Dover, Ohio 44622, USA) The other equipment used in the following procedures includes a Nichiryo 8100 Applicator (Nichiryo, Tokyo, Japan), Franz diffusion cells (FDC) 3 mL volume (Chemglass, Vineland, N.J., USA), anincubator (VWR Scientific Model 1565), and aHarris Classic Freezer (Model HLT-17V-85D14; Harris Manufacturing Co., Asheville, N.C., USA).

Skin Storage and Dermatome Procedure

Excised Yorkshire pig (Sus domestica) skin was provided by Lampire Biological Laboratories (Pipersville, Pa., USA). Human cadaver skin was provided by Allosource (Centennial, Colo., USA). Upon receipt, skin samples were frozen immediately and stored at Ca −80° C. until needed. Prior to use, skin was removed from the freezer and thawed at room temperature (ca. 45 minutes). Following thawing, skin pieces were dermatomed to a thickness of 0.8 to 1.0 mm using the procedure described in Example 5.

Franz Cell Set-up for In Vitro Permeability Studies

In vitro permeability studies were conducted using Franz diffusion cells (FDCs) as outlined in Example 5. Dermatomed porcine skin was used as the skin substrate. Human cadaver skin was used in the definitive flux experiments. The general procedure for these permeation experiments is described below.

Franz diffusion cells with a 3.3 ml receiver volume and 0.55 cm$^2$ cross sectional area were used. Receptor wells were filled with phosphate buffered saline (PBS) containing 0.01% sodium azide (used as a preservative). Sections of skin (~2×2 cm) were mounted on the receptor cells. The flanges of the FDCs were coated with vacuum grease to ensure a complete seal and clamped together with uniform pressure using a pinch clamp. Any excess skin was trimmed with a pair of stainless-steel scissors. After assembly of the FDCs, the skin was allowed to rehydrate for ca. 20 minutes. The test formulations were applied, and the FDC set-up was placed in an incubator at 32° C. The receptor fluid was continuously stirred and maintained at 32±0.5° C. throughout the experiments. Measurements for each formulation were carried out in 6-8 fold replicates.

Formulation Application and Analysis

Typically, 3 μl of the formulation was applied to the donor chamber using the Nichiryo sample applicator. The commercial formulation Ibugel (ibuprofen 5% w/w gel) was used as comparator and was also applied as a 3 μl dose to the skin surface in the donor chamber.

300 μL sample aliquots were drawn from the receptor sampling ports with a Hamilton-type injector. The sample volume was replaced with fresh PBS containing 0.01% sodium azide. Aliquots were typically withdrawn at 4, 21 and 24 hours after sample application, unless specifically indicated.

Aliquots of receptor fluid were analyzed by HPLC.

Data Analysis

The cumulative amounts of ibuprofen transported across porcine skin at 4 h, 21 h, and 24 h were computed. In each case, the enhancement in ibuprofen delivery from the test formulations over the control Ibugel formulation was calculated at the 24 h time point as follows:

$$\text{Enhancement ratio } (ER) = \frac{\text{Mean cumulative amount of ibuprofen delivered from test formulation } (\mu g/cm^2)}{\text{Mean cumulative amount of ibuprofen delivered from } Ibugel\ (\mu g/cm^2)}$$

For the purposes of this report, ER changes of less than 20% between formulations was considered to have no meaningful impact on permeability trends.

Formulation Preparation

Typically, formulations used in the permeability experiments were prepared as 5 to 10 g batches. The stability batches were prepared at 100-g scale using the same general procedure described below.

The formulation components were added to a vial and vortexed until a clear solution was obtained. In case of formulations that contained methyl and propyl paraben, these were added immediately after the ibuprofen and before addition of DMSO. Only formulations that were homogeneous by visual observation immediately prior to the permeability experiments were included in these studies.

Formulation Development

Initial formulation activities for ibuprofen topical formulation were focused on the development of various formulation types. During the development of these formulations, a stability concern arose related to the formation of an ibuprofen related degradant, Compound A. It was hypothesized that Compound A was the result of a reaction between the free acid form of ibuprofen with ethanol to form the corresponding ethyl ester. Formulation and stability studies with the early formulations indicated that the ester formation was pH-dependent with lower pHs showing a higher rate of ester formation. The potential stability challenges for ibuprofen in the presence of ethanol, especially at ethanol concentrations of 30% or more, prompted exploratory activities to identify an alternative, foam formulation.

A comparator for foam formulation screening was the foamable diclofenac formulation. The ingredients of the foamable diclofenac formulation are provided in Table 22. See also Example 1.

TABLE 22

Composition of DMSO Base Foam Formulation
Component

Diclofenac sodium
Ethanol
Propylene glycol
Dimethylsulfoxide (DMSO)
Glycerin
Water
Brij 30
Brij 78
Cholesterol
Sodium laureth sulfate (SLES)

Example 14

Effect of Sodium Carbonate on the Permeability of Ibuprofen

Sodium carbonate was added to the formulation to control the pH of the formulation (Table 23). Initially, 0.5% of sodium carbonate was added to the formulation, as this was estimated to raise the pH of the formulation to 6.0. All formulations contained 0.1% cholesterol as a foam stabilizing agent and the concentration of Brij 30 was maintained at 1.3%. The effect of addition of sodium carbonate to the formulation was studied in combination with each of the anionic surfactants SLS and SLES. The procedures set forth in Example 13 were used for the evaluation.

TABLE 23

Effect of Sodium Carbonate on the Permeability of Ibuprofen from Foam Formulations)

| Component (wt %) | Ibugel | Ibu 100802-01 | Ibu 100802-02 | Ibu 100802-03 | Ibu 100802-04 |
|---|---|---|---|---|---|
| Ibuprofen | 5.0 | 5.0 | 5.0 | 5.0 | 5.0 |
| DMSO | | 28.7 | 28.7 | 28.7 | 28.7 |
| Water | | 43.7 | 44.2 | 43.7 | 44.2 |
| Ethanol | | 7.4 | 7.4 | 7.4 | 7.4 |
| Propylene Glycol | | 7.1 | 7.1 | 7.1 | 7.1 |
| Glycerin | | 4.9 | 4.9 | 4.9 | 4.9 |
| Brij 30 | | 1.3 | 1.3 | 1.3 | 1.3 |
| Cholesterol | | 0.1 | 0.1 | 0.1 | 0.1 |
| SLS | | 1.3 | 1.3 | 0 | 0 |
| Sodium carbonate | | 0.5 | 0 | 0.5 | 0 |
| SLES | | 0 | 0 | 1.3 | 1.3 |
| Cum amt transported at 24 h (µg/cm2) (Mean) | 45.57 | 112.83 | 104.09 | 104.71 | 110.49 |
| SEM | 11.83 | 12.41 | 10.14 | 2.42 | 17.22 |
| ER | 1.0 | 2.48 | 2.28 | 2.30 | 2.42 |

Figure 56:
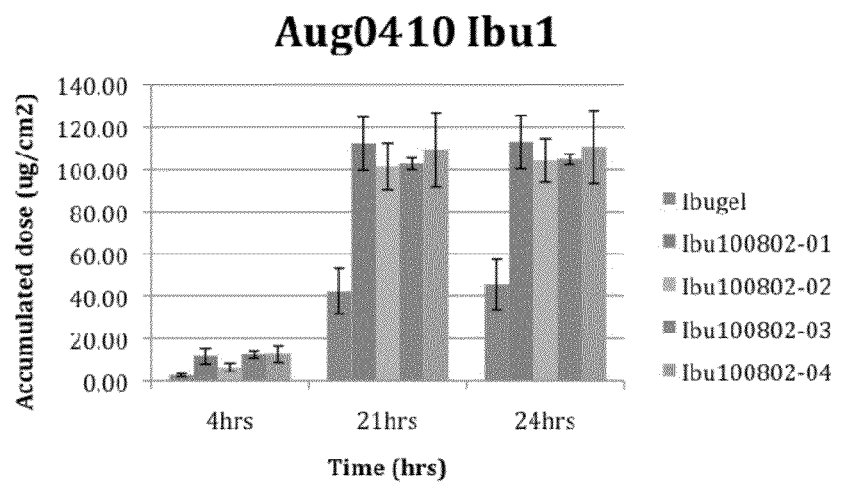
FIG. 56 illustrates the effect of sodium carbonate on the delivery of ibuprofen from foam formulations.

The results are shown in FIG. 56. A two-fold increase in ibuprofen delivery at 24 h as compared to Ibugel was achieved for all the formulations tested. No trends were observed for permeability of ibuprofen in presence of sodium carbonate (Ibu 100802-01 vs. Ibu 100802-02 and Ibu 100802-03 vs. Ibu 100802-04)). Based on the cumulative amount transported at 24 h after dose application, the delivery of ibuprofen from formulations containing either SLS or SLES as the anionic surfactant was comparable (100802-01 vs. Ibu 100802-03). The type of anionic surfactant used appeared to have no impact on the delivery of ibuprofen.

Example 15

Effect of Thickening Agent and Reduction of Total Surfactant Concentration on the Permeability of Ibuprofen Cholesterol was eliminated from the formulation and the following changes were evaluated: addition of 2% HPC(HPC HY 121) as a thickening agent; influence of the type of anionic surfactant (SLS vs. SLES); and the effect of reducing the total surfactant concentration from 2.6% to 1.3% (Table 24). The procedures set forth in Example 13 were used for the evaluation.

TABLE 24

Effect of Thickening Agent and Reduction of Total Surfactant on the Permeability of Ibuprofen

| Component (wt %) | Ibugel | Ibu 100810-01 | Ibu 100810-02 | Ibu 100810-03 | Ibu 100810-05 | Ibu 100810-06 |
|---|---|---|---|---|---|---|
| Ibuprofen | 5.0 | 5.0 | 5.0 | 5.0 | 5.0 | 5.0 |
| DMSO | | 28.7 | 28.7 | 28.7 | 28.7 | 28.7 |
| Water | | 41.8 | 42.3 | 41.8 | 45.1 | 45.1 |
| Ethanol | | 7.4 | 7.4 | 7.4 | 7.4 | 7.4 |
| Propylene Glycol | | 7.1 | 7.1 | 7.1 | 7.1 | 7.1 |
| Glycerin | | 4.9 | 4.9 | 4.9 | 4.9 | 4.9 |
| Brij 30 | | 1.3 | 1.3 | 1.3 | 0 | 1.3 |
| Cholesterol | | 0 | 0 | 0 | 0 | 0 |
| SLS | | 1.3 | 1.3 | 0 | 1.3 | 0 |
| Sodium carbonate | | 0.5 | 0 | 0.5 | 0.5 | 0.5 |
| SLES | | 0 | 0 | 1.3 | 0 | 0 |

TABLE 24-continued

Effect of Thickening Agent and Reduction of Total Surfactant on the Permeability of Ibuprofen

| Component (wt %) | Ibugel | Ibu 100810-01 | Ibu 100810-02 | Ibu 100810-03 | Ibu 100810-05 | Ibu 100810-06 |
|---|---|---|---|---|---|---|
| HPC HY 121 | | 2.0 | 2.0 | 2.0 | 0 | 0 |
| Cum amt transported at 24 h (µg/cm2) | 21.62 | 100.42 | 117.31 | 101.50 | 118.80 | 154.87 |
| SEM | 2.84 | 7.32 | 4.84 | 6.95 | 8.31 | 13.22 |
| ER | 1.00 | 4.65 | 5.43 | 4.70 | 5.5 | 7.16 |

Figure 57:
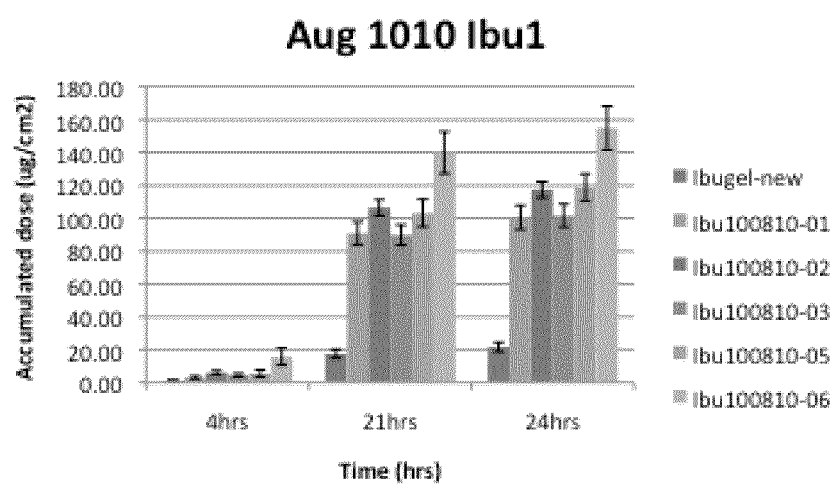
FIG. 57 illustrates the effect of sodium carbonate in presence of thickening agent, and reduction of total surfactant on the delivery of ibuprofen.

The results are shown in FIG. 57. A four- to seven fold increase in ibuprofen delivery as compared to Ibugel was achieved with all the formulations. Addition of 2% HPC (HY 121) as a thickening agent to formulations containing sodium carbonate (100810-01 vs. 100810-02) did not seem to impact the permeability of ibuprofen. The type of anionic surfactant used (SLS or SLES) did not seem to impact the permeability of ibuprofen from formulations containing a thickening agent (100801-01 vs. 100801-03). Reducing the total surfactant concentration from 2.6% to 1.3% by eliminating non-ionic surfactant Brij 30 did not seem to affect the permeability of ibuprofen from the formulations (100810-01 vs. 100810-05). Reducing the total surfactant concentration from 2.6% to 1.3% by eliminating the anionic surfactant SLS may have improved permeation of ibuprofen from the formulations (100810-01 vs. 100810-06).

Example 16

Effect of Surfactants in the Formulation on the Permeability of Ibuprofen

I: Brij 78

Experiments were conducted to understand the effects of surfactant type, total surfactant concentration and ratio of surfactants on the permeability of ibuprofen from the test formulations. The procedures set forth in Example 13 were used for the evaluation.

An additional non-ionic surfactant, 1% Brij 78, was added to all the formulations (Table 25). For formulations 1000802-1 to 1000802-4, 1.3% Brij 30 was also added to maintain the non-ionic surfactant concentration 2.3%, while either SLS or SLES was used at 2% concentration to maintain the total surfactant (non-ionic+anionic surfactant) concentration at 4.3%. These formulations also contained 0.1% cholesterol.

The effect of removal of glycerin on the permeability of ibuprofen was investigated with formulations 4-F1, 4-F2, and 4-F3. In these formulations, cholesterol was removed, 2% SLS and 1% SLES were added while the Brij 78 concentration was maintained at 1% and Brij 30 level was reduced to 0.1%. In addition, the ethanol level was increased from 7.4% to 11.2%.

TABLE 25

Effect of Addition of Brij 78, Increased Ethanol, and Removal of Glycerine on Permeability of Ibuprofen

| Component (wt %) | Ibugel | Ibu 100802-1 | Ibu 100802-2 | Ibu 100802-3 | Ibu 100802-4 | Ibu 100802-4-F1 | Ibu 100802-4-F2 | Ibu 100802-4-F3 |
|---|---|---|---|---|---|---|---|---|
| Ibuprofen | 5.0 | 5.0 | 5.0 | 5.0 | 5.0 | 5.0 | 5.0 | 5.0 |
| DMSO | | 28.7 | 28.7 | 28.7 | 28.7 | 29.7 | 29.7 | 29.7 |
| Water | | 43.7 | 44.2 | 43.7 | 44.2 | 37.3 | 36.8 | 41.9 |
| Ethanol | | 7.4 | 7.4 | 7.4 | 7.4 | 11.2 | 11.2 | 11.2 |
| Propylene Glycol | | 7.1 | 7.1 | 7.1 | 7.1 | 7.3 | 7.3 | 7.3 |
| Glycerin | | 4.9 | 4.9 | 4.9 | 4.9 | 5.0 | 5.1 | 0 |
| Brij 30 | | 1.3 | 1.33 | 1.3 | 1.33 | 0.1 | 0.1 | 0.1 |
| Cholesterol | | 0.1 | 0.1 | 0.1 | 0.1 | 0 | 0 | 0 |
| SLS | | 2.0 | 2.0 | 0 | 0 | 2.0 | 2.0 | 2.0 |
| Sodium carbonate | | 0.5 | 0 | 0.5 | 0 | 0 | 0.5 | 0.5 |
| SLES | | 0 | 0 | 2 | 2 | 1 | 1 | 1 |
| Brij 78 | | 1 | 1 | 1 | 1 | 1 | 1 | 1 |
| Cum amt transported at 24 h (µg/cm2) | 23.54 | 66.40 | 80.62 | 74.66 | 77.10 | 64.09 | 70.04 | 62.08 |
| SEM | 4.51 | 13.54 | 13.49 | 9.94 | 14.19 | 14.49 | 9.41 | 6.74 |
| ER | 1.00 | 2.82 | 3.43 | 3.17 | 3.28 | 2.72 | 2.98 | 2.64 |

Figure 58:
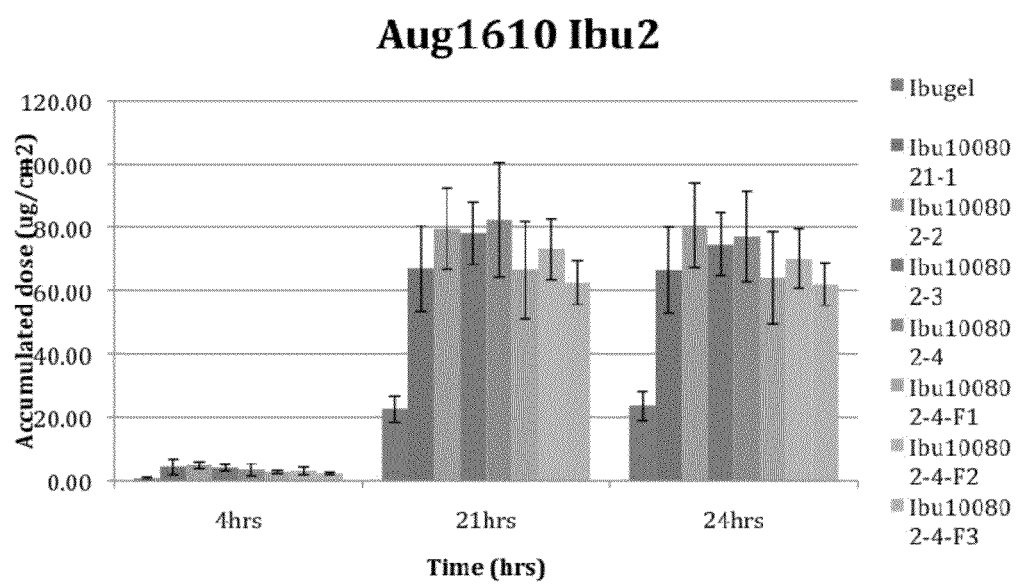
FIG. 58 illustrates the effect of addition of Brij 78, increased ethanol, and removal of glycerin on delivery of ibuprofen.

The results are shown in FIG. 58. A two- to three fold increase in ibuprofen delivery compared to Ibugel was achieved for all the formulations. The type of anionic surfactant used (SLS or SLES) did not seems to have a measurable impact on permeability (100802-1 vs. 100802-4). The delivery of ibuprofen from the formulations containing either of the anionic surfactants did not seem to be impacted by the presence or absence of sodium carbonate (100802-1 vs. 100802-2 and 100802-3 vs. 10802-4). For the formulations containing 11.2% ethanol, the presence or absence of sodium carbonate in the formulation seemed to have no impact on permeability (100802-4-F1 vs. 100802-4-F2). For the formulations containing 11.2% ethanol, the removal of glycerin seemed to have no impact on the permeability of ibuprofen (100802-4-F2 vs. 100802-4-F3).

Example 17

Effect of Surfactants in the Formulation on the Permeability of Ibuprofen

II: Anionic Surfactants

Experiments were conducted to understand the effects of surfactant type, total surfactant concentration and ratio of surfactants on the permeability of ibuprofen from the test formulations. The procedures set forth in Example 13 were used for the evaluation.

The non-ionic surfactants were maintained constant at 2%, while the total concentration of the anionic surfactant combination was varied from 1 to 2%, both in presence and absence of cholesterol (Table 26). The ratio of the anionic surfactants, SLS to SLES was also varied within the formulations.

TABLE 26

Effect of Anionic Surfactant Ratio and Total Surfactant Concentration

| Component (wt %) | Ibugel | Ibu 100816-19 | Ibu 100816-20 | Ibu 100816-21 | Ibu 100816-22 | Ibu 100816-23 | Ibu 100816-24 | Ibu 100816-25 | Ibu 100816-26 |
|---|---|---|---|---|---|---|---|---|---|
| Ibuprofen | 5.0 | 5.0 | 5.0 | 5.0 | 5.0 | 5.0 | 5.0 | 5.0 | 5.0 |
| DMSO | | 28.1 | 28.5 | 28.3 | 28.3 | 28.1 | 28.4 | 28.4 | 28.4 |
| Water | | 43.4 | 43.6 | 43.5 | 43.5 | 43.4 | 43.5 | 43.5 | 43.5 |
| Ethanol | | 7.3 | 7.4 | 7.3 | 7.3 | 7.3 | 7.3 | 7.3 | 7.3 |
| Propylene Glycol | | 6.9 | 7.0 | 7.0 | 7.0 | 6.9 | 7.0 | 7.0 | 7.0 |
| Glycerin | | 4.7 | 4.8 | 4.8 | 4.8 | 4.8 | 4.8 | 4.8 | 4.8 |
| Brij 30 | | 1.0 | 1.0 | 1.0 | 1.0 | 1.0 | 1.0 | 1.0 | 1.0 |
| Cholesterol | | 0.1 | 0.1 | 0.1 | 0.1 | 0 | 0 | 0 | 0.1 |
| SLS | | 1 | 0.5 | 0.5 | 1 | 1 | 0.5 | 1 | 1 |
| Sodium carbonate | | 0.5 | 0.5 | 0.5 | 0.5 | 0.5 | 0.5 | 0.5 | 0.5 |
| SLES | | 1.0 | 0.5 | 1.0 | 0.5 | 1.0 | 1.0 | 0.5 | 0 |
| Brij 78 | | 1.0 | 1.0 | 1.0 | 1.0 | 1.0 | 1.0 | 1.0 | 1.0 |
| Cum amt transported at 24 h (µg/cm2) | 27.54 | 56.50 | 58.72 | 68.83 | 52.66 | 56.29 | 63.55 | 53.86 | 75.55 |
| SEM | 18.52 | 18.75 | 16.09 | 20.82 | 19.87 | 16.32 | 12.21 | 12.42 | 11.36 |
| ER | 1.00 | 2.05 | 2.13 | 2.5 | 1.9 | 2.04 | 2.31 | 1.96 | 2.74 |

Figure 59:
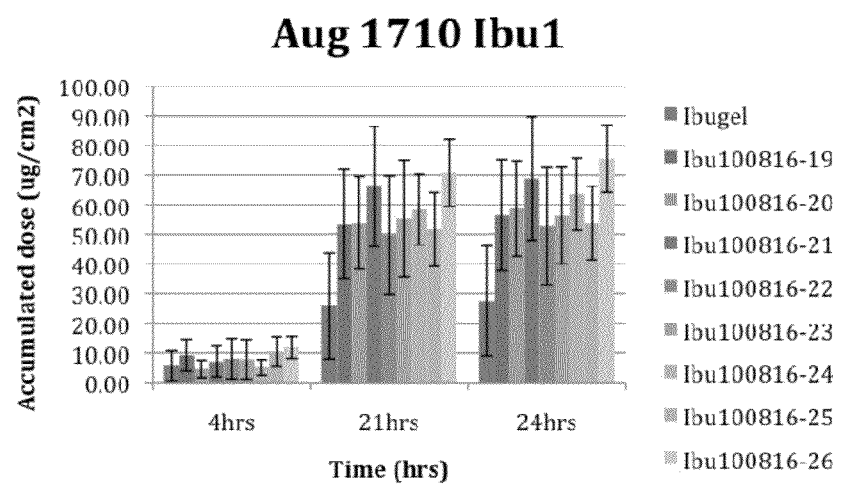
FIG. 59 illustrates the effect of anionic surfactant ratio and total surfactant concentration on delivery of ibuprofen.

The results are shown in FIG. 59. A two-fold increase in ibuprofen delivery as compared to Ibugel was observed for all formulations tested. In the presence of 0.1% cholesterol, varying the total anionic surfactant concentration to 1%, 1.5%, or 2% seemed to have a negligible effect on the permeability of ibuprofen, irrespective of the ratio of SLES to SLS (Ibu 100816-19 to Ibu 100816-22). In the absence of cholesterol, varying the total anionic surfactant concentration to 1%, 1.5%, or 2% seemed to have a negligible effect on the permeability of ibuprofen, irrespective of the ratio of SLES to SLS (Ibu 100816-23 to Ibu 100816-25). A slight increase in permeability was observed when SLES was removed from the anionic surfactant combination (Ibu 100816-26).

Example 18

Effect of Surfactants in the Formulation on the Permeability of Ibuprofen

III: Non-ionic Surfactants

Experiments were conducted to understand the effects of surfactant type, total surfactant concentration and ratio of surfactants on the permeability of ibuprofen from the test formulations. The procedures set forth in Example 13 were used for the evaluation.

A single anionic surfactant SLS was used and the concentration of SLS was maintained constant at either 1% or 1.3%, while the effect of changing non-ionic surfactant concentration was studied (Table 27). The objective of the experiment was to explore the possibility of reducing the total surfactant levels in the formulation.

TABLE 27

Effect of Non-ionic Surfactant Concentration on Permeability of Ibuprofen

| Component (wt %) | Ibugel | Ibu 100816-10 | Ibu 100816-11 | Ibu 100816-12 | Ibu 100816-14 | Ibu 100816-15 | Ibu 100816-16 | Ibu 100816-17 |
|---|---|---|---|---|---|---|---|---|
| Ibuprofen | 5.0 | 5.0 | 5.0 | 5.0 | 5.0 | 5.0 | 5.0 | 5.0 |
| DMSO | | 28.7 | 29.4 | 28.8 | 28.5 | 29.0 | 29.0 | 28.6 |
| Water | | 43.7 | 43.9 | 43.7 | 43.6 | 43.8 | 43.8 | 43.6 |
| Ethanol | | 7.4 | 7.6 | 7.5 | 7.4 | 7.5 | 7.5 | 7.4 |
| Propylene Glycol | | 7.1 | 7.2 | 7.1 | 7.0 | 7.1 | 7.1 | 7.0 |
| Glycerin | | 4.9 | 5.0 | 4.9 | 4.8 | 4.9 | 4.9 | 4.8 |
| Brij 30 | | 1.3 | 0 | 1.3 | 1 | 1 | 0 | 1 |
| Cholesterol | | 0.1 | 0.1 | 0 | 0.1 | 0.1 | 0.1 | 0 |
| SLS | | 1.3 | 1.3 | 1.3 | 1 | 1 | 1 | 1 |
| Sodium carbonate | | 0.5 | 0.5 | 0.5 | 0.5 | 0.5 | 0.5 | 0.5 |
| Brij 78 | | 0 | 0 | 0 | 1 | 0 | 1 | 1 |
| Cum amt transported at 24 h ($\mu g/cm^2$) | 14.42 | 86.97 | 97.92 | 107.50 | 124.43 | 120.83 | 88.85 | 111.87 |
| SEM | 3.44 | 21.52 | 20.22 | 21.48 | 17.01 | 18.83 | 23.39 | 21.93 |
| ER | 1.00 | 6.03 | 6.79 | 7.46 | 8.63 | 8.38 | 6.16 | 7.76 |

Figure 60:
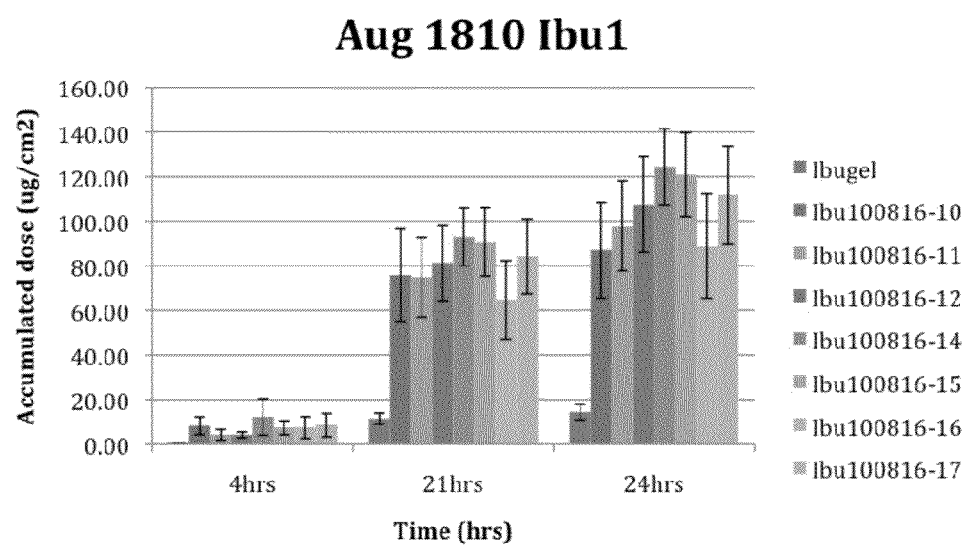
FIG. 60 illustrates the effect of non-ionic surfactant concentration on the delivery of ibuprofen.

The results are shown in FIG. 60. A six to eight fold increase in delivery of ibuprofen as compared to Ibugel was observed for all formulations. Lowering the total concentration of surfactants in the formulation to 1.3% or 2% by decreasing the concentration of non ionic surfactants did not seem to impact the permeability of ibuprofen.

Example 19

Effect of Surfactants in the Formulation on the Permeability of Ibuprofen

IV: Reduced Surfactant Concentration

Experiments were conducted to understand the effects of surfactant type, total surfactant concentration and ratio of surfactants on the permeability of ibuprofen from the test formulations. The procedures set forth in Example 13 were used for the evaluation.

The results of the experiments Examples 16, 17, and 18 indicated that the permeability of ibuprofen from the DMSO based formulation chassis may be independent of the surfactant concentration in the range of 1.3% to 4.3%. The results from the experiments conducted in Example 18 demonstrated that a reduction in the total concentration of surfactants appeared not to impact the permeability of ibuprofen. The following set of experiments were conducted using formulations without cholesterol to confirm that the total concentration of surfactants in the formulation could be reduced without significant impact on the permeability of ibuprofen (Table 28).

TABLE 28

Effect of Reduced Surfactant Concentration and Surfactant Type

| Component (wt %) | Ibugel | Ibu 100810-1 | Ibu 100810-2 | Ibu 100810-3 | Ibu 100810-5 | Ibu 100810-7 | Ibu 100810-8 |
|---|---|---|---|---|---|---|---|
| Ibuprofen | 5.0 | 5.0 | 5.0 | 5.0 | 5.0 | 5.0 | 5.0 |
| DMSO | | 28.7 | 28.7 | 28.7 | 45.5 | 28.7 | 28.7 |
| Water | | 43.8 | 44.3 | 43.8 | 18.8 | 45.1 | 45.1 |
| Ethanol | | 7.4 | 7.4 | 7.4 | 11.8 | 7.4 | 7.4 |
| Propylene Glycol | | 7.1 | 7.1 | 7.1 | 11.2 | 7.1 | 7.1 |
| Glycerin | | 4.9 | 4.9 | 4.9 | 7.7 | 4.9 | 4.9 |
| Brij 30 | | 1.3 | 1.33 | 1.3 | 0 | 0 | 1.3 |
| Cholesterol | | 0 | 0 | 0 | 0 | 0 | 0 |
| SLS | | 1.3 | 1.27 | 0 | 0 | 1.3 | 0 |
| Sodium carbonate | | 0.5 | 0 | 0.5 | 0 | 0.5 | 0.5 |
| SLES | | 0 | 0 | 1.3 | 0 | 0 | 0 |
| Cum amt transported at 24 h (µg/cm2) | 34.01 | 65.68 | 86.04 | 89.97 | 79.77 | 95.49 | 86.02 |
| SEM | 10.37 | 14.40 | 13.17 | 11.87 | 11.94 | 14.74 | 16.67 |
| ER | 1.00 | 1.93 | 2.53 | 2.65 | 2.35 | 2.81 | 2.53 |

Figure 61:
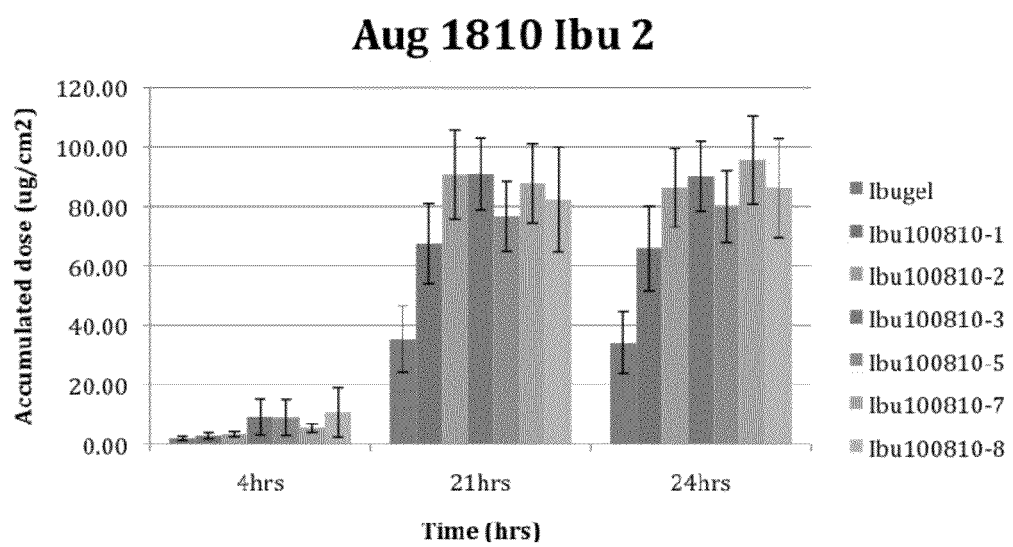
FIG. 61 illustrates the effect of reduced surfactant concentration and surfactant type on the delivery of ibuprofen.

The results are shown in FIG. 61. A two fold increase in the delivery of ibuprofen as compared to Ibugel was observed (except for formulation 100810-1). The addition of sodium carbonate appeared to decrease the permeability of ibuprofen when a combination of Brij 30 and SLS was used (formulation 100810-1). The reason for this decrease was unclear, particularly as previous experiments have indicated that the presence of sodium carbonate did not seem to negatively impact the permeability of ibuprofen.

The type of anionic surfactant used in the formulation (SLS or SLES) seemed to have no impact on the permeability of ibuprofen. Acceptable levels of ibuprofen transport could be obtained from formulations that contain only 1.3% of a single surfactant (100810-7 vs. 100810-8), confirming findings that the surfactant concentration in the formulations can be reduced without any impact to the permeability of ibuprofen. Acceptable levels of ibuprofen permeation could be obtained with formulations that do not contain surfactants or cholesterol, when the formulation contained DMSO at levels greater than 28% (Ibu 100810-5).

Example 20

Effect of Surfactants in the Formulation on the Permeability of Ibuprofen

V: Non-ionic Surfactants

Experiments were conducted to understand the effects of surfactant type, total surfactant concentration and ratio of surfactants on the permeability of ibuprofen from the test formulations. The procedures set forth in Example 13 were used for the evaluation.

Another round of formulations was conducted to confirm the need for non-ionic surfactants in the formulation and to confirm the viability of reduced surfactant concentration in the formulation (Table 29).

Figure 62:
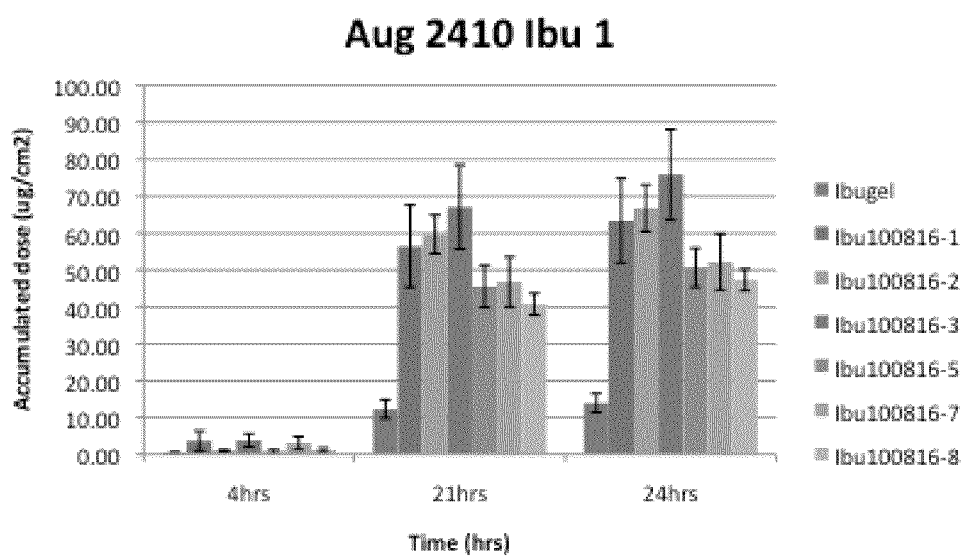
FIG. 62 illustrates the effect of non-ionic surfactants on delivery of ibuprofen.

The results are shown in FIG. 62. A three to five fold increase in ibuprofen delivery as compared to Ibugel was observed from the formulations. Reduction of total surfactant concentration from 2.6% to 1.3% by removal of Brij 30 proved unlikely to impact the permeability of ibuprofen (100816-1 vs 100816-2). Removal of cholesterol from the formulation containing 2.6% total surfactant proved unlikely to impact the permeability of ibuprofen (100816-1 vs 100816-3). Increasing the surfactant concentration to 3%, by the addition of Brij 78 proved likely to negatively impact the permeability of ibuprofen (100816-1 vs. 100816-5 and 100816-8). The results confirmed findings that a combination of anionic surfactant with non-ionic surfactant appeared likely to provide a suitable formulation from an ibuprofen delivery perspective.

Example 21

Effect of Surfactants in the Formulation on the Permeability of Ibuprofen

VI: Brij 78

Experiments were conducted to understand the effects of surfactant type, total surfactant concentration and ratio of surfactants on the permeability of ibuprofen from the test formulations. The procedures set forth in Example 13 were used for the evaluation.

The effect of varying concentrations of non-ionic surfactant Brij 78 was studied in combination with either one of the anionic surfactant SLS or SLES (Table 30). Brij 30 concentration was maintained at 1% for all the formulations, and the cholesterol level was varied from 0.1 to 0.2%.

TABLE 29

Effect of Non-Ionic Surfactants on Delivery of Ibuprofen

| Component (wt %) | Ibugel | Ibu 100816-1 | Ibu 100816-2 | Ibu 100816-3 | Ibu 100816-5 | Ibu 100816-7 | Ibu 100816-8 |
| --- | --- | --- | --- | --- | --- | --- | --- |
| Ibuprofen | 5.0 | 5.0 | 5.0 | 5.0 | 5.0 | 5.0 | 5.0 |
| DMSO | | 28.7 | 29.4 | 28.8 | 28.5 | 29.0 | 28.6 |
| Water | | 43.7 | 43.9 | 43.7 | 43.6 | 43.8 | 43.6 |
| Ethanol | | 7.4 | 7.6 | 7.5 | 7.4 | 7.5 | 7.4 |
| Propylene Glycol | | 7.1 | 7.2 | 7.1 | 7.0 | 7.1 | 7.0 |
| Glycerin | | 4.9 | 5.0 | 4.9 | 4.8 | 4.9 | 4.8 |
| Brij 30 | | 1.3 | 0 | 1.3 | 1.0 | 0 | 1.0 |
| Cholesterol | | 0.1 | 0.1 | 0 | 0.1 | 0.1 | 0 |
| SLES | | 1.3 | 1.3 | 1.3 | 1.0 | 1.0 | 1.0 |
| Sodium carbonate | | 0.5 | 0.5 | 0.5 | 0.5 | 0.5 | 0.5 |
| Brij 78 | | 0 | 0 | 0 | 1.0 | 1.0 | 1.0 |
| Cum amt transported at 24 h (µg/cm2) | 13.95 | 63.35 | 66.78 | 75.83 | 50.67 | 52.20 | 47.29 |
| SEM | 2.58 | 11.46 | 6.35 | 12.29 | 5.29 | 7.62 | 2.90 |
| ER | 1.00 | 4.54 | 4.79 | 5.44 | 3.63 | 3.74 | 3.39 |

TABLE 30

Effect of Brij 78 Levels on the Permeability of Ibuprofen

| Component wt % | Ibugel | Ibu 100826-01 | Ibu 100826-02 | Ibu 100826-03 | Ibu 100826-04 | Ibu 100826-01 (2) |
|---|---|---|---|---|---|---|
| Ibuprofen | 5.0 | 5.0 | 5.0 | 5.0 | 5.0 | 5.0 |
| DMSO | | 28.7 | 28.7 | 28.7 | 28.7 | 28.7 |
| Water | | 43.9 | 42.9 | 43.9 | 42.9 | 44.3 |
| Ethanol | | 7.4 | 7.4 | 7.4 | 7.4 | 7.4 |
| Propylene Glycol | | 7.1 | 7.1 | 7.1 | 7.1 | 7.1 |
| Glycerin | | 4.9 | 4.9 | 4.9 | 4.9 | 4.9 |
| Brij 30 | | 1.0 | 1.0 | 1.0 | 1.0 | 1.0 |
| Cholesterol | | 0.2 | 0.2 | 0.2 | 0.1 | 0.1 |
| SLS | | 0 | 0 | 0.3 | 0.3 | 0 |
| Sodium carbonate | | 0.5 | 0.5 | 0.5 | 0.5 | 0.5 |
| SLES | | 0.3 | 0.3 | 0 | 0 | 0 |
| Brij 78 | | 1.0 | 2.0 | 1.0 | 2.0 | 1.0 |
| Cum amt transported at 24 h (µg/cm2) | 8.24 | 56.14 | 42.86 | 67.43 | 63.81 | 76.08 |
| SEM | 1.34 | 4.27 | 4.30 | 4.64 | 5.30 | 23.7 |
| ER | 1.00 | 6.81 | 5.20 | 8.18 | 7.74 | 9.23 |

Figure 63:
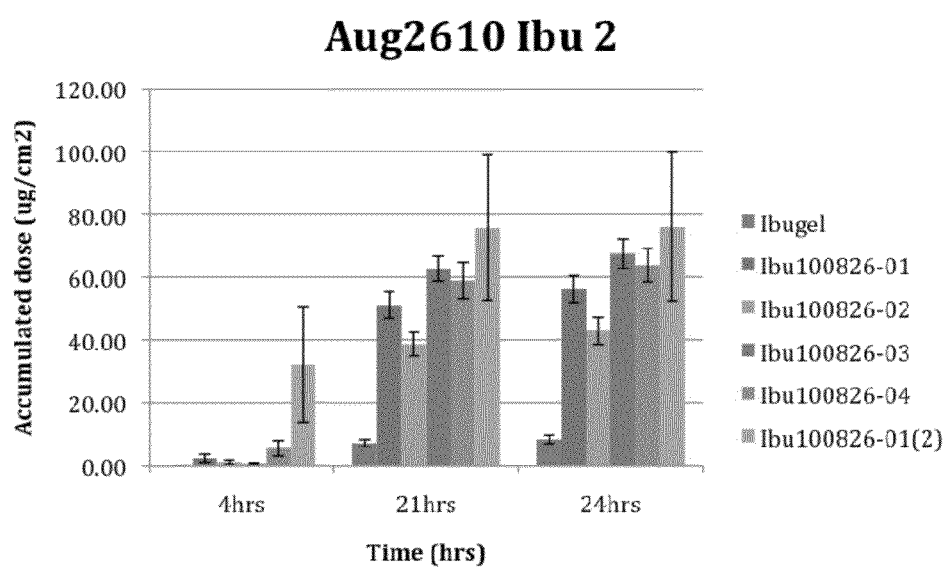
FIG. 63 illustrates the effect of Brij 78 levels on the delivery of ibuprofen.

The results are shown in FIG. 63. A five- to nine-fold enhancement in the delivery of ibuprofen as compared to Ibugel was observed for the formulations tested. For formulations containing 0.2% cholesterol and SLES, increasing the Brij 78 concentration to 2% apparently decreased the permeability of ibuprofen (100826-02). For formulations containing 0.2% cholesterol and SLS, increasing the Brij 78 concentration to 2% seemed to have no impact on the permeability of ibuprofen (100826-03 and 100826-04). There appeared to be a trend towards higher permeability of ibuprofen from formulations that contain a surfactant combination of SLS and Brij 78, as compared to formulations that contain a surfactant combination of Brij 78 and SLES. (100826-01 vs 100826-03 and 100826-02 vs 100826-04). The results confirmed earlier findings that removal of anionic surfactants appeared unlikely to impact the permeability of ibuprofen from DMSO based formulations.

Example 22

Effect of Cholesterol Levels on Permeability of Ibuprofen from DMSO-Based Formulations Based on the results of the previous experiments that demonstrate that permeability of ibuprofen from DMSO based formulations showed low sensitivity to surfactant concentrations in the formulations, experiments to evaluate the effect of varying cholesterol levels from 0 to 0.4% was determined using the formulations with reduced surfactant levels (Table 31). The procedures set forth in Example 13 were used for the evaluation.

TABLE 31

Effect of Cholesterol Levels on Permeability of Ibuprofen

| Component (wt %) | Ibugel | Ibu 100823-01 | Ibu 100823-02 | Ibu 100823-04 | Ibu 100823-05 | Ibu 100823-06 | Ibu 100823-07 | Ibu 100823-08 | Ibu 100823-09 | Ibu 100823-10 | Ibu 100823-11 |
|---|---|---|---|---|---|---|---|---|---|---|---|
| Ibuprofen | 5.0 | 5.0 | 5.0 | 5.0 | 5.0 | 5.0 | 5.0 | 5.0 | 5.0 | 5.0 | 5.0 |
| DMSO | | 28.7 | 28.7 | 28.7 | 28.7 | 28.7 | 28.7 | 28.7 | 28.7 | 28.7 | 28.7 |
| Water | | 32.4 | 32.5 | 32.4 | 32.35 | 32.3 | 32.2 | 32.25 | 32.1 | 31.9 | 31.4 |
| Ethanol | | 7.4 | 7.4 | 12.3 | 7.4 | 7.4 | 7.4 | 7.4 | 7.4 | 7.4 | 7.4 |
| Propylene Glycol | | 7.1 | 7.1 | 7.1 | 7.1 | 7.1 | 7.1 | 7.1 | 7.1 | 7.1 | 7.1 |
| Glycerin | | 4.9 | 4.9 | 0 | 4.9 | 4.9 | 4.9 | 4.9 | 4.9 | 4.9 | 4.9 |
| Brij 30 | | 1.0 | 1.0 | 1.0 | 1.0 | 1.0 | 1.0 | 1.0 | 1.0 | 1.0 | 1.0 |
| Cholesterol (Note that dissolution of cholesterol in the formulation at concentrations >0.1% is challenging) | | 0.1 | 0 | 0.1 | 0.15 | 0.2 | 0.3 | 0.4 | 0.1 | 0.1 | 0.1 |
| SLS | | 0 | 0 | 0 | 0 | 0 | 0 | 0 | 0 | 0 | 0 |
| Sodium carbonate | | 0.5 | 0.5 | 0.5 | 0.5 | 0.5 | 0.5 | 0.5 | 0.5 | 0.5 | 0 |

TABLE 31-continued

Effect of Cholesterol Levels on Permeability of Ibuprofen

| Component (wt %) | Ibugel | Ibu 100823-01 | Ibu 100823-02 | Ibu 100823-04 | Ibu 100823-05 | Ibu 100823-06 | Ibu 100823-07 | Ibu 100823-08 | Ibu 100823-09 | Ibu 100823-10 | Ibu 100823-11 |
|---|---|---|---|---|---|---|---|---|---|---|---|
| SLES | | 0 | 0 | 0 | 0 | 0 | 0 | 0.15 | 0.3 | 0.5 | 0.5 |
| Brij 78 | | 1.0 | 1.0 | 1.0 | 1.0 | 1.0 | 1.0 | 1.0 | 1.0 | 1.0 | 1.0 |
| Cum amt transported at 24 h (µg/cm2) | 4.65 | 61.0 | 73.93 | 54.47 | 52.56 | 87.36 | 66.44 | 60.84 | 76.44 | 69.77 | 63.25 |
| SEM | 1.78 | 4.42 | 9.40 | 10.05 | 3.31 | 8.58 | 7.37 | 7.94 | 6.09 | 9.71 | 8.34 |
| ER | | | | | | Not calculated | | | | | |

Figure 64:
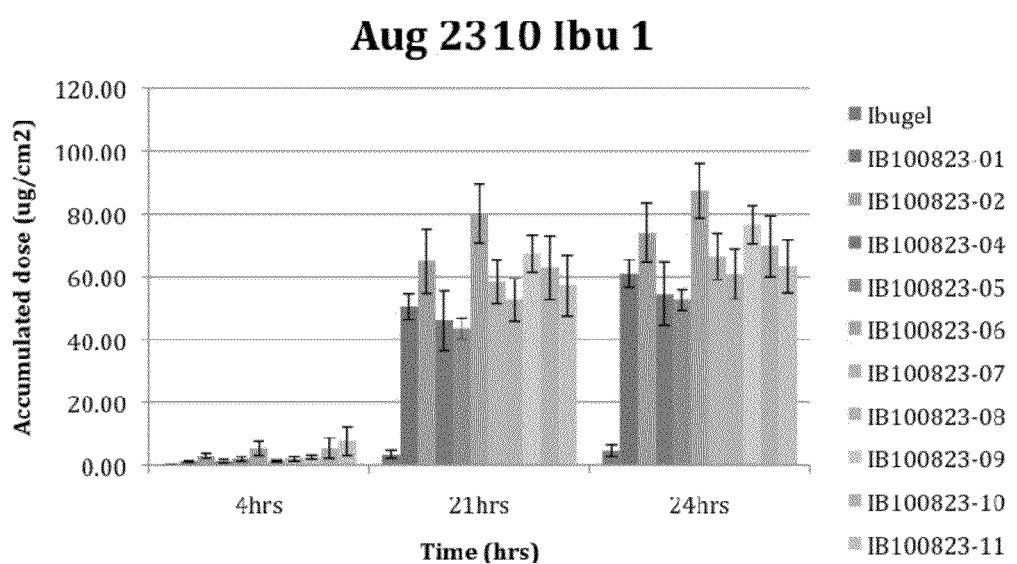
FIG. 64 illustrates the effect of cholesterol levels on the delivery of ibuprofen from DMSO based formulations.

The results are shown in FIG. 64. Based on the cumulative amount of ibuprofen transported at 24 h, it seemed likely that cholesterol levels have no impact on permeability of ibuprofen. Control Ibugel formulation exhibited considerably lower than normal values for delivery of ibuprofen (approximately 10% of normal values) and appears to be outside the range of normally observed values. Therefore, ER was not calculated for this experiment.

Example 23

Evaluation of Water-Based Formulation (No Additional Solvents)

The permeability of ibuprofen from a water based formulation containing no solvents was compared to a DMSO based formulation (Table 32). The procedures set forth in Example 13 were used for the evaluation.

TABLE 32

Effect of Water Based Formulation on Permeability of Ibuprofen)

| Component wt % | Ibugel | Ibu 100823-X | Ibu 100802-4 |
|---|---|---|---|
| Ibuprofen | 5.0 | 5.0 | 5.0 |
| DMSO | | 0 | 28.74 |
| Water | | 90.65 | 44.18 |
| Ethanol | | 0 | 7.45 |
| Propylene Glycol | | 0 | 7.07 |
| Glycerin | | 0 | 4.86 |
| Brij 30 | | 1 | 1.33 |
| Cholesterol | | 0.1 | 0.1 |
| SLES | | 0 | 1.27 |
| Sodium carbonate | | 1.25 | 0 |
| Brij 78 | | 2 | 0 |
| Cum amt transported at 24 h (µg/cm2) | 13.95 | 20.01 | 39.59 |
| SEM | 2.58 | 9.96 | 7.15 |
| ER | 1.00 | 1.43 | 2.84 |

Figure 65:
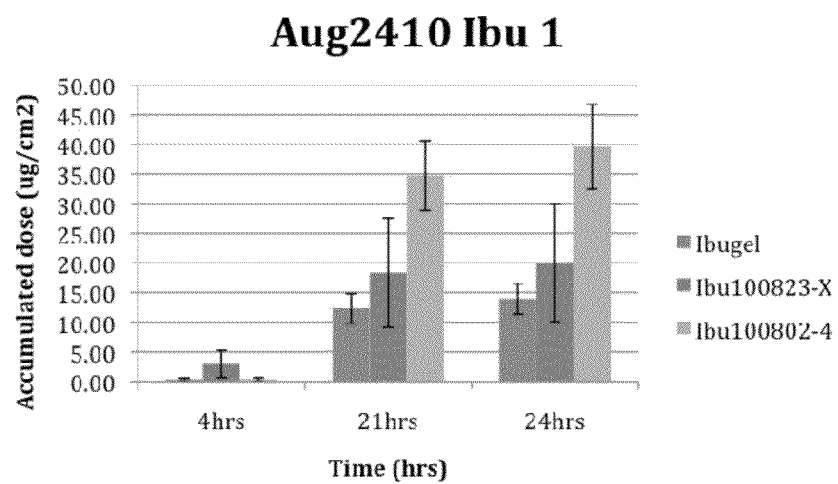
FIG. 65 illustrates the effect of water-based formulations on the delivery of ibuprofen.

The results are shown in FIG. 65. The DMSO-free formulation failed to provide a two-fold delivery enhancement over that of Ibugel (100823-X). Based on the differences in ER, it appeared that a DMSO-free, water-based formulation seemed unlikely to meet the permeability performance characteristics needed for the product. The DMSO based formulation (Ibu 100802-4) met the target permeability characteristics required for the ibuprofen foam formulation.

Example 24

Evaluation of a Water-Based Formulation Containing Thickening Agents and Poloxamer 407

Additional work was conducted with water-based formulations to determine if the addition of hydropropyl cellulose (HPC HY 121 and HPC HY 117) would improve the delivery characteristics from this formulation (Table 33). The experiment also evaluated whether the combination of Poloxamer 407 and polyvinyl alcohol (PVA) impacte the permeability of ibuprofen from water-based formulations. The procedures set forth in Example 13 were used for the evaluation.

TABLE 33

Effect of Thickening Agents and Poloxamer 407 on the Permeability of Ibuprofen

| Component wt % | Ibugel | Ibu 100823-X1 | Ibu 100823-X2 | Ibu 100823-X3 | Ibu 100823-X4 |
|---|---|---|---|---|---|
| Ibuprofen | 5.0 | 5.0 | 5.0 | 5.0 | 5.0 |
| Brij 30 | | 1.0 | 1.0 | 1.0 | 1.0 |
| Brij 78 | | 2.0 | 2.0 | 2.0 | 2.0 |
| Cholesterol | | 0.1 | 0.1 | 0.1 | 0 |
| Sodium carbonate | | 1.25 | 1.0 | 1.0 | 1.25 |
| Water | | 90.65 | 88.9 | 88.9 | 88.5 |
| HPC HY 121 | | 0 | 2 | 0 | 0 |
| HPC HY 117 | | 0 | 0 | 2.0 | 0.25 |
| PVA | | 0 | 0 | 0 | 1.5 |
| Poloxamer 407 | | 0 | 0 | 0 | 0.5 |
| Cum amt transported at 24 h (µg/cm2) | 19.23 | 18.61 | 19.29 | 13.37 | 17.98 |
| SEM | 3.85 | 8.899 | 4.86 | 6.48 | 6.09 |
| ER | 1.00 | 0.97 | 1.00 | 0.70 | 0.93 |

Figure 66:
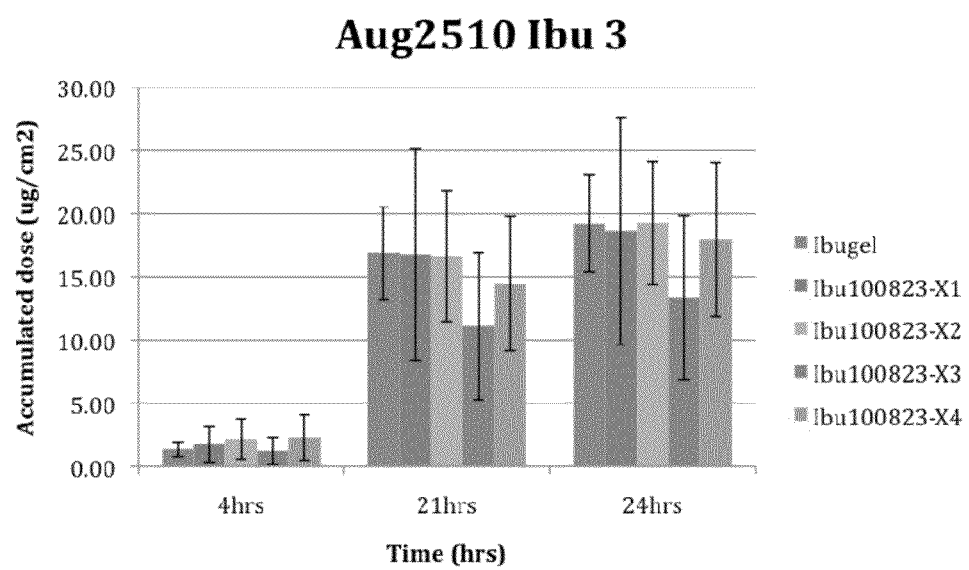
FIG. 66 illustrates the effect of thickening agents and Poloxamer 407 on the delivery of ibuprofen from water based formulations.

The results are shown in FIG. 66. The water based formulations containing thickening agents failed to demonstrate any delivery enhancement for ibuprofen. Ibuprofen permeability from water based formulations do not meet expectations for an ibuprofen topical foam formulation. The formulation containing a combination of PVA and Poloxamer 407, though capable of forming acceptable foams, failed to provide the necessary delivery enhancement.

Example 25

Evaluation of Ethanol-Free DMSO-Based Formulations

The development of an ethanol-free DMSO-based formulation was of interest in eliminating the formation of ibuprofen esterification-related degradant (Table 34). In addition, the overall reduction and minimization of DMSO in the formulation was of interest in the context of minimizing excipients. The procedures set forth in Example 13 were used for the evaluation.

The DMSO content was varied from 15% to 45.5% in formulations without ethanol, propylene glycol, and glycerin. Glycerin was eliminated from the formulation, to test its impact on the drying time of the foam upon application to the skin.

For formulations Ibu 1008025-05 to 1008025-07, 7.1% propylene glycol was included in the formulations. The concentration of Brij 30 was maintained at 1%, cholesterol was maintained at 0.1%, and Brij 78 was maintained at 1%, except for a formulation at 2% (100825-02). Anionic surfactants were removed from the formulation to evaluate whether acceptable formulations could be obtained with only nonionic surfactants.

taining 45.5% DMSO provided the highest delivery enhancement, lowering DMSO levels should provide more desirable foam characteristics.

Example 26

Effects of Varying Ethanol and Glycerine Levels on the Permeability of Ibuprofen The effect of varying levels of ethanol in formulations (0, 7.45%, and 11.2% ethanol at ~28% DMSO; and 0% ethanol at 15% DMSO) with or without glycerin were studied (Table 35A and B). The type and concentration of anionic surfactants were also varied. The objective of these experiments was to determine if glycerine and the anionic surfactants are critical to the performance of the formulation, primarily intended to minimize excipients in the formulation. The procedures set forth in Example 13 were used for the evaluation.

TABLE 34

Effect of Varying DMSO Content on the Permeability of Ibuprofen

| Component wt % | Ibugel | Ibu 100825-01 | Ibu 100825-02 | Ibu 100825-03 | Ibu 100825-04 | Ibu 100825-05 | Ibu 100825-06 | Ibu 100825-07 |
|---|---|---|---|---|---|---|---|---|
| Ibuprofen | 5.0 | 5.0 | 5.0 | 5.0 | 5.0 | 5.0 | 5.0 | 5.0 |
| DMSO | | 28.7 | 28.7 | 45.5 | 15.0 | 45.5 | 28.7 | 15.0 |
| Water | | 63.7 | 62.7 | 46.9 | 77.4 | 39.8 | 56.6 | 70.3 |
| Ethanol | | 0 | 0 | 0 | 0 | 0 | 0 | 0 |
| Propylene Glycol | | 0 | 0 | 0 | 0 | 7.1 | 7.1 | 7.1 |
| Glycerin | | 0 | 0 | 0 | 0 | 0 | 0 | 0 |
| Brij 30 | | 1.0 | 1.0 | 1.0 | 1.0 | 1.0 | 1.0 | 1.0 |
| Cholesterol | | 0.1 | 0.1 | 0.1 | 0.1 | 0.1 | 0.1 | 0.1 |
| Sodium carbonate | | 0.5 | 0.5 | 0.5 | 0.5 | 0.5 | 0.5 | 0.5 |
| Brij 78 | | 1.0 | 2.0 | 1.0 | 1.0 | 1.0 | 1.0 | 1.0 |
| Cum amt transported at 24 h ($\mu$g/cm2) | 17.04 | 47.44 | 54.83 | 88.51 | 47.09 | 126.48 | 70.47 | 62.75 |
| SEM | 4.06 | 5.70 | 5.91 | 7.58 | 4.79 | 7.72 | 8.83 | 7.50 |
| ER | 1.00 | 2.78 | 3.22 | 5.19 | 2.76 | 7.42 | 4.13 | 3.68 |

Figure 67:
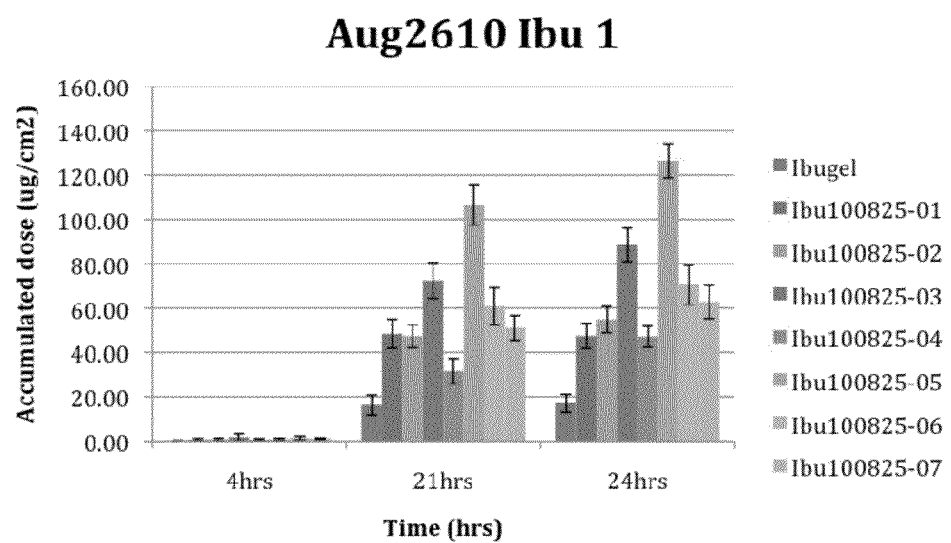
FIG. 67 illustrates the effect of varying DMSO content on the delivery of ibuprofen.

The results are shown in FIG. 67. A two- to seven-fold increase in the delivery of ibuprofen as compared to Ibugel was observed, dependent on formulation composition. In formulations without ethanol, glycerin or propylene glycol, increasing the DMSO content from 15% to 28.7% did not appear to have a meaningful impact on permeability (100825-04 and 100825-01). Increasing the concentration of DMSO to 45.5% seemed likely to have a positive impact on permeability of ibuprofen (100825-03) from formulations without ethanol, glycerine or propylene glycol.

In formulations containing 7.1% propylene glycol but without glycerin or ethanol, raising the DMSO levels from 15% to 28.7% did not appear to have a meaningful impact on permeability. Increasing the DMSO content to 45.5% in these formulations is likely to have a positive impact on the permeability of ibuprofen.

Increasing the concentration of Brij 78 to 2% in the formulations containing 28.7% DMSO seems unlikely to impact the permeability of ibuprofen. Although the formulations con-

TABLE 35

Effect of Varying Ethanol and Glycerin Levels

| Component wt % | Ibugel | Ibu 100802-01 | Ibu 100802-04-F2 | Ibu 100825-06 | Ibu 100825-07 |
|---|---|---|---|---|---|
| Ibuprofen | 5.0 | 5.0 | 5.0 | 5.0 | 5.0 |
| DMSO | | 28.74 | 29.69 | 28.7 | 15.0 |
| Water | | 43.68 | 36.8 | 56.6 | 70.3 |
| Ethanol | | 7.45 | 11.2 | 0 | 0 |
| Propylene Glycol | | 7.07 | 7.31 | 7.1 | 7.1 |
| Glycerin | | 4.86 | 5.07 | 0 | 0 |
| Brij 30 | | 1.3 | 1.0 | 1.0 | 1.0 |
| Cholesterol | | 0.1 | 0.1 | 0.1 | 0.1 |
| SLS | | 1.3 | 0 | 0 | 0 |
| Sodium carbonate | | 0.5 | 0.5 | 0.5 | 0.5 |
| SLES | | 0 | 2.0 | 0 | 0 |
| Brij 78 | | 0 | 1.0 | 1.0 | 1.0 |

TABLE 35-continued

Effect of Varying Ethanol and Glycerin Levels

| Component wt % | Ibugel | Ibu 100802-01 | Ibu 100802-04-F2 | Ibu 100825-06 | Ibu 100825-07 |
|---|---|---|---|---|---|
| Cum amt transported at 24 h (µg/cm2) | 8.10 | 51.44 | 46.16 | 21.49 | 20.65 |
| SEM | 1.75 | 7.36 | 6.42 | 2.10 | 2.55 |
| ER | 1.00 | 6.35 | 5.70 | 2.65 | 2.55 |

TABLE 35B

Effect of Varying Ethanol and Glycerin Levels II

| Component (wt %) | Ibu 100818-08 F11 |
|---|---|
| Ibuprofen | 5.0 |
| Amphosol | 2.73 |
| Ethanol | 16.39 |
| Transcutol | 10.93 |
| Lactic Acid | 0 |
| Water | 60.80 |
| TEC | 0 |
| Brij 30 | 1 |
| Brij 78 | 1 |
| Cholesterol | 0.15 |
| Sodium carbonate | 1.0 |
| SLES | 1.0 |
| Cum amt transported at 24 h (µg/cm2) | 6.69 |
| SEM | 1.54 |
| ER | 0.83 |

Figure 68:
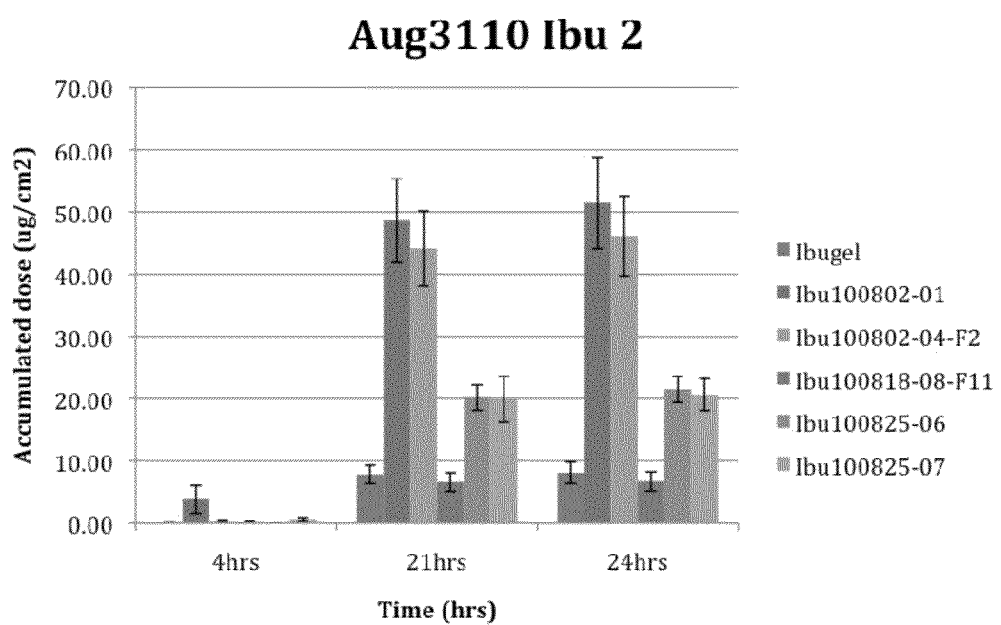
FIG. 68 illustrates the effect of varying ethanol and glycerin levels on the delivery of ibuprofen.)

The results are shown in FIG. 68. For the DMSO based formulations, depending on formulation type, a two- to six-fold increase in delivery of ibuprofen as compared to Ibugel was observed. Increasing ethanol concentrations from 7.45% to 11.2% while maintaining DMSO concentration at ~28% and glycerin at ~5% appeared to have no impact on the permeability of ibuprofen (100802-01 vs. 100802-04-F2). Complete removal of ethanol and glycerin from the formulation while maintaining DMSO levels at 28% may have the effect of decreasing the permeability of ibuprofen (100825-06). The comparable ER observed for formulations 100825-06 and 100825-07 indicated that the delivery of ibuprofen may not be influenced by DMSO levels in the range of 15 to 28.7%. The removal of anionic surfactants from the formulation was feasible without impacting ibuprofen delivery characteristics.

Example 27 pH Stability of DMSO-Based Formulations

In order to confirm the pH stability of DMSO formulations, the following formulations were prepared and maintained at 67.6° C. for 1 week (Table 36).

TABLE 36

Composition of Formulations Prepared for pH Study

| Component wt % | Ibu 100802-4-F1 | Ibu 100802-4-F2 | Ibu 100802-4-F3 | Ibu 100802-01 |
|---|---|---|---|---|
| Ibuprofen | 5.0 | 5.0 | 5.0 | 5.0 |
| DMSO | 29.7 | 29.7 | 29.7 | 28.7 |

TABLE 36-continued

Composition of Formulations Prepared for pH Study

| Component wt % | Ibu 100802-4-F1 | Ibu 100802-4-F2 | Ibu 100802-4-F3 | Ibu 100802-01 |
|---|---|---|---|---|
| Water | 37.3 | 36.8 | 41.9 | 43.7 |
| Ethanol | 11.5 | 11.5 | 11.5 | 7.4 |
| Propylene Glycol | 7.3 | 7.3 | 7.3 | 7.1 |
| Glycerin | 5.0 | 5.1 | 0 | 4.9 |
| Brij 30 | 1.0 | 1.0 | 1.0 | 1.3 |
| Cholesterol | 0.1 | 0.1 | 0.1 | 0.1 |
| SLS | 0 | 0 | 0 | 2.0 |
| Sodium carbonate | 0 | 0.5 | 0.5 | 0.5 |
| SLES | 2.0 | 2.0 | 2.0 | 0 |
| Brij 78 | 1.0 | 1.0 | 1.0 | 1.0 |
| pH at T = 0 | 4.71 | 6.65 | 6.61 | 6.48 |
| pH at T = 7 d (storage at 67.6° C.) | 4.39 | 6.67 | 6.65 | 6.46 | pH measurements indicated no changes to the pH of the formulations over a period of 7 days under the conditions studied.

Example 28

Selection and Properties of Ibuprofen Foam Formulations: Selection Conclusions from Formulation Screening Activities The overall conclusions from the formulation screening studies described above may be summarized as follows.

The degree of enhancement of ibuprofen delivery from DMSO based formulations is dependant on the concentration of DMSO in the formulations.

Two-fold enhancement in delivery of ibuprofen over comparator Ibugel is feasible for ethanol-containing and ethanol-free, DMSO-based formulation.

The permeation of ibuprofen from DMSO-based formulations is likely to be independent of the surfactant concentration; however, the presence of surfactants may be advantageous in producing acceptable foam characteristics.

The use of thickening agents, such as HPC HY 121, is unlikely to impact the permeability of ibuprofen from DMSO based formulations.

Selection of Ibuprofen Foam Formulations

The formulation development activities described in the previous examples led to the identification of the following types of formulation chassis for the ibuprofen foamable formulations:

1. DMSO based formulations containing ethanol and glycerin, e.g., 100826-01 (02); and 2. DMSO based formulations without ethanol and glycerine, e.g., 100825-07.

In general, the DMSO based formulations provide greater than two-fold enhancement in the delivery of ibuprofen. Both formulation types were included in the stability studies.

Formulation variations for the above-described formulation chassis were manufactured at the 100 g scale and tested for stability. Table 37 provides the composition of the formulations that were tested for stability.

TABLE 37

Composition of Formulations Selected for Stability Studies

|  | 100825-06 (9210) | 100825-07 (9210) | 100826-01 (9310) | 100826-02 (9310) | 100826-03 (9310) | 100826-04 (9310) | 100826-05 (9310) | 100826-06 (9310) |
|---|---|---|---|---|---|---|---|---|
| Ibuprofen | 5.0 | 5.0 | 5.0 | 5.0 | 5.0 | 5.0 | 5.0 | 5.0 |
| DMSO | 28.7 | 15.0 | 28.74 | 28.74 | 28.74 | 28.74 | 28.74 | 28.74 |
| Water | 55.3 | 68.8 | 43.88 | 42.88 | 43.58 | 42.88 | 43.98 | 43.14 |
| Ethanol | 0 | 0 | 7.45 | 7.45 | 7.45 | 7.45 | 7.45 | 7.45 |
| Propylene Glycol | 7.1 | 7.1 | 7.07 | 7.07 | 7.07 | 7.07 | 7.07 | 7.07 |
| Glycerin | 0 | 0 | 4.86 | 4.86 | 4.86 | 4.86 | 4.86 | 4.86 |
| Brij 30 | 1.0 | 1.0 | 1.0 | 1.0 | 1.0 | 1.0 | 1.0 | 1.0 |
| Cholesterol | 0.1 | 0.1 | 0.2 | 0.2 | 0.2 | 0.2 | 0.1 | 0.2 |
| SLS | 0 | 0 | 0 | 0 | 0.3 | 0.3 | 0 | 0 |
| Sodium carbonate | 0.75 | 1.0 | 0.5 | 0.5 | 0.75 | 0.5 | 0.75 | 0.5 |
| SLES | 0 | 0 | 0.3 | 0.3 | 0 | 0 | 0 | 0 |
| Brij 78 | 2.0 | 2.0 | 1.0 | 2.0 | 1.0 | 2.0 | 1.0 | 2.0 |
| pH (T = 0) | 7.04 | 7.06 | 6.69 | 6.70 | 6.71 | 6.71 | 6.95 | 6.72 |

Example 29

Selection and Properties of Ibuprofen Foam Formulations: Permeation Study Results The formulations tested are described in Example 28. Table 38 provides a summary of the ibuprofen delivery characteristics of the various formulations tested for stability. The permeation characteristics of the formulations at T=0 months were evaluated using the experimental procedures discussed in Example 13. All permeation experiments were conducted using dermatomed porcine skin.

TABLE 38

Summary of Ibuprofen Delivery from Formulations Used for Stability Studies

|  | 100825-06 (9210) | 100825-07 (9210) | 100826-01 (9310) | 100826-02 (9310) | 100826-03 (9310) | 100826-04 (9310) | 100826-05 (9310) | 100826-06 (9310) | 100831-04 (9210) | 100831-01 (9210) |
|---|---|---|---|---|---|---|---|---|---|---|
| Cum amt transported at 24 h (ug/cm2) | 60.6 | 37.3 | 81.9 | 69.7 | 96.8 | 88.3 | 97.2 | 90.0 | 39.6 | 27.5 |
| SEM | 6.7 | 2.8 | 7.0 | 4.2 | 6.5 | 7.7 | 14.0 | 7.9 | 9.9 | 2.8 |
| ER | 3.41 | 2.10 | 3.75 | 3.19 | 4.43 | 4.04 | 4.45 | 4.12 | 2.18 | 1.51 |

Figure 69:
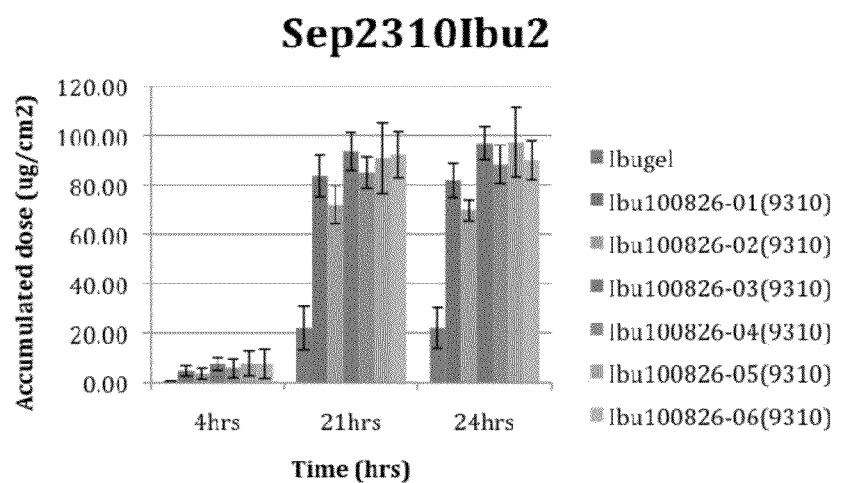
FIG. 69 illustrates ibuprofen permeability from formulations selected for stability studies.
Figure 70:
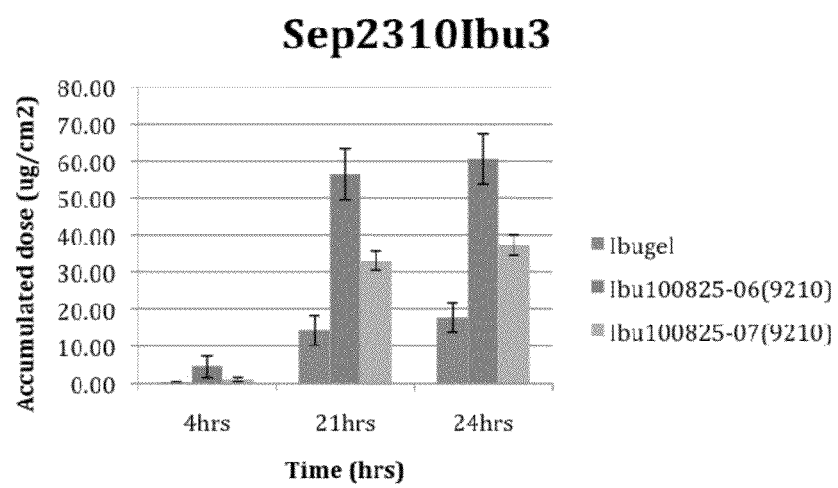
FIG. 70 illustrates ibuprofen permeability from formulations selected for stability studies.
Figure 71:
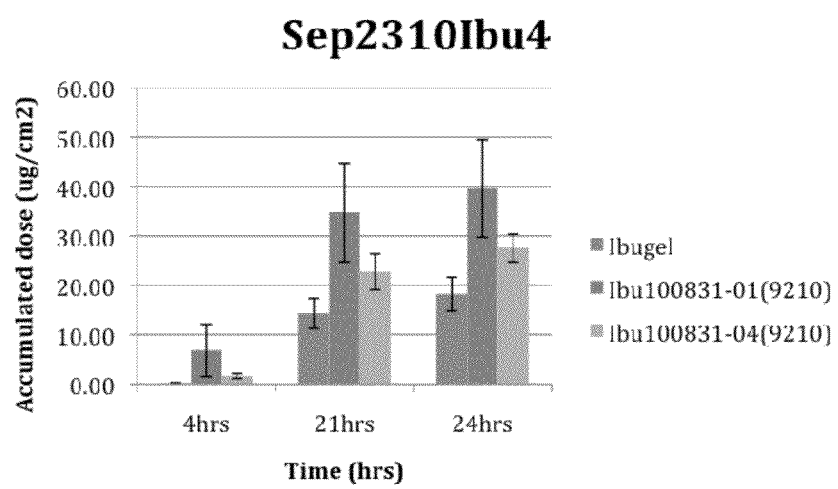
FIG. 71 illustrates ibuprofen permeability from formulations selected for stability studies.

The results are shown in FIGS. 69-71. A two- to four-fold increase in the delivery of ibuprofen was observed at 24 h for all the DMSO based formulations (100825 and 100826 series).

Example 30

Selection and Properties of Ibuprofen Foam Formulations: Stability Study Results The formulations tested are described in Example 28. For the stability study, the formulations were stored in glass vials at 25° C., 40° C. and 70° C. The samples at 25° C. and 40° C. will be analyzed for pH, ibuprofen concentration, total impurities and Compound A at T=0, T=1, and T=3 months, while the 70° C. samples were tested at T=0, 9, 17, and 27 days of storage. A summary of the data is presented in Table 39.

optimal stability of ibuprofen, and the ethanol containing formulation 100826-05 was predicted to have the lowest rate of esterification of ibuprofen due to its higher pH value.

Example 31

Selection and Properties of Ibuprofen Foam Formulations: Skin Irritation Study Results The formulations tested are described in Example 28. Concurrent with the stability studies, two DMSO-based foam formulations were tested for skin irritation using the EpiSkin® test model (In Vitro Assessment of the Dermal Irritation Potential of Three Formulations Using the EpiSkin® Test System (Study conducted at Charles River, Edinburgh, UK.).

TABLE 39

Formulation Stability After 3 Months at 25° C. and 40° C.

| | 25° C. storage condition | | | | 40° C. storage condition | | | |
|---|---|---|---|---|---|---|---|---|
| Formulation ID | IBU (%) | Compound A (%) | Total impurities (%) | ΔpH | IBU (%) | Compound A (%) | Total impurities (%) | ΔpH |
| 100825-06 | 99.8 | 0.00 | 0.19 | −0.04 | 99.2 | 0.00 | 0.13 | −0.03 |
| 100825-07 | 100.2 | 0.00 | 0.05 | 0.11 | 100.6 | 0.00 | 0.06 | 0.12 |
| 100826-01 | 99.0 | 0.33 | 0.41 | 0.02 | 98.2 | 0.96 | 0.14 | 0.01 |
| 100826-02 | 97.8 | 0.31 | 0.42 | 0.09 | 97.8 | 0.95 | 0.12 | 0.03 |
| 100826-03 | 99.2 | 0.31 | 0.40 | −0.05 | 98.8 | 0.91 | 0.13 | −0.06 |
| 100826-04 | 99.2 | 0.29 | 0.42 | −0.02 | 98.8 | 0.90 | 0.06 | −0.02 |
| 100826-05 | 98.4 | 0.12 | 0.28 | 0.02 | 98.6 | 0.37 | 0.17 | −0.01 |
| 100826-06 | 99.0 | 0.34 | 0.43 | 0.05 | 98.8 | 1.04 | 0.17 | 0.04 |
| 100831-01 | 98.6 | 0.19 | 0.42 | 0.01 | 98.8 | 0.62 | 0.27 | 0 |
| 100831-02 | 99.0 | 0.50 | 0.53 | −0.05 | 98.8 | 1.53 | 0.42 | −0.06 |

Results indicated that all ten formulations indicate excellent stability for ibuprofen content as well as pH of the formulations. The presence of Compound A was not observed in the ethanol-free formulations 100825-06 and 100825-07 consistent with the hypothesis that Compound A is the ethyl ester of ibuprofen. Formulations in the 100826 series and formulations 100831-01 and 100831-04 indicate the presence of Compound A; on par with the production of the degradant in gel formulations containing TEC. The stability results indicate that the primary factors controlling the rate of production of Compound A were pH of formulation and the concentration of ethanol (decreasing concentration of Compound A produced with increasing pH and ethanol content).

Based on the stability data available, the lowest levels of Compound A and total impurities were observed in formulation 100825-07 and formulation 100826-05. The ethanol free formulation 100825-07 was expected to provide maximum In this study, the two formulations were tested in the SkinEthic EpiSkin® in vitro irritation assay using human keratinocytes derived from healthy donors and grown in vitro to reconstruct a functional model of the human epidermis. The results of the assay were similar for the two formulations and both were demonstrated to be non-irritants (no category) when tested in the EpiSkin® in vitro irritation assay.

Example 32

Ibuprofen Foam Formulations: Foam Stability Study

An additional set of ibuprofen formulations were prepared for foam stability testing. The composition of the formulations is set forth in Table 40.

TABLE 40

Formulation Compositions

| Formulation No. (Lot No.) | IBU | Brij 30 | Brij 78 | PG | GLY | Na₂CO₃ | EtOH | H₂O | DMSO |
|---|---|---|---|---|---|---|---|---|---|
| 1 (F110128-1) | 5 | 1 | 1 | 7.1 | 4.9 | 0.75 | 18.06 | 18.06 | 44.14 |
| 2 (F110128-2) | 5 | 1 | 1 | 7.1 | 4.9 | 0.75 | 0.00 | 36.11 | 44.14 |
| 3 (F110128-3) | 5 | 1 | 1 | 7.1 | 4.9 | 0.75 | 33.10 | 11.03 | 36.11 |
| 4 (F1101311) | 5 | 1 | 1 | 7.1 | 4.9 | 0.75 | 11.03 | 33.10 | 36.11 |
| 5 (F110131-2) | 5 | 1 | 1 | 7.1 | 4.9 | 0.75 | 26.08 | 26.08 | 28.09 |
| 6 (F110131-3) | 5 | 1 | 1 | 7.1 | 4.9 | 0.75 | 0.00 | 52.16 | 28.09 |
| 7 (F110131-4) | 5 | 1 | 1 | 7.1 | 4.9 | 0.75 | 45.14 | 15.05 | 20.06 |
| 8 (F110131-5) | 5 | 1 | 1 | 7.1 | 4.9 | 0.75 | 15.05 | 45.14 | 20.06 |
| 9 (F110131-6) | 5 | 1 | 1 | 7.1 | 4.9 | 0.75 | 34.11 | 34.11 | 12.04 |
| 10 (F110201-1) | 5 | 1 | 1 | 7.1 | 4.9 | 0.75 | 0.00 | 68.21 | 12.04 |
| 11 (F110201-2) | 5 | 1 | 1 | 7.1 | 4.9 | 0.75 | 57.18 | 19.06 | 4.01 |
| 12 (F110201-3) | 5 | 1 | 1 | 7.1 | 4.9 | 0.75 | 19.06 | 57.18 | 4.01 |
| 13 (F110203-1) | 5 | 1 | 1 | 7.1 | 4.9 | 0.75 | 10.03 | 10.03 | 60.19 |
| 14 (F110203-2) | 5 | 1 | 1 | 7.1 | 4.9 | 0.75 | 5.02 | 15.05 | 60.19 |
| 15 (F110203-3) | 5 | 1 | 1 | 7.1 | 4.9 | 0.75 | 0.00 | 20.06 | 60.19 |

All compositions in % (w/w).
IBU = ibuprofen;
PG = propylene glycol;
GLY = glycerol.

Figure 72:
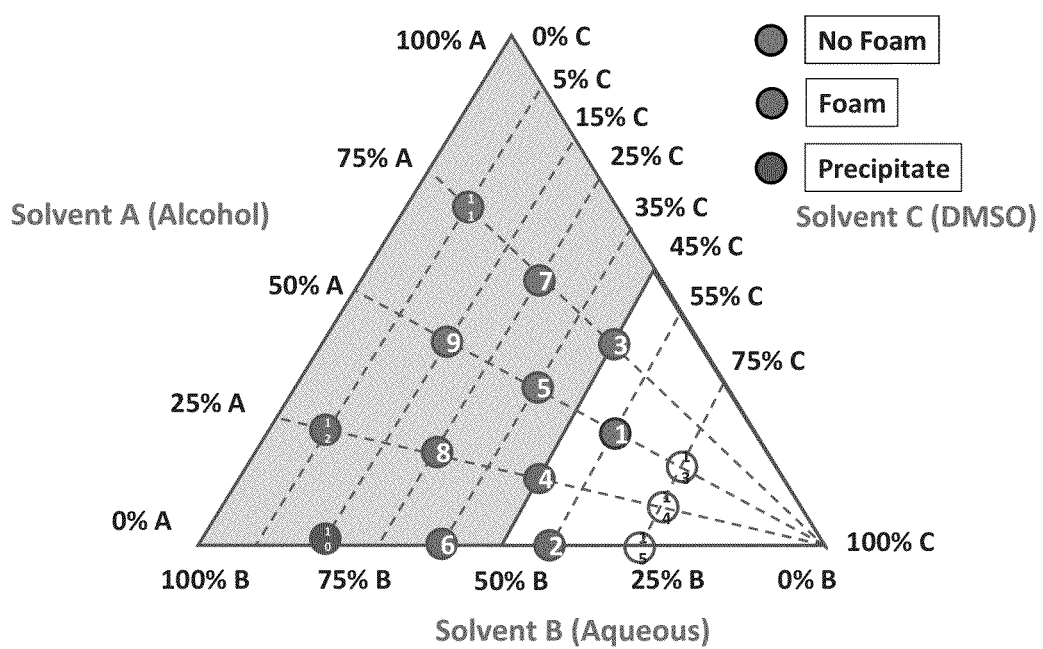
FIG. 72 illustrates the qualitative properties of the ibuprofen test formulations (foam/no foam/precipitate).
Figure 73:
FIG. 73 illustrates the foam produced from formulation 1 (F110128-1).
Figure 74:
FIG. 74 illustrates the foam produced from formulation 2 (F110128-2).
Figure 75:
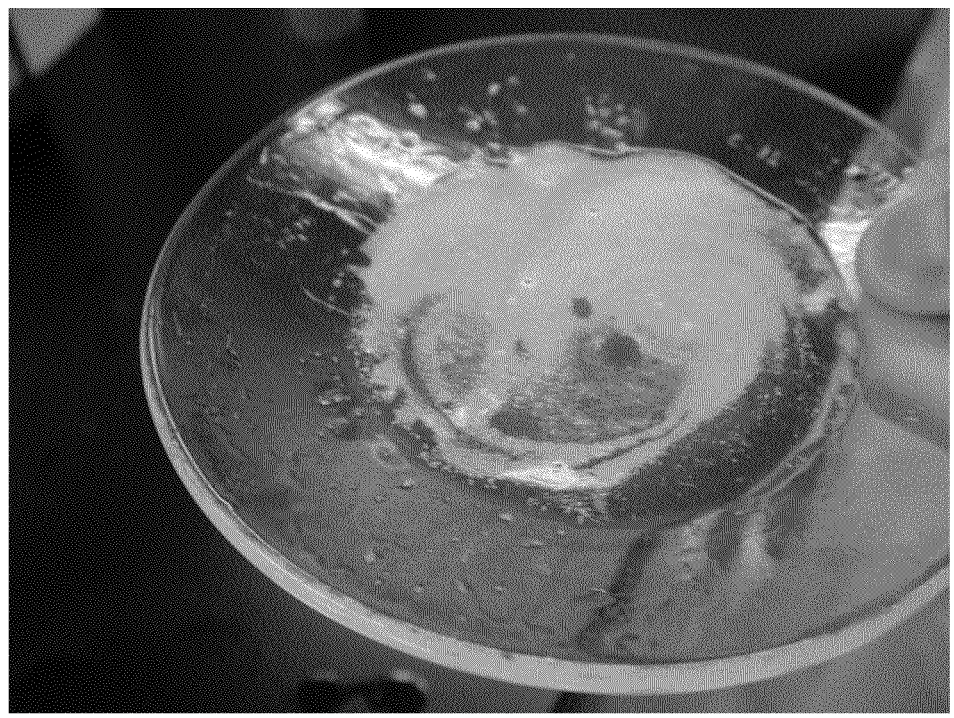
FIG. 75 illustrates the foam produced from formulation 3 (F110128-3).
Figure 76:
FIG. 76 illustrates the foam produced from formulation 4 (F110131-1).
Figure 77:
FIG. 77 illustrates the foam produced from formulation 5 (F110131-2).
Figure 78:
FIG. 78 illustrates the foam produced from formulation 6 (F110131-3).
Figure 79:
FIG. 79 illustrates the foam produced from formulation 7 (F110131-4).
Figure 80:
FIG. 80 illustrates the foam produced from formulation 8 (F110131-5).
Figure 81:
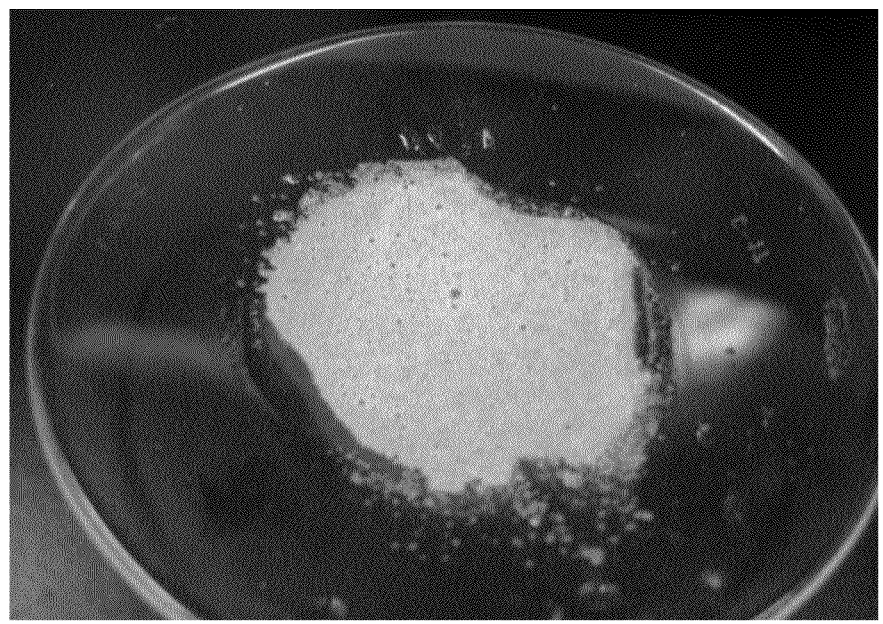
FIG. 81 illustrates the foam produced from formulation 9 (F110131-6).
Figure 82:
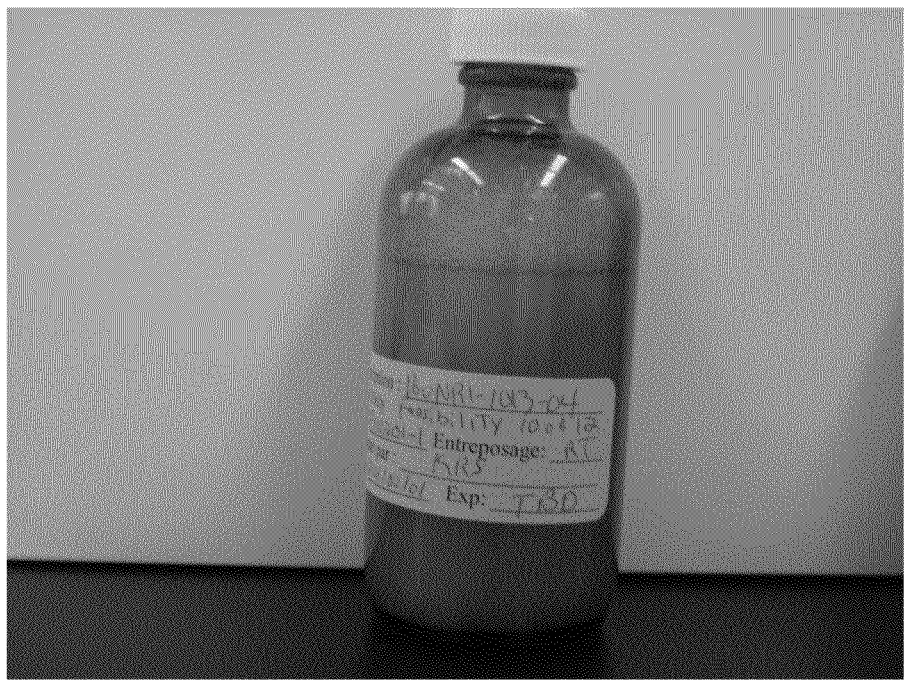
FIG. 82 illustrates the foam produced from formulation 10 (F110201-1).
Figure 83:
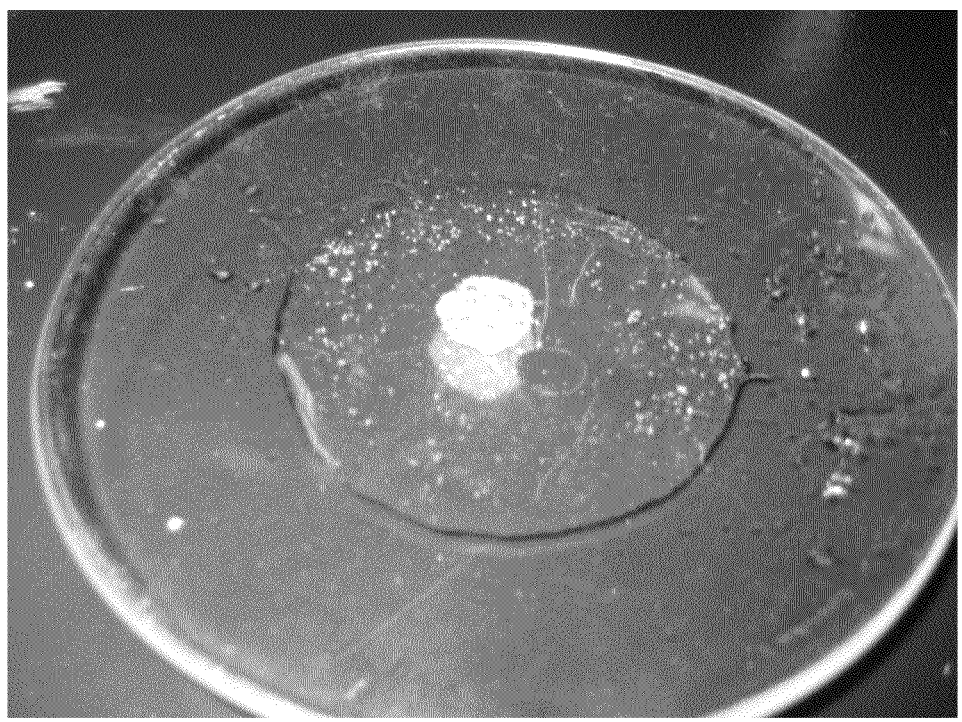
FIG. 83 illustrates the foam produced from formulation 11 (F110201-2).
Figure 84:
FIG. 84 illustrates the foam produced from formulation 12 (F110201-3).
Figure 85:
FIG. 85 illustrates the foam produced from formulation 13 (F110203-1).
Figure 86:
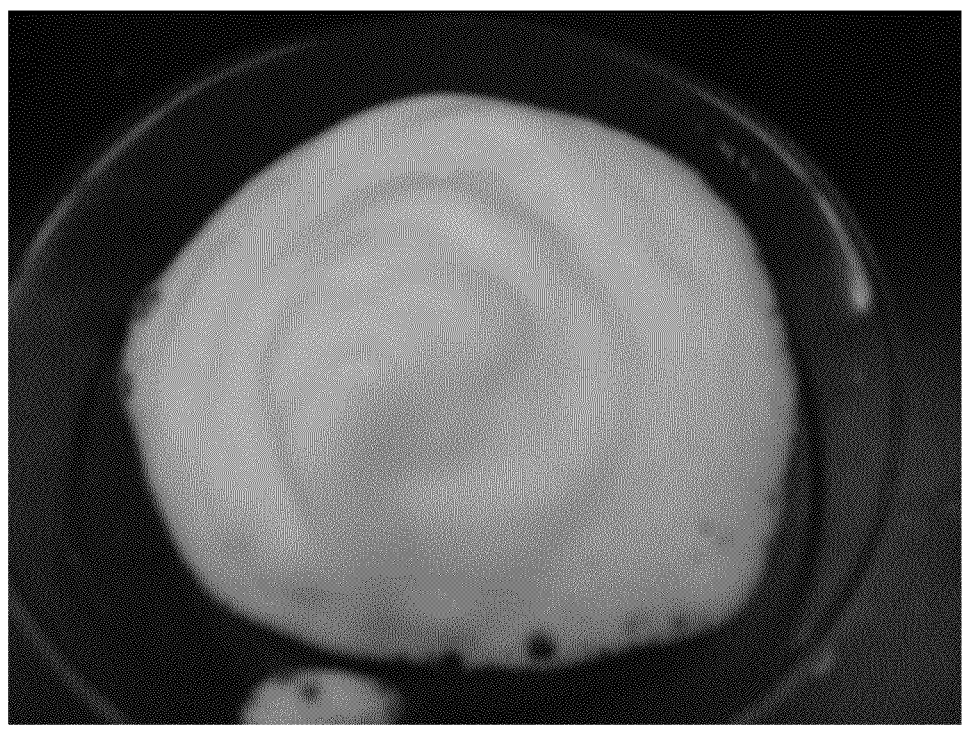
FIG. 86 illustrates the foam produced from formulation 14 (F110203-2).
Figure 87:
FIG. 87 illustrates the foam produced from formulation 15 (F110203-3).

The foams were prepared by shaking in a calibrated cylinder for 10 sec as described before or by use of a Rexam M3 foaming head. The results are set forth in Table 41, Table 42, and FIGS. 72 through 87. Formulations 2, 4, 6, 8, 10, 12, 13, 14 and 15 formed foams. However, formulation 2 produced a cloudy solution, formulation 10 included a precipitate (FIG. 72), and formulation 13 produced a foam that was not firmed and collapsed quickly. Formulations 1, 3, 5, 7, 9, and 11 did not produce foams. Unlike ethanol, water and DMSO concentration variation did not seem to have impact on the foam quality. For these formulations, the more ethanol that there was in the formulation, the lower the foam's quality, and the faster the foam's collapse.

TABLE 41

Formulation Observations I (Foaming Head/Foamer)

| Formulation No. (Lot No.) | Formulation Description | Foam Description at Initial Time | Color of Foam at Initial Time | Complete Collapse Time |
|---|---|---|---|---|
| 1 (F110128-1) | Clear solution | Not firm, a film of liquid around the foam, with a lot of air bubbles | White | 2 min 58 sec |
| 2 (F110128-2) | Cloudy solution | Foam with a lot of air bubbles | White | 17 min 45 sec |
| 3 (F110128-3) | Clear solution | A pseudo foam (liquid) with a lot of air bubbles | Whitish | 25 sec |
| 4 (F1101311) | Clear solution | Firm, with a few air bubbles | White | 6 min 16 sec |
| 5 (F110131-2) | Clear solution | A pseudo foam (liquid) with a lot of air bubbles | Whitish | 52 sec |
| 6 (F110131-3) | Clear solution | Firm, with a few air bubbles | White | 11 min |
| 7 (F110131-4) | Clear solution | A pseudo foam (liquid) with a lot of air bubbles | Whitish | 20 sec |
| 8 (F110131-5) | Clear solution | Firm, with a few air bubbles | White | 8 min 30 sec |
| 9 (F110131-6) | Clear solution | A pseudo foam (liquid) with a lot of air bubbles | Whitish | 1 min 17 sec |
| 10 (F110201-1) | Precipitation | Firm, uniform, without air bubbles | White | 30 min |
| 11 (F110201-2) | Clear solution | A pseudo foam (liquid) with a lot of air bubbles | Whitish | 1 min 17 sec |
| 12 (F110201-3) | Clear solution | Firm, uniform, with a few air bubbles | White | 8 min 10 sec |
| 13 (F110203-1) | Clear solution | Foam with a lot of air bubbles | White | 7 min 15 sec |
| 14 (F110203-2) | Clear solution | More or less uniform, without air bubbles | White | 8 min 10 sec |

TABLE 41-continued

Formulation Observations I (Foaming Head/Foamer)

| Formulation No. (Lot No.) | Formulation Description | Foam Description at Initial Time | Color of Foam at Initial Time | Complete Collapse Time |
|---|---|---|---|---|
| 15 (F110203-3) | Clear solution | Firm, uniform, without air bubbles | White | 10 min 45 sec |

TABLE 42

Formulation Observations II (Shaker)

| Formulation No. (Lot No.) | Height | Complete Collapse Time | Collapse Speed |
|---|---|---|---|
| 1 (F110128-1) | 3.2 cm | 5 min 30 sec | 0.58 cm/min |
| 2 (F110128-2) | 2.2 cm | 52 min | 0.04 cm/min |
| 3 (F110128-3) | 1.4 cm | 1 min 41 sec | 0.83 cm/min |
| 4 (F1101311) | 2.4 cm | 5 min | 0.48 cm/min |
| 5 (F110131-2) | 2.2 cm | 2 min 45 sec | 0.80 cm/min |
| 6 (F110131-3) | 7.6 cm | 1 hr 50 min | 0.07 cm/min |
| 7 (F110131-4) | 0.8 cm | 1 min | 0.80 cm/min |
| 8 (F110131-5) | 4.2 cm | 14 min | 0.30 cm/min |
| 9 (F110131-6) | 1.4 cm | 1 min 23 sc | 1.01 cm/min |
| 10 (F110201-1) | 14 cm | 35 min | 0.40 cm/min |
| 11 (F110201-2) | 0.4 cm | 14 sec | 1.71 cm/min |
| 12 (F110201-3) | 12.6 cm | 28 min | 0.45 cm/min |
| 13 (F110203-1) | 3.2 cm | 1 min 13 sec | 2.63 cm/min |
| 14 (F110203-2) | 2.8 cm | 5 min 37 sec | 0.50 cm/min |
| 15 (F110203-3) | 4.8 cm | 013 min 50 sec | 0.35 cm/min |

It is understood that the examples and embodiments described herein are for illustrative purposes only. Various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

What is claimed is:

1. A foamable formulation, said formulation comprising:
   (i) dimethyl sulfoxide (DMSO); wherein DMSO is present in an amount ranging from about 12-80% w/w;
   (ii) a pharmaceutically active agent; wherein the active agent is selected from the group consisting of an anti-inflammatory steroid, a non-stereoidal anti-inflammatory drug, and a local anesthetic; and
   (iii) a polyalkylene glycol alkyl ether;
   wherein the formulation is foamable by manual aeration; and wherein the formulation comprises from 0 to 1% or from 30 to 45% w/w propellant.

2. The foamable formulation of claim 1, said formulation further comprising a monohydric lower alcohol.

3. The foamable formulation of claim 1, wherein said formulation comprises from 0 to 1% propellant.

4. The foamable formulation of claim 1, wherein said formulation comprises 15-80% w/w DMSO.

5. The foamable formulation of claim 1, wherein said active agent is a non-steroidal anti-inflammatory drug.

6. The foamable formulation of claim 5, wherein said non-steroidal anti-inflammatory drug is ibuprofen or a diclofenac salt.

7. The foamable formulation of claim 6, wherein said non-steroidal anti-inflammatory drug is ibuprofen;
   wherein the ibuprofen is present at 3-8% w/w; DMSO is present at 14-30% w/w; and the polyalkylene glycol alkyl ether is present at up to 3% w/w;
   wherein the formulation further comprises (iv) a diol and (v) water;
   wherein the formulation optionally further comprises a monohydric lower alcohol;
   wherein the diol is present at 5-9% w/w; the monohydric lower alcohol is present at 0-17% w/w; and the water is present at a concentration of q.s.

8. The foamable formulation of claim 6, wherein said diclofenac salt is diclofenac sodium.

9. The foamable formulation of claim 8, wherein diclofenac sodium is present at 1-10% w/w, DMSO is present at 20-60% w/w, and the polyalkylene glycol alkyl ether is present at up to 10% w/w;
   wherein the formulation further comprises (iv) a monohydric alcohol, (v) propylene glycol, and (vi) water; and
   wherein the monohydric alcohol is present at 1-50% w/w, propylene glycol is present at 1-15% w/w, and the water is present at a concentration of q.s.

10. The foamable formulation of claim 6, wherein the polyalkylene glycol alkyl ether is present at up to 5% w/w.

11. The foamable formulation of claim 10, further comprising 1-15% w/w glycerol.

12. The foamable formulation of claim 10, wherein said polyalkylene glycol alkyl ether is a polyethylene glycol alkyl ether.

13. The foamable formulation of claim 10, wherein said formulation further comprises a steroid.

14. The foamable formulation of claim 13, wherein said steroid is cholesterol; and wherein said formulation comprises at most 0.5% w/w of said steroid.

15. The foamable formulation of claim 13, wherein said formulation further comprises a surfactant.

16. The foamable formulation of claim 15, wherein said surfactant is a salt of an aryl sulfonate, alkyl sulfonate, aryl sulfate, or alkyl sulfate.

17. The foamable formulation of claim 16, wherein said salt is sodium dodecyl benzene sulfonate, sodium laureth sulfate, or sodium lauryl sulfate.

18. The foamable formulation of claim 13, wherein the formulation further comprises sodium carbonate.

19. A foam comprising the foamable formulation of claim 1.

20. The foam of claim 19, further comprising air.

21. The foam of claim 19, wherein the foam is a quick-breaking foam.

22. A method for treating a subject suffering from pain, said method comprising the topical administration to an afflicted area of said subject a therapeutically effective amount of the foamable formulation of claim 1, thereby treating the subject's pain.

23. The method of claim 22, wherein said pain is associated with osteoarthritis.

24. The method of claim 23, wherein said topical administration provides a reduction of pain over 12 weeks.

25. The method of claim 23, wherein said formulation is applied one, two, three, or four times daily.

26. The foamable formulation of claim 1, wherein said formulation comprises 12-48% w/w DMSO.

27. The foamable formulation of claim 26, wherein said formulation comprises 14-30% w/w DMSO.

28. The foamable formulation of claim 1, wherein said polyalkylene glycol alkyl ether is present at up to 2% w/w.

29. The foamable formulation of claim 4, wherein said formulation comprises 25-80% w/w DMSO.

30. A method for manually foaming the foamable formulation of claim 1, the method comprising the steps of:
   (i) providing a dispenser comprising a reservoir operably linked in fluid communication with a release assembly;
   (ii) filling the reservoir with the foamable formulation; and
   (iii) actuating the release assembly to manually aerate the foamable formulation, thereby releasing a foam from the release assembly.

* * * * *